United States Patent
Brown et al.

(10) Patent No.: US 12,234,227 B2
(45) Date of Patent: Feb. 25, 2025

(54) PYRAZOLE DERIVATIVES AS H4 ANTAGONIST COMPOUNDS

(71) Applicant: NXERA PHARMA UK LIMITED, Cambridge (GB)

(72) Inventors: Giles Albert Brown, Cambridge (GB); Miles Stuart Congreve, Cambridge (GB); Barry John Teobald, Cambridge (GB); Charlotte Fieldhouse, Cambridge (GB); Nigel Alan Swain, Cambridge (GB); Mark Pickworth, Cambridge (GB); Giovanni Bottegoni, Cambridge (GB)

(73) Assignee: NXERA PHARMA UK LIMITED, Cambridge (GB)

( * ) Notice: Subject to any disclaimer, the term of this patent is extended or adjusted under 35 U.S.C. 154(b) by 694 days.

(21) Appl. No.: 17/285,776

(22) PCT Filed: Oct. 21, 2019

(86) PCT No.: PCT/GB2019/052997
§ 371 (c)(1),
(2) Date: Apr. 15, 2021

(87) PCT Pub. No.: WO2020/079457
PCT Pub. Date: Apr. 23, 2020

(65) Prior Publication Data
US 2021/0300906 A1    Sep. 30, 2021

(30) Foreign Application Priority Data
Oct. 19, 2018  (GB) .................................. 1817047

(51) Int. Cl.
| | | |
|---|---|---|
| *C07D 403/14* | (2006.01) | |
| *C07D 401/14* | (2006.01) | |
| *C07D 471/04* | (2006.01) | |
| *C07D 487/04* | (2006.01) | |

(52) U.S. Cl.
CPC ......... *C07D 403/14* (2013.01); *C07D 401/14* (2013.01); *C07D 471/04* (2013.01); *C07D 487/04* (2013.01)

(58) Field of Classification Search
CPC .. C07D 403/14; C07D 401/14; C07D 471/04; C07D 487/04; C07D 405/14; A61P 1/04; A61P 11/06; A61P 17/04; A61P 19/02; A61P 29/00; A61K 31/506
See application file for complete search history.

(56) References Cited

FOREIGN PATENT DOCUMENTS

| | | | | |
|---|---|---|---|---|
| EP | 1103551 A1 | 5/2001 | | |
| RU | 2489430 C2 | 8/2013 | | |
| RU | 2573828 C2 | 1/2016 | | |
| WO | WO-2005054239 A1 * | 6/2005 | ........... | C07D 403/04 |
| WO | 2007/072163 A2 | 6/2007 | | |
| WO | 2008031556 A2 | 3/2008 | | |
| WO | 2008/060766 A2 | 5/2008 | | |
| WO | 2008/100565 A1 | 8/2008 | | |
| WO | 2009/077608 A1 | 6/2009 | | |
| WO | 2009068512 A1 | 6/2009 | | |
| WO | 2009080721 A2 | 7/2009 | | |
| WO | 2010/059658 A1 | 5/2010 | | |
| WO | 2010/108059 A1 | 9/2010 | | |
| WO | 2011059839 A1 | 5/2011 | | |
| WO | 2011076878 A1 | 6/2011 | | |
| WO | 2014078637 A1 | 5/2014 | | |
| WO | 2018023029 A1 | 2/2018 | | |

OTHER PUBLICATIONS

Walter et al., (2011), The Histamine H4 receptor: Targeting inflammatory disorders, European Journal of Pharmacology, 668, 1-5 (Year: 2011).*
Beasley et al., (Sep. 12, 2015), Risk factors for asthma: is prevention possible?, Lancet, 386, 1075-1085 (Year: 2015).*
Mollanazar et al. (May 1, 2015), Mediators of Chronic Pruritus in Atopic Dermatitis: Getting the Itch Out?, Clinic Rev. Alleg. Immunol, 51, 263-292 (Year: 2015).*
Savall et al., (Feb. 4, 2014), Discovery and SAR of 6-alkyl-2,4-diaminopyrimidines as Histamine H4 Receptor Antagonists, J. Med. Chem., 57, 2429-2439 (Year: 2014).*
Correa et al., (2015), Histamine H4 Receptor Ligands: Future Applications and State of Art, Chem. Biol. Drug. Des., 85, 461-480 (Year: 2015).*

(Continued)

*Primary Examiner* — Juliet C Switzer
*Assistant Examiner* — Dawanna Shar-Day White
(74) *Attorney, Agent, or Firm* — Barnes & Thornburg LLP

(57) ABSTRACT

Novel compounds of formula (1):

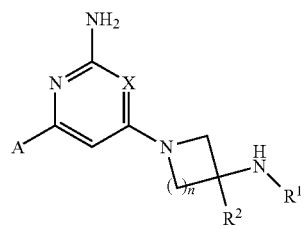

and salts thereof, wherein A; X; n; $R^1$ and $R^2$ are defined herein, are disclosed, as well as their use in treating, preventing, ameliorating, controlling or reducing the risk of disorders associated with H4 receptors.

17 Claims, 1 Drawing Sheet

(56) References Cited

OTHER PUBLICATIONS

Altenbach et al., (Oct. 2008), Structure-activity studies on a series of a 2-aminopyrimidine-containing histamine H4 receptor ligands, J. Med. Chem., 51, 6571-6580 (Year: 2008).*

Altenbach et al., Structure-activity studies on a series of a 2-aminopyrimidine-containing histamine H4 receptor ligands. J Med Chem. Oct. 23, 2008;51(20):6571-80.

Medina et al., Structure-based design of potent and selective 3-phosphoinositide-dependent kinase-1 (PDK1) inhibitors. J Med Chem. Mar. 24, 2011;54(6):1871-95.

International Search Report and Written Opinion for Application No. PCT/GB2019/052997, dated Nov. 26, 2019, 10 pages.

Great Britain Search Report for Application No. GB1817047.2, dated Apr. 5, 2019, 4 pages.

Savall et al., The effect of pK(a) on pyrimidine/pyridine-derived histamine H4 ligands. Bioorg Med Chem Lett. Dec. 1, 2014;24(23):5489-92.

Andaloussi et al., A novel series of histamine H4 receptor antagonists based on the pyrido[3,2]pyrimidine scaffold: comparison of hERG binding and target residence time with PF-3893787. Bioorg Med Chem Lett. May 1, 2013;23 (9):2663-70.

Ko et al., Discovery of a Novel Highly Selective Histamine H4 Receptor Antagonist for the Treatment of Atopic Dermatitis. J Med Chem. Mar. 26, 2018;61(7):2949-61.

Mowbray et al., Challenges of drug discovery in novel target space. The discovery and evaluation of PF-3893787: a novel histamine H4 receptor antagonist. Bioorg Med Chem Lett. Nov. 1, 2011;21(21)6596-602.

Thurmond et al., Clinical Development of Histamine H4 Receptor Antagonists. Handb Exp Pharmacol. 2017:241:301-320.

Venable et al., Preparation and biological evaluation of indole, benzimidazole, and thienopyrrole piperazine carboxamides: potent human histamine h(4) antagonists. J Med Chem. Dec. 29, 2005;48(26):8289-98.

* cited by examiner

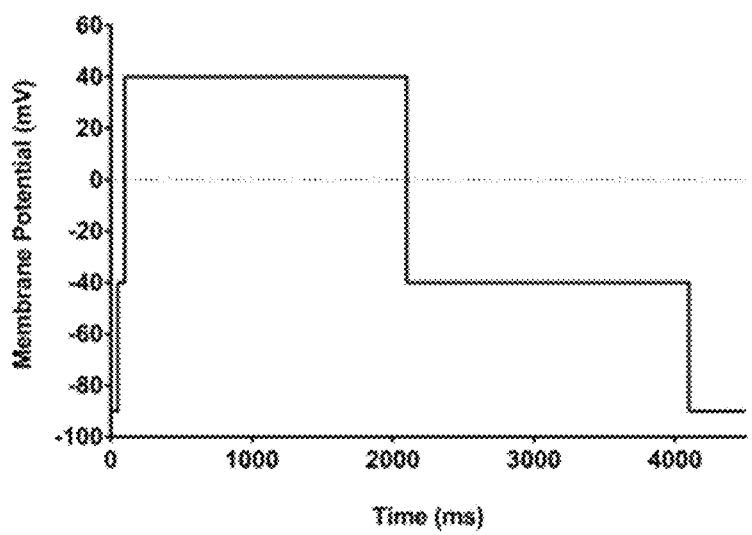

PYRAZOLE DERIVATIVES AS H4 ANTAGONIST COMPOUNDS

CROSS-REFERENCE TO RELATED APPLICATIONS

This application is a 35 U.S.C. § 371 national stage filing of International Application No. PCT/GB2019/052997, filed on Oct. 21, 2019, which claims priority to United Kingdom Application No. 1817047.2, filed on Oct. 19, 2018, the entire contents of each of which are incorporated herein by reference.

This application relates to novel compounds and their use as Histamine H4 receptor antagonists. Compounds described herein may be useful in the treatment or prevention of diseases in which H4 receptors are involved. The application is also directed to pharmaceutical compositions comprising these compounds and the manufacture and use of these compounds and compositions in the prevention or treatment of such diseases in which H4 receptors are involved.

BACKGROUND OF THE INVENTION

Histamine is a short-acting biogenic amine generated in mast cells where it is stored in cytosolic granules and released in response to various immunological and non-immunological stimuli. Histamine release from mast cells has been traditionally associated with mild to severe signs and symptoms that characterize hypersensitivity reactions, including erythema, urticaria, itching, tachycardia, hypotension, ventricular fibrillations, bronchospasm, and cardiac and respiratory arrest. To date, numerous additional sources have been identified, including basophils, neurons and cancer cells. In addition to modulating a wide range of physiological processes, histamine is implicated in pathological conditions including allergies and anaphylaxis, asthma and chronic inflammation, autoimmune, cardiovascular, neuropsychiatric and endocrine disorders as well as cancer.

Histamine exerts its pleiotropic actions mainly through binding to four types of G-protein-coupled receptors (GPCRs), designated as H1-H4 that are differentially expressed in various cell types and exhibit considerable variations among species. The H2 receptor is responsible for gastric acid secretion; the H3 receptor controls the release of histamine and other neuromodulators in the CNS and the H1 receptor is associated with wakefulness and inflammatory response.

Identified in 2000, the high affinity H4 receptor displays constitutive activity and is expressed mostly, but not exclusively on cells of the immune system including mast cells, monocytes, dendritic cells, eosinophils, basophils, neutrophils, and T cells. This discovery led to the attractive prospect of a new drug target with therapeutic potential in acute and chronic inflammation, autoimmune disease, host defense and neuropathic pain.

The H4R shares only 40% homology with its nearest neighbour the H3R and neither H2 nor H1 antagonists were shown to inhibit histamine induced eosinophil chemotaxis. Histamine has been shown to inhibit forskolin-induced cAMP responses in a pertussis toxin (PTx)-sensitive manner, suggesting that H4R signals via heterotrimeric Gαi/o proteins. Transient expression of the H4R in heterologous cell systems (e.g. HEK293 cells) is a widely used method to measure H4 ligand signaling and binding to generate estimates of functional potency and receptor affinity respectively.

The discovery of H4R antagonists using these techniques and their study in various animal disease models including asthma, chronic pruritus, dermatitis, rheumatoid arthritis, gastric ulcerogenesis and colitis has confirmed H4R antagonism leads to a profound anti-inflammatory effect and has validated the therapeutic benefit for targeting this receptor. The first H4R antagonist phase 2a clinical trial in patients suffering from moderate-to-severe atopic dermatitis has already been conducted, further confirming H4 as a druggable target in patients Notwithstanding a number of published H4R ligands, there remains a need to develop new H4R antagonists with good drug candidate quality. These antagonists should display excellent low nM potency and affinity with full selectivity against H1-H3 receptors. They should display no agonist activity due to risks associated with the induction of pro-inflammatory responses, and ideally display a similar pharmacological profile across species to support PK/PD in various animal models of disease. They should be metabolically stable, with excellent PK, non-toxic and show excellent H4 specificity in broad safety panel profiling.

The human ether-a-go-go-related gene (hERG) encodes the pore-forming subunit of the rapidly activating delayed rectifier potassium channel (IKr), which plays an important role in ventricular repolarisation and in determining the QT-interval of the electrocardiogram with QT-interval being the time taken for ventricular depolarisation and repolarisation. It is widely acknowledged that hERG is highly susceptible to inhibition by a wide range of structurally diverse compounds. When the channels ability to conduct electrical current across the cell membrane is inhibited or compromised by application of drugs, it can result in a potentially fatal disorder called QT syndrome. A number of clinically successful drugs in the market have had the tendency to inhibit hERG, and create a concomitant risk of sudden death, as a side-effect, which has made hERG inhibition an important anti-target that must be avoided during drug development.

Compounds of the invention are antagonists of the H4 receptor. Certain compounds have a low hERG inhibition, making these particularly beneficial.

THE INVENTION

The present invention provides compounds having activity as H4 receptor antagonists. More particularly, the invention provides compounds that combine H4 receptor antagonism with low hERG activity.

Accordingly, in one embodiment the invention provides a compound of the formula (1)

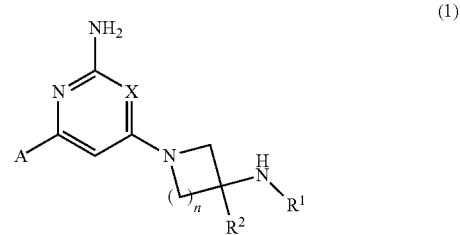

or a salt thereof, wherein;

X is CH or N;

n is 1 or 2;

R¹ is selected from H or $C_{1-3}$ alkyl, wherein the $C_{1-3}$ alkyl group may be cyclised back onto the ring to which NHR¹ is attached to form a second ring;

R² is H or methyl; and

A represents an optionally substituted pyrazole ring.

Ring A can represent an optionally substituted pyrazole ring which is linked to the ring containing X by a carbon-carbon bond.

Particular compounds include a compound of formula (Ia):

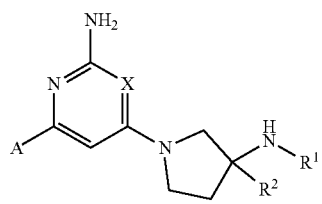
(1a)

or salts thereof, wherein A, X, R¹ and R² are as defined above.

Particular compounds also include compounds of formula (2a), (2b) and (2c):

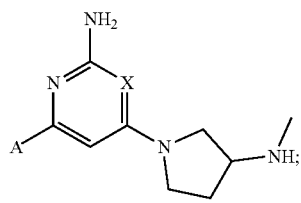
(2a)

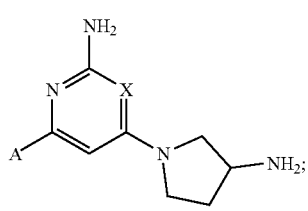
(2b)

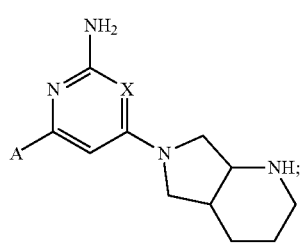
(2c)

or a salt thereof, wherein A and X are as defined above.

Particular isomers include compounds of formula (3a), (3b) and (3c):

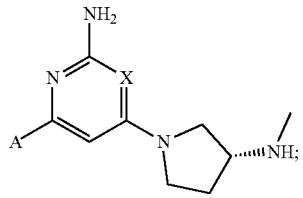
(3a)

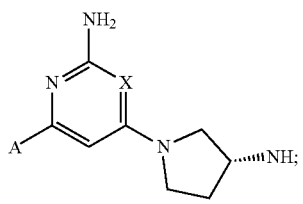
(3b)

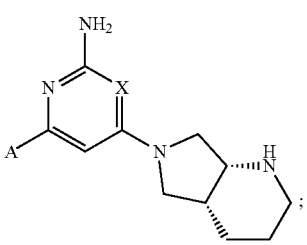
(3c)

or a salt thereof, wherein A and X are as defined above.

Particular compounds include a compound of formula (Ib):

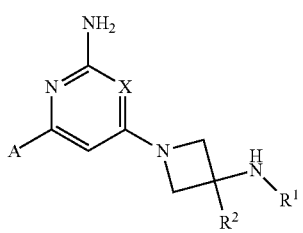
(1b)

or a salt thereof, wherein A, X, R¹ and R² are as defined above.

Particular compounds also include compounds of formula (2d) and (2e):

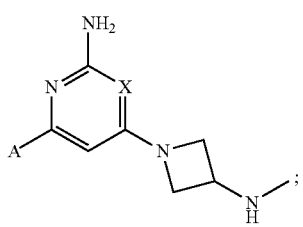
(2d)

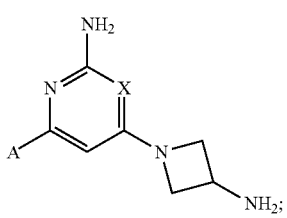

(2e)

or a salt thereof, wherein A and X are as defined above.

In the compounds herein, $R^1$ can be H or $C_{1-3}$ alkyl.

In the compounds herein, $R^1$ can be methyl, ethyl, propyl, isopropyl or cyclopropyl.

In the compounds herein, $R^1$ can be $C_{1-3}$ alkyl, wherein the $C_{1-3}$ alkyl group is cyclised back onto the ring to which $NHR^1$ is attached to form a second ring.

In the compounds herein, $R^2$ can be H or methyl.

Ring A represents an optionally substituted pyrazole ring.

Ring A may represent a ring selected from:

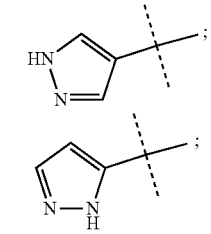

or a tautomer thereof.

Ring A may represent a ring selected from:

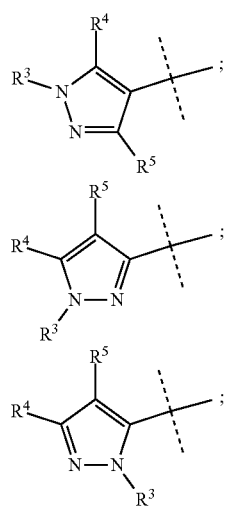

wherein $R^3$ is selected from H; a $C_{1-6}$ non-aromatic hydrocarbon group optionally substituted with 1 to 6 fluorine atoms; $(CH_2)_m R^6$, wherein m is 1 to 3 and $R^6$ is selected from CN, OH, $C_1$-$C_8$ alkoxy and a group $SR^8$ or oxidized forms thereof, wherein $R^8$ is $C_1$-$C_8$ alkyl; an optionally substituted 4 to 6 membered saturated heterocyclic ring containing 1 heteroatom selected from O and N, wherein the optional substituent is $CO_2R^7$, wherein $R^7$ is $C_{1-3}$ alkyl; wherein $R^4$ and $R^5$ are independently selected from: a $C_{1-6}$ non-aromatic hydrocarbon group optionally substituted with 1 to 6 fluorine atoms; $(CH_2)_p R^9$, wherein p is 0 to 3 and $R^9$ is selected from CN, halo, OH, $C_1$-$C_3$ alkoxy and a group $SR^8$ or oxidized forms thereof, wherein $R^8$ is $C_1$-$C_3$ alkyl; or $R^4$ and $R^5$ may be optionally joined to form a fused 5 or 6 membered ring; or $R^4$ and $R^3$ may be optionally joined to form a fused 5 or 6 membered ring.

The compounds may be used as H4 receptor antagonists. The compounds may be used in the manufacture of medicaments. The compounds or medicaments may be for use in treating, preventing, ameliorating, controlling or reducing the risk of inflammatory disorders including asthma, chronic pruritus, dermatitis, rheumatoid arthritis, gastric ulcerogenesis and colitis.

DESCRIPTION OF THE DRAWING

FIG. 1 shows a schematic of the QPatch voltage protocol used for the hERG assay.

DETAILED DESCRIPTION OF THE INVENTION

The invention relates to novel compounds. The invention also relates to the use of novel compounds as antagonists of the H4 receptor. The invention further relates to the use of novel compounds in the manufacture of medicaments for use as H4 receptor antagonists or for the treatment of H4 system dysfunction. The invention further relates to compounds, compositions and medicaments which are selective H4 receptor antagonists.

The invention further relates to compounds, compositions and medicaments useful for the treatment of acute and chronic inflammation, autoimmune disease, host defense disorders and neuropathic pain.

Compounds of the invention include compounds according to formula (1)

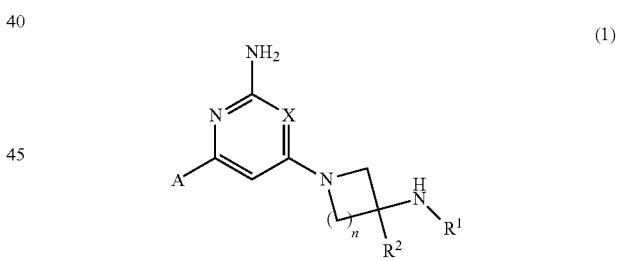

(1)

or a salt thereof, wherein;

X is CH or N;

n is 1 or 2;

$R^1$ is selected from H or $C_{1-3}$ alkyl, wherein the $C_{1-3}$ alkyl group may be cyclised back onto the ring to which $NHR^1$ is attached to form a second ring;

$R^2$ is H or methyl; and

A represents an optionally substituted pyrazole ring which is linked to the ring containing X by a carbon-carbon bond.

In the compounds herein X can be CH or N. X can be CH. X can be N.

In the compounds herein n can be 1 or 2. n can be 1. n can be 2.

In the compounds herein $R^1$ can be H or $C_{1-3}$ alkyl. The $C_{1-3}$ alkyl group may be cyclised back onto the ring to which $NHR^1$ is attached to form a second ring.

In the compounds herein $R^2$ can be H or methyl. $R^2$ can be H. $R^2$ can be methyl.

Exemplary compounds may include

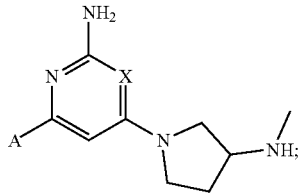

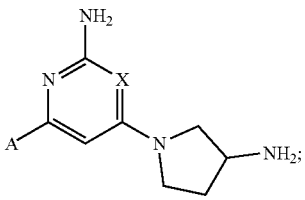

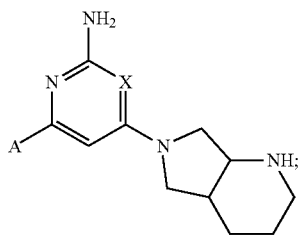

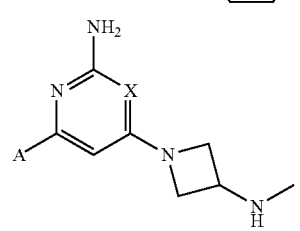

wherein A represents an optionally substituted pyrazole ring.

In the compounds herein A can be selected from:

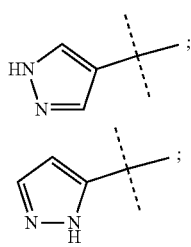

or a tautomer thereof.

Ring A may represent a ring selected from:

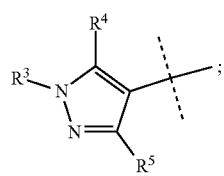

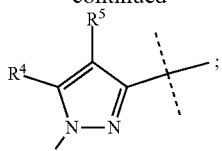

-continued

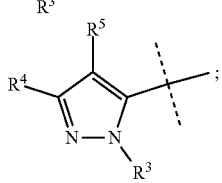

wherein $R^3$ is selected from H; a $C_{1-6}$ non-aromatic hydrocarbon group optionally substituted with 1 to 6 fluorine atoms; $(CH_2)_m R^6$, wherein m is 1 to 3 and $R^6$ is selected from CN, OH, $C_1$-$C_3$ alkoxy and a group $SR^8$ or oxidized forms thereof, wherein $R^8$ is $C_1$-$C_3$ alkyl; an optionally substituted 4 to 6 membered heterocyclic ring saturated heterocyclic ring containing 1 heteroatom selected from O and N, wherein the optional substituent is $CO_2R^7$, wherein $R^7$ is $C_{1-3}$ alkyl; wherein $R^4$ and $R^5$ are independently selected from: a $C_{1-6}$ non-aromatic hydrocarbon group optionally substituted with 1 to 6 fluorine atoms; $(CH_2)_p R^9$, wherein p is 0 to 3 and $R^9$ is selected from CN, halo, OH, $C_1$-$C_3$ alkoxy and a group $SR^8$ or oxidized forms thereof, wherein $R^8$ is $C_1$-$C_3$ alkyl; or $R^4$ and $R^5$ may be optionally joined to form a fused 5 or 6 membered ring; or $R^4$ and $R^3$ may be optionally joined to form a fused 5 or 6 membered ring.

Particular substituents for ring A include one or more of methyl, ethyl, isopropyl, difluoromethyl, trifluoromethyl, 1,1,1-trifluoroethyl, 1-hydroxyethyl, cyclopropyl, cyclobutyl, fluoro, chloro, bromo, cyano, hydroxyl, methoxy, thiomethyl, 1-methyoxyethyl, cyanomethyl, 1-cyanoethyl, oxetane, piperidine or a fused ring. The fused ring can be a 6 membered aromatic ring. The fused ring can be a 5 or 6 membered aliphatic ring. The piperidine substituent may be 3 N-ethyl carboxylate. Where A is substituted with two or three groups, each substituent may be the same or different.

In the compounds herein $R^3$ can be selected from H, methyl, $CF_3$, $CF_2H$, ethyl, cyclopropyl, cyclobutyl, $CH_2CF_3$, $CH_2CH_2OH$, $CH_2CH_2OCH_3$, $CH_2CH_2CN$, $CH_2CN$, oxetane, ethyl-piperidine-carboxylate or $R^4$ and $R^3$ can be joined to form a fused 5 membered ring. $R^4$ and $R^3$ can be joined to form a fused 5 membered aliphatic ring.

In the compounds herein $R^4$ or $R^5$ can be selected from methyl, ethyl, cyclopropyl, cyclobutyl, propyl, isopropyl, $CF_3$, $CF_2H$, fluoro, chloro, bromo, cyano, hydroxy, methoxy, thiomethyl or $R^4$ and $R^5$ are joined to form a fused 5 or 6 membered ring. $R^4$ and $R^5$ can be joined to form a fused 5 or 6 membered aliphatic or aromatic ring. $R^4$ and $R^5$ can be joined to form a fused 5 or 6 membered aliphatic ring. $R^4$ and $R^5$ can be joined to form a fused 5 or 6 membered aromatic ring.

In the compounds herein A can be selected from the group consisting of:

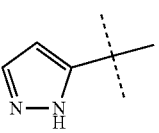 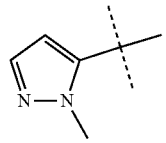

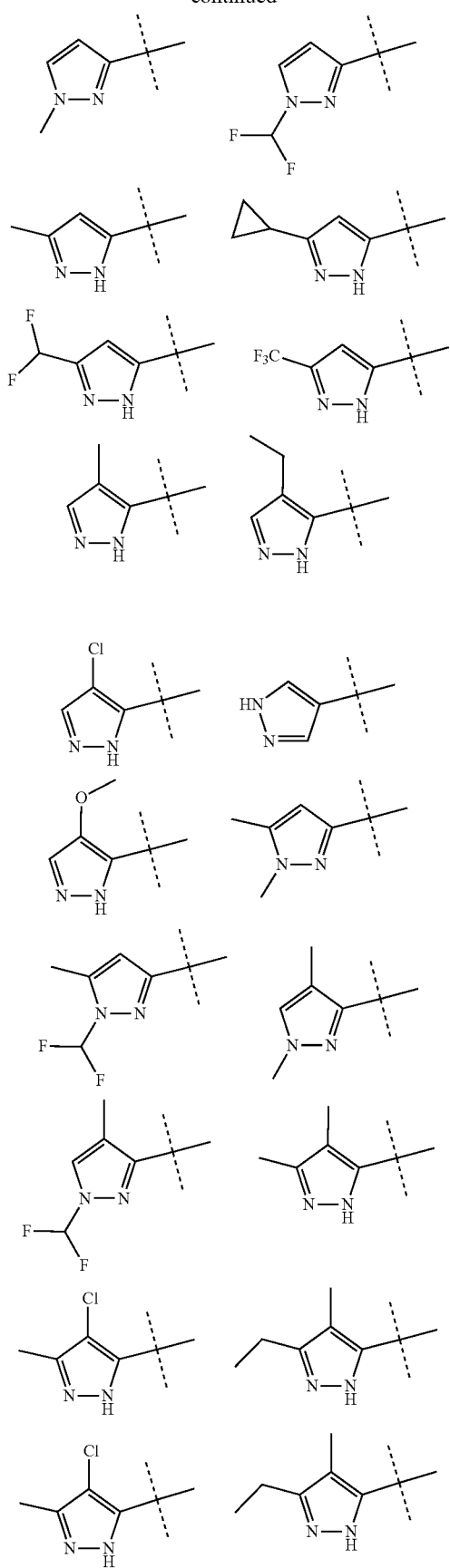
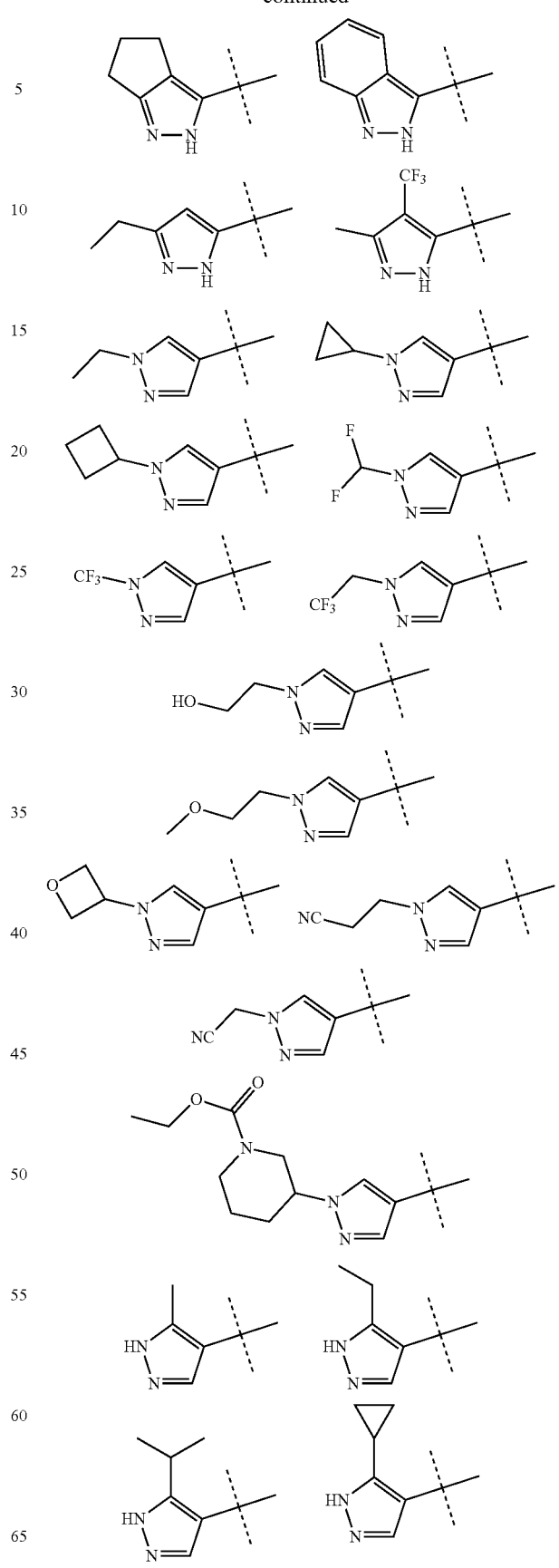

-continued
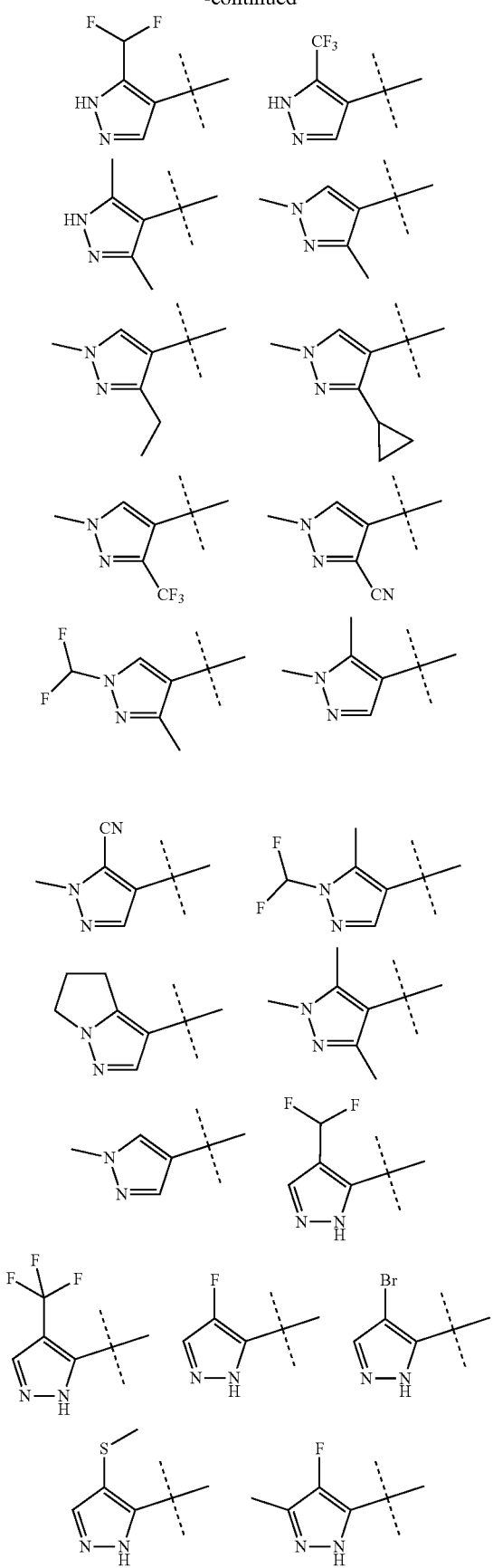
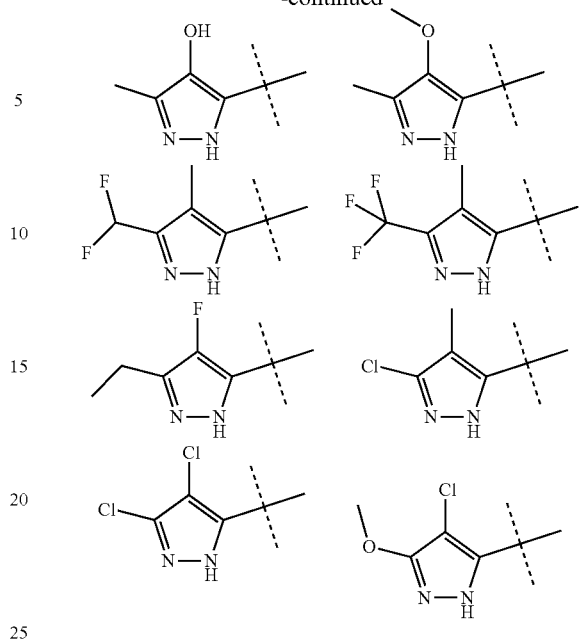
Exemplary compounds may include
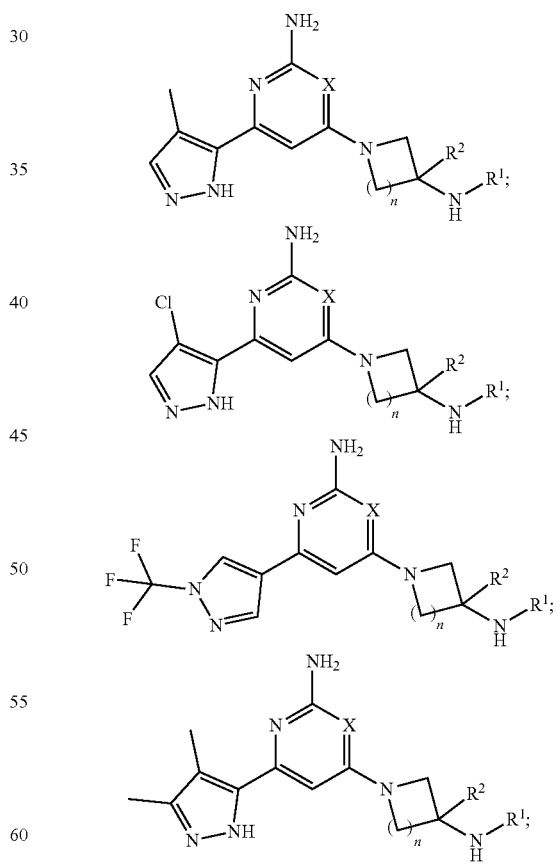
wherein n is 1 or 2;
R[1] is selected from H or $C_{1-3}$ alkyl, wherein the $C_{1-3}$ alkyl group may be cyclised back onto the ring to which NHR[1] is attached to form a second ring; and
R[2] is H or methyl.

The compound can be selected from the group consisting of:
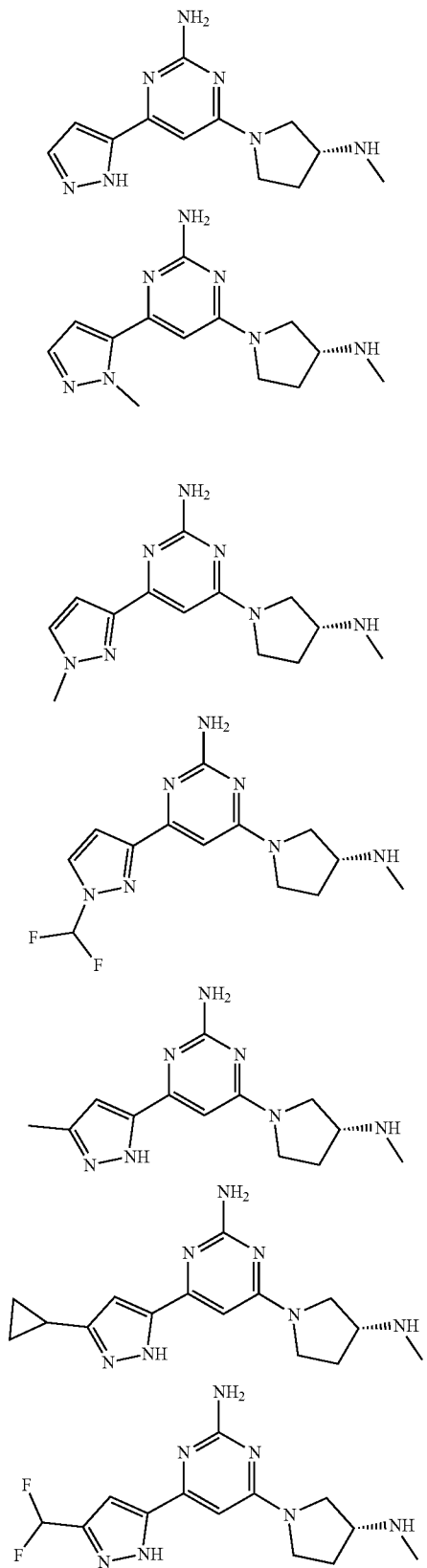
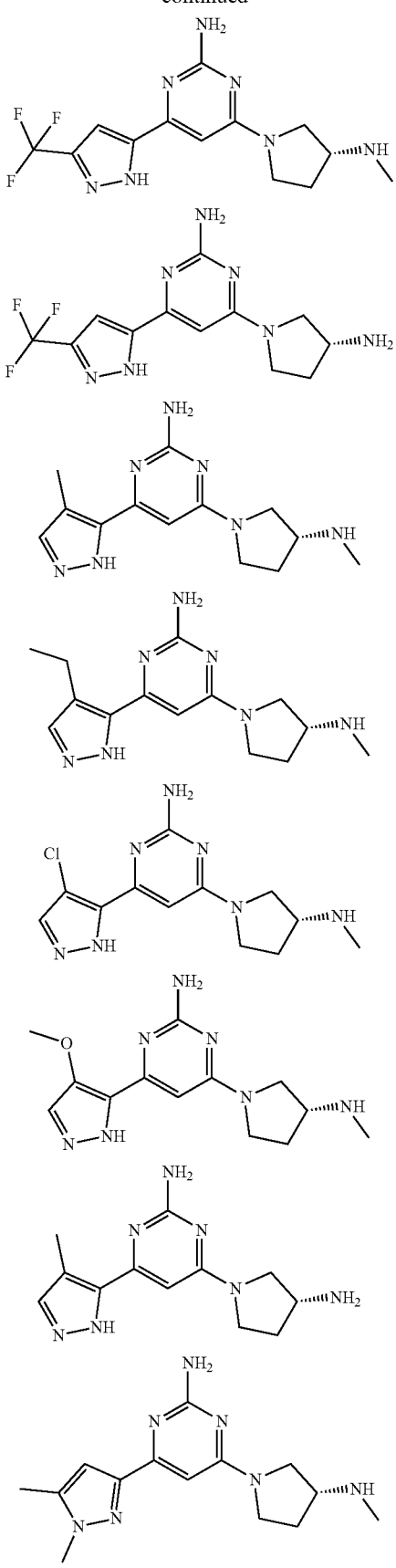

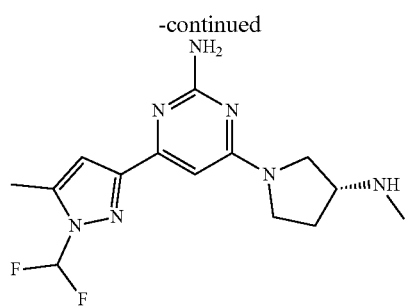
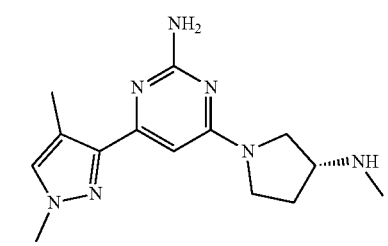
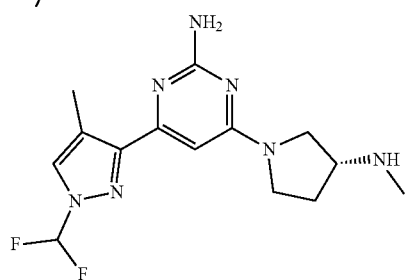
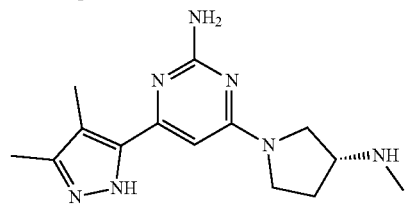
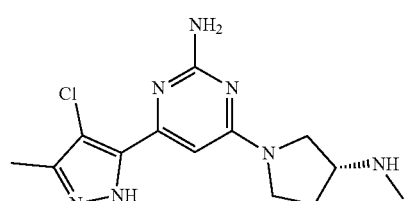
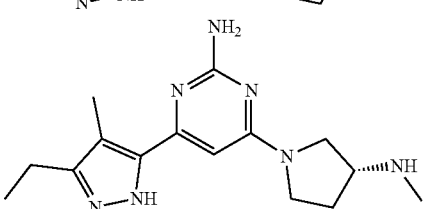
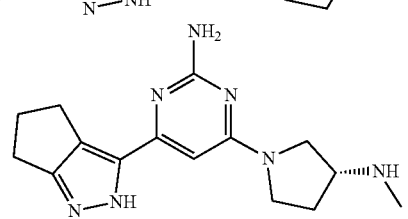
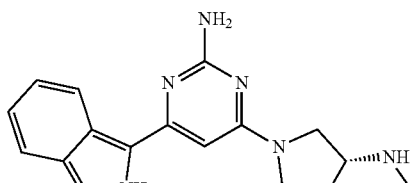
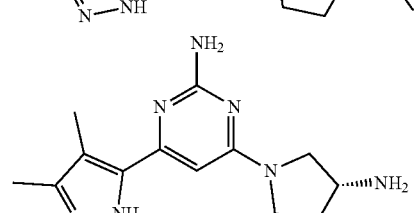
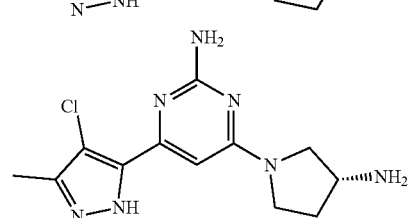
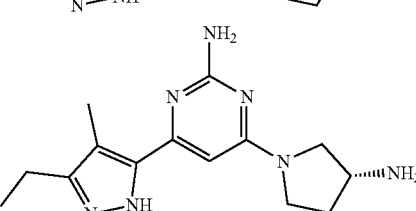
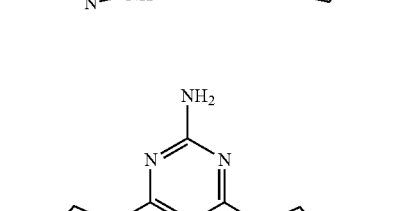
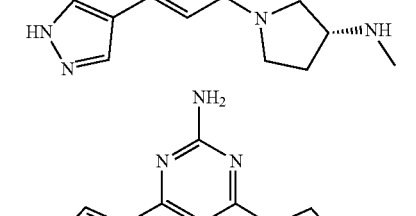
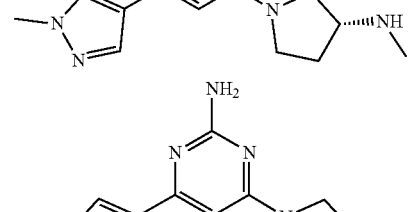
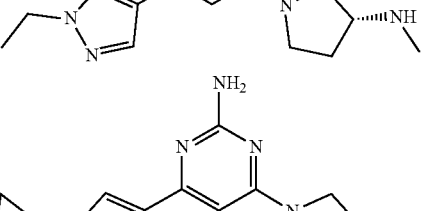

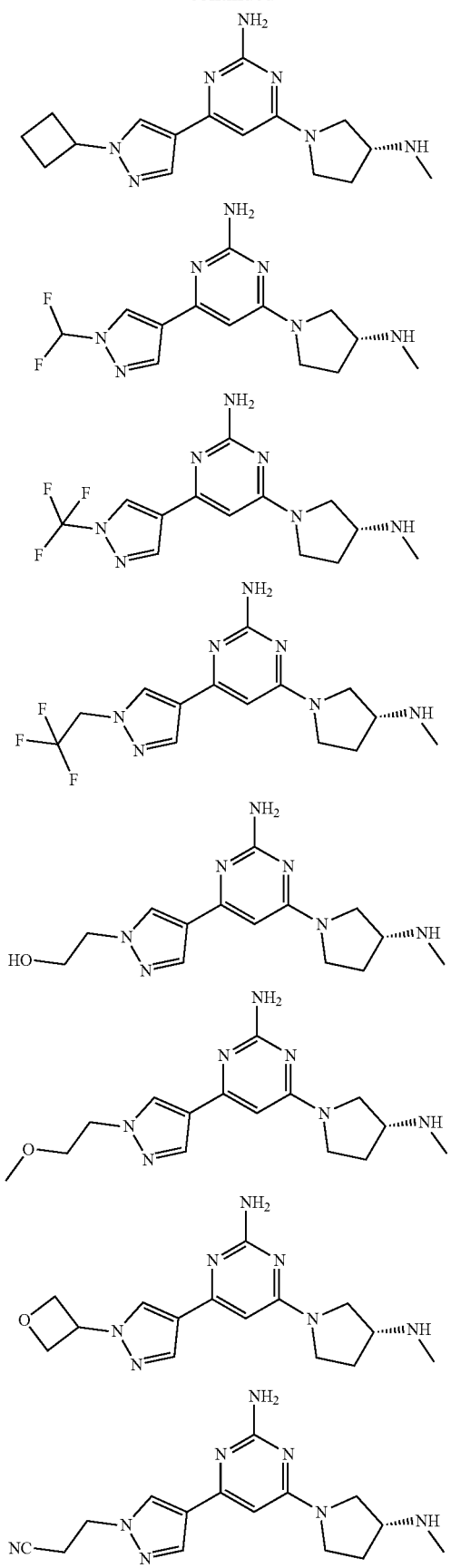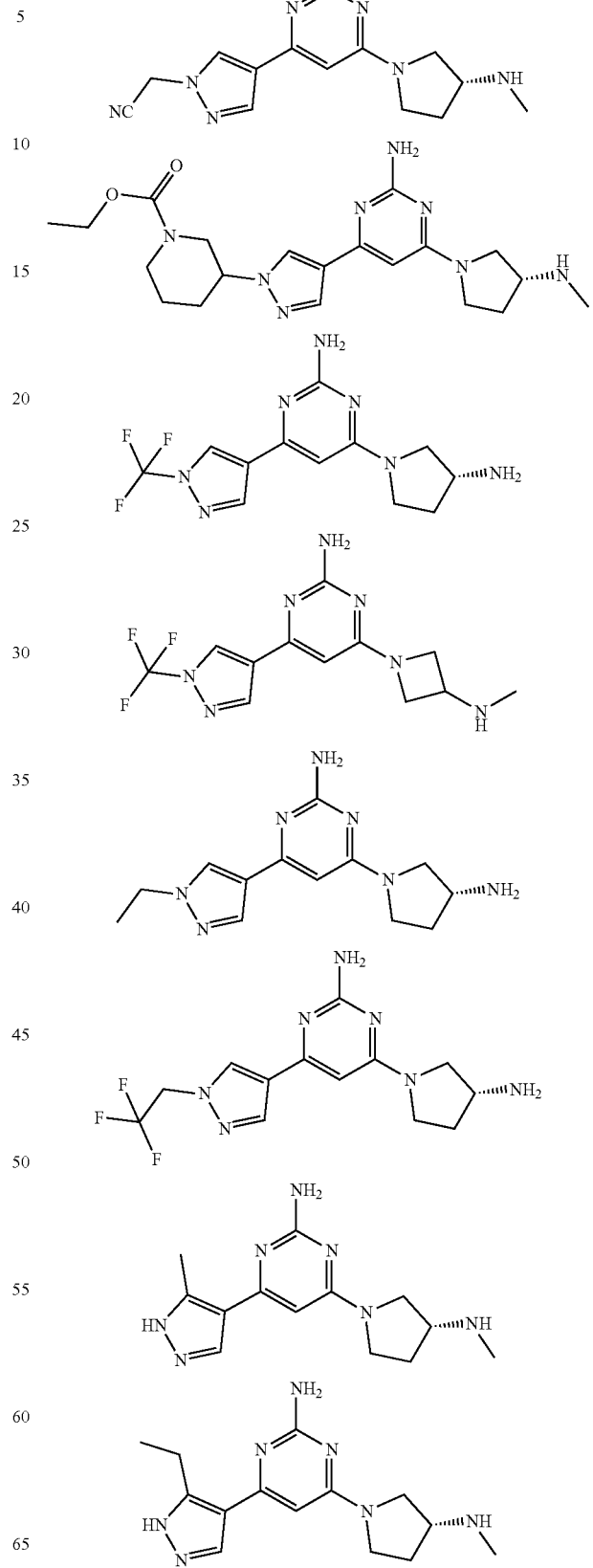

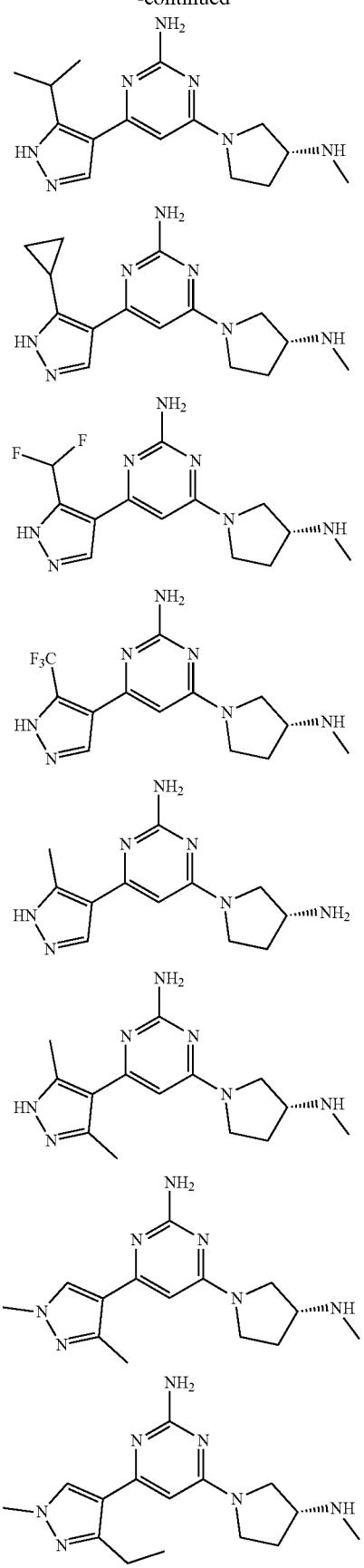
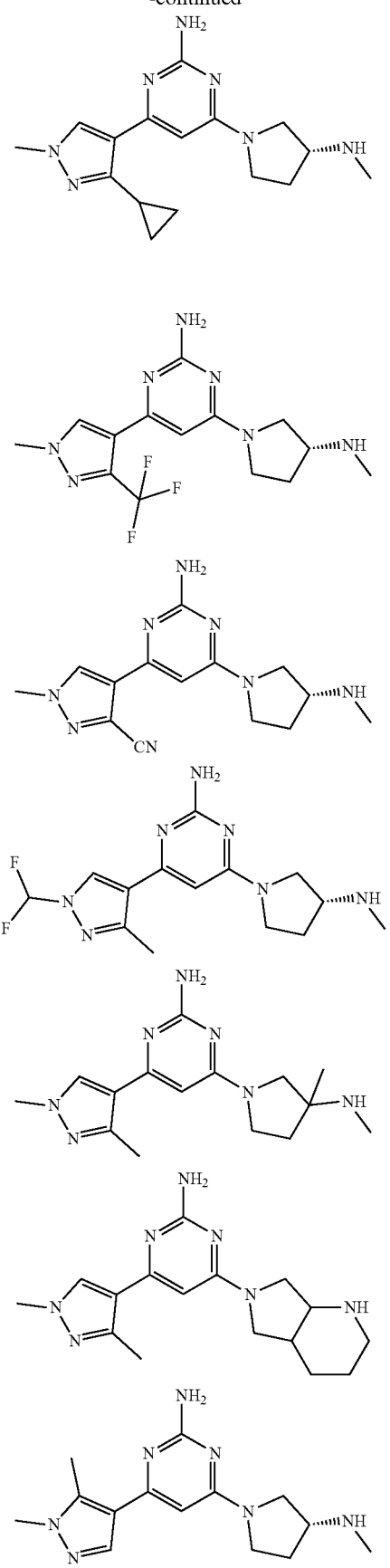

-continued
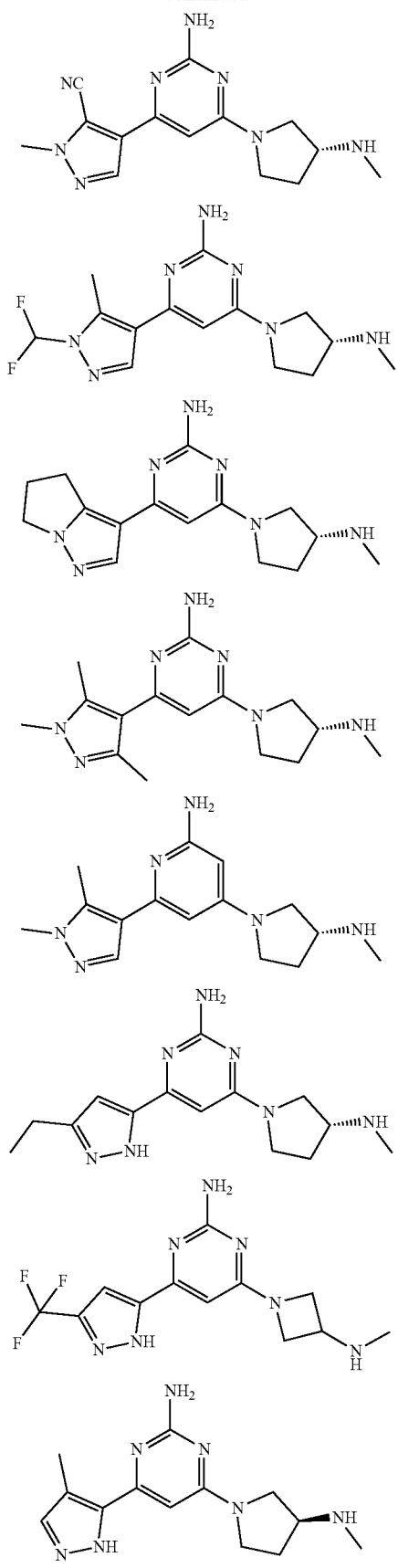
-continued
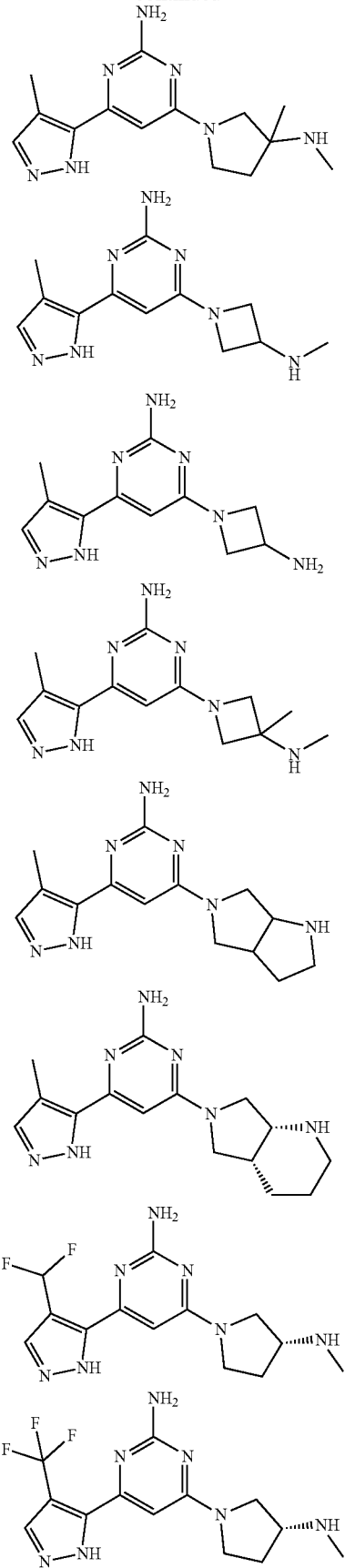

-continued
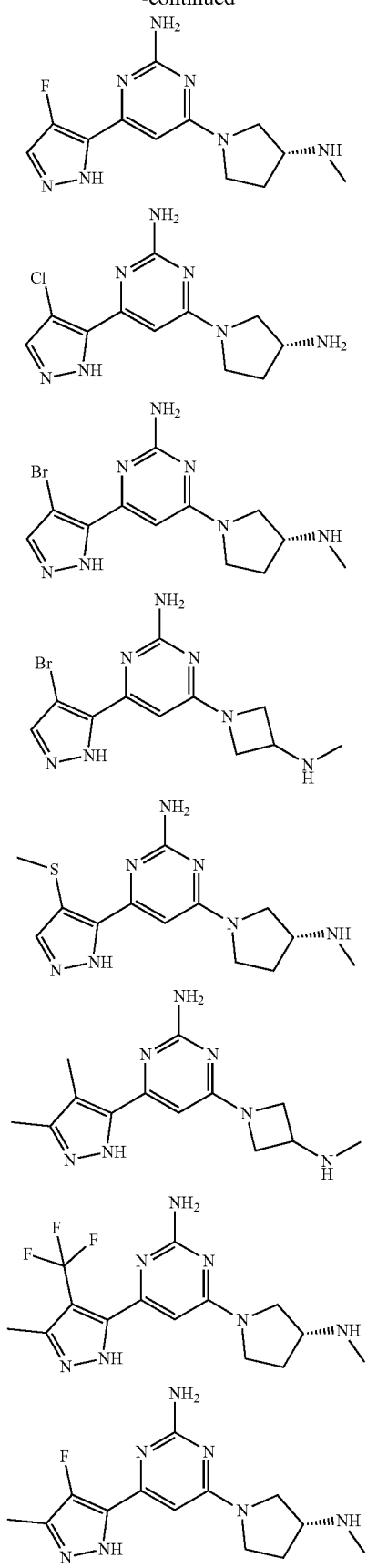
-continued
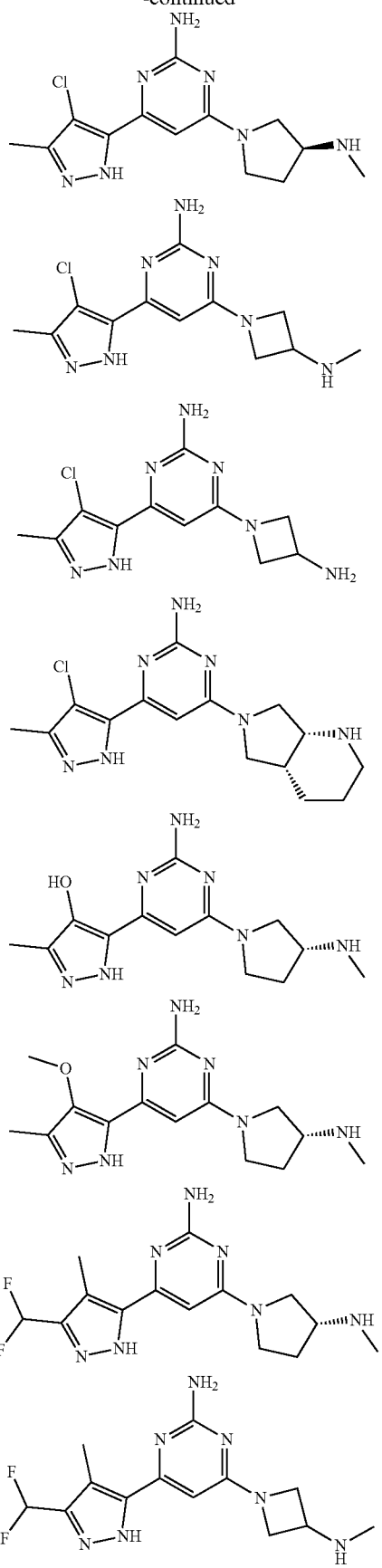

-continued

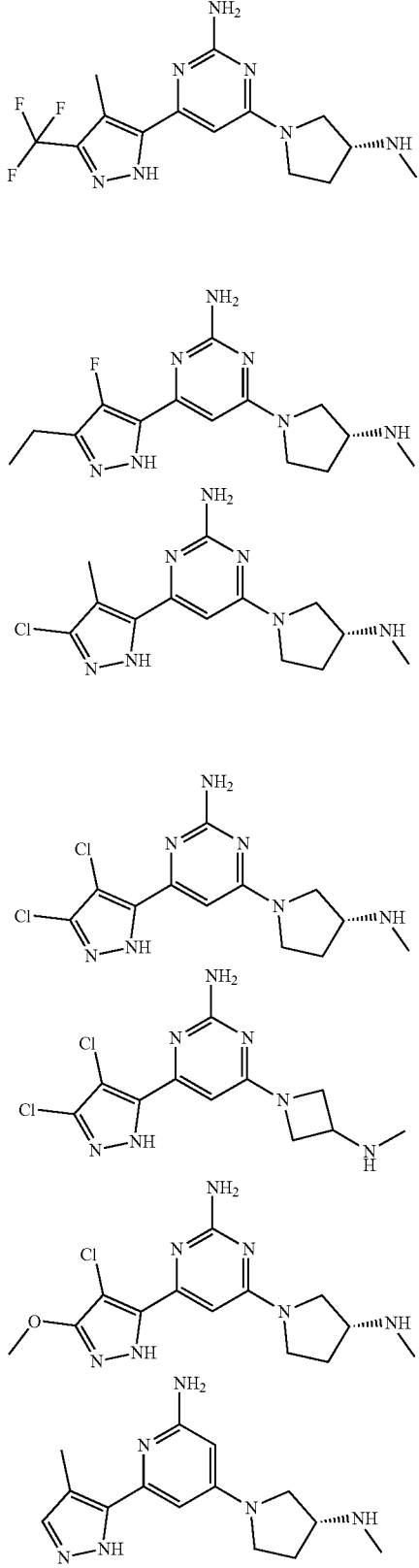

and salts thereof.

Specific examples of compounds include those having low hERG activity.

Particular compounds include:

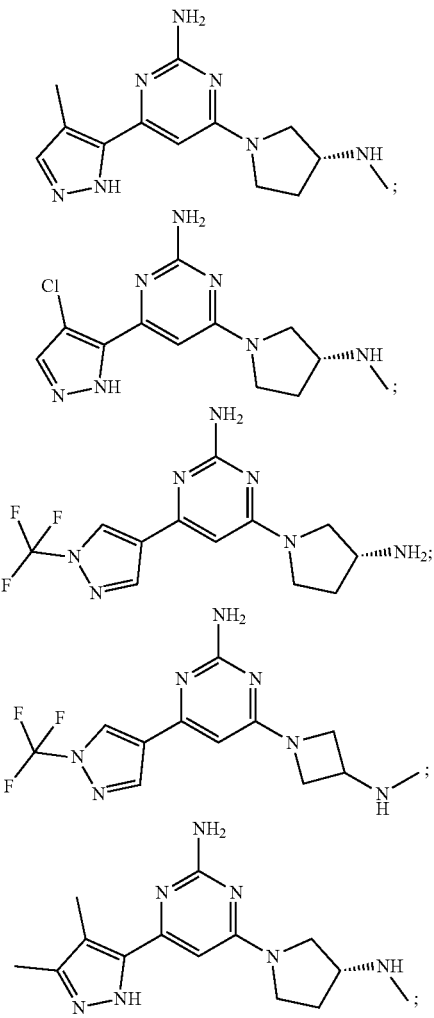

Definitions

In this application, the following definitions apply, unless indicated otherwise.

The term "treatment", in relation to the uses of any of the compounds described herein, including those of the formula (1) or formula (1a), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disease or condition) refers to an amount of the compound which is effective to produce a desired therapeutic effect. For example, if the condition is pain, then the effective therapeutic amount is an amount sufficient to provide a desired level of pain relief. The desired level of pain relief may be, for example, complete removal of the pain or a reduction in the severity of the pain.

The term "non-aromatic hydrocarbon group" as in "$C_{1-6}$ non-aromatic hydrocarbon group" refers to a group consisting of carbon and hydrogen atoms and which contains no aromatic rings. The hydrocarbon group may be fully saturated or may contain one or more carbon-carbon double bonds or carbon-carbon triple bonds, or mixtures of double and triple bonds. The hydrocarbon group may be a straight chain or branched chain group or may consist of or contain a cyclic group. Thus the term non-aromatic hydrocarbon includes alkyl, alkenyl, alkynyl, cycloalkyl, cycloalkenyl, cycloalkylalkyl, cycloalkenyl alkyl and so on.

The term "saturated" refers to a hydrocarbon group containing no carbon-carbon double bonds or triple bonds. The saturated hydrocarbon group can therefore be an alkyl group, a cycloalkyl group, a cycloalkylalkyl group, an alkylcycloalkyl group or an alkylcycloalkylalkyl group. Examples of saturated hydrocarbon groups include cyclopropyl, cyclobutyl and cyclopropylmethyl.

Examples of 4 to 6 membered saturated heterocyclic rings containing 1 heteroatom selected from O and N include oxetane, azetidine, tetrahydrofuran, pyrollidine, tetrahydropyran and piperidine.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (+)-DL-lactic), lactobionic, maleic, malic (e.g. (−)-L-malic), malonic, (+)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 µg to about 30 mg per kg body weight of a human and non-human animal, preferably from about 50 µg to about 30 mg per kg of body weight of a human and non-human animal, for example from about 50 µg to about 10 mg per kg of body weight of a human and non-human animal, for example from about 100 µg to about 30 mg per kg of body weight of a human and non-human animal, for example from about 100 µg to about 10 mg per kg of body weight of a human and non-human animal and most preferably from about 100 µg to about 1 mg per kg of body weight of a human and non-human animal.

Methods for the Preparation of Compounds of the Formula (1)

Compounds of the formula (1) can be prepared in accordance with synthetic methods well known to the skilled person and as described herein. Accordingly, in another embodiment, the invention provides a process for the preparation of a compound as defined in formula (1) above, which process comprises:

(A) the reaction of a compound of the formula (10):

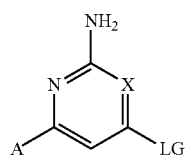

(10)

with a compound of the formula (11):

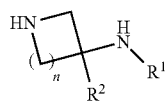

(11)

under SNAr conditions or transition metal catalyzed coupling conditions; wherein A, $R^1$, $R^2$, X, and n are as defined in formula (1) above, and LG represents a suitable leaving group; or (B) the reaction of a compound of the formula (12):

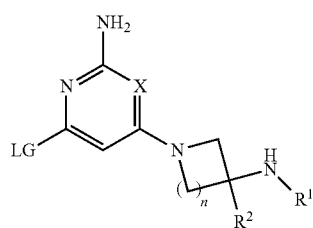

(12)

with a compound of the formula (13):

$$A\text{-}M \qquad (13)$$

under transition metal catalyzed coupling conditions or under SNAr conditions; wherein A, $R^1$, $R^2$, X and n are as defined in formula (1) above, LG represents a suitable leaving group and M, which may be present or absent, represents a suitably substituted metal or non-metal; or (C) converting one compound of the formula (1) to another compound of the formula (1).

In process variant (A), the compound of formula (10) may be reacted with the compound of formula (11) under SNAr conditions. The SNAr reaction is typically carried out using either an excess of the compound of formula (11), or a stoichiometric quantity of the compound of formula (11) in the presence of a base which may be a tertiary amine base such as TEA or DIPEA or an inorganic base such as $K_2CO_3$, $Cs_2CO_3$ or $NaHCO_3$, optionally in a suitable solvent such as $H_2O$, MeCN, 1,4-dioxane, THF, MeOH, EtOH, IPA, BuOH, DMF, NMP or DMSO, or a combination of suitable solvents, at a temperature between about room temperature to about 200° C., using conventional heating or optionally by heating with microwave irradiation, in an open vessel or optionally in a sealed vessel, optionally at a pressure greater than atmospheric pressure, optionally in the presence of an additive such as KF or a silver salt. Optionally, the compound of formula (11) may be present in the reaction as an acid salt such as an HCl, HBr or a TFA salt optionally in the presence of a tertiary base such as TEA or DIPEA. The leaving group LG in the compound of formula (10) may be a halogen such as F, Cl or Br; an alkoxy group such as OMe; an aryloxy group such as pentafluorophenoxy; a sulfenyl group such as SMe, a sulfinyl group such as SOMe, a sulfonyl group such as $SO_2Me$, a sulfonyloxy group such as OTs, OMs, ONs or OTf; or a leaving group generated by reaction of a hydroxy group with a peptide coupling reagent such as BOP, PyBOP or HATU.

Alternatively, in process variant (A), the compound of formula (10) may be reacted with the compound of formula (11) under transition metal catalyzed coupling conditions. The transition metal catalyzed coupling reaction is typically carried out using the compound of formula (11) in the presence of an inorganic base such as $NaO^tBu$, $KO^tBu$, $K_3PO_4$, $K_2CO_3$ or $Cs_2CO_3$, in a suitable solvent such as 1,4-dioxane, THF, DME or toluene, or a combination of suitable solvents, in the presence of a sub-stoichiometric quantity of a transition metal catalyst such as $Pd(OAc)_2$, $Pd_2(dba)_3$, $Pd(dppf)Cl_2$, $Pd(PPh_3)_2Cl_2$ or $Pd(PPh_3)_4$, optionally in the presence of a sub-stoichiometric quantity of a phosphine ligand such as $PPh_3$, $PBu_3$, $P^tBu_3$, XPhos, Xantphos or BINAP, at a temperature between about room temperature to about 200° C., using conventional heating or optionally by heating with microwave irradiation, in an open vessel or optionally in a sealed vessel, optionally at a pressure greater than atmospheric pressure. The leaving group LG in the compound of formula (10) may be a halogen such as Cl, Br or I, or a sulfonyloxy group such as OTs, OMs, ONs or OTf.

Compounds of formula (10) can be prepared by the reaction shown in Scheme 1 below:

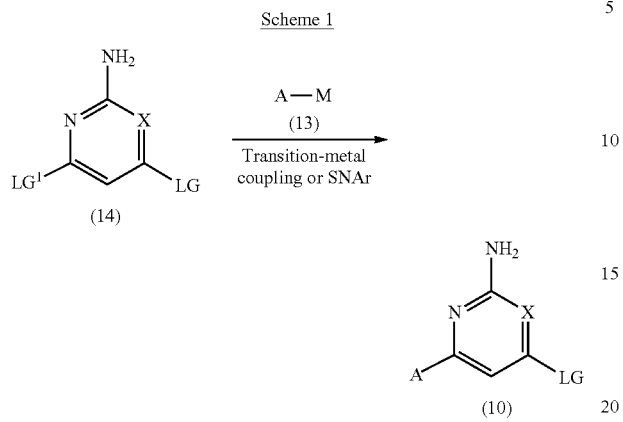

Scheme 1

(14) → (10)

Thus, a compound of formula (14), wherein X is as defined in formula (1) above, and LG and LG¹ may be the same or different and represent suitable leaving groups, may be reacted with a compound of formula (13), wherein A is as defined in formula (1) above, and M, which may be present or absent, represents a suitably substituted metal or non-metal, under transition metal catalyzed coupling conditions or under SNAr conditions to form a compound of formula (10). The transition metal catalyzed coupling reaction or the SNAr reaction is typically carried out as described below in process variant (B), and the compounds of formula (13) and formula (14) may be commercially available or easily prepared by standard methods reported in the published literature from simple starting materials known to the skilled person. Occasionally, due to their instability, it may be necessary to generate compounds of formula (13), where M is present, in-situ at low temperatures, e.g. between about −78° C. and room temperature, and react them further in a transition metal catalyzed coupling reaction, without their prior isolation. Details of such methods are known in the published literature, e.g. as reported by Oberli and Buchwald in Org. Lett., 2012, Vol. 14, No. 17, p 4606.

Alternatively, compounds of formula (10), wherein X represents N and LG represents Cl, can be typically prepared by the sequence of reactions shown in Scheme 2 below:

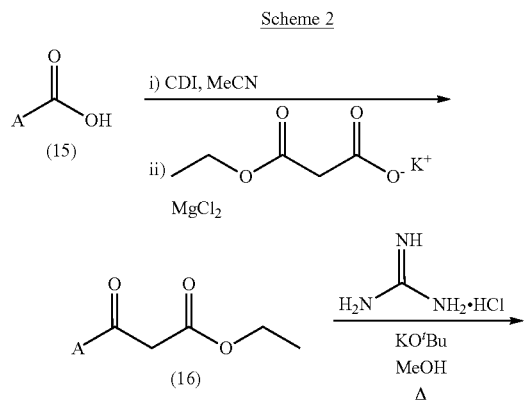

Scheme 2

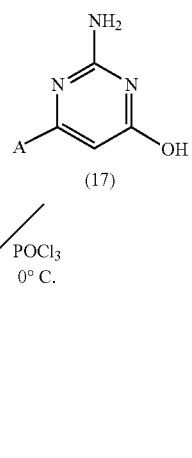

Thus, a carboxylic acid of formula (15) may be homologated to the corresponding beta-keto ester (16) by first activating it via a number of standard methods known to the skilled person, e.g. by reaction with CDI in a suitable solvent such as MeCN, and then reacting with a malonic acid derivative such as potassium 3-ethoxy-3-oxopropanoate in the presence of a Lewis acid such as $MgCl_2$. Once formed, the beta-keto ester (16) may be cyclised to the amino-hydroxypyrimidine analogue (17) by reaction with guanidine, or an appropriate guanidine salt, in the presence of a suitable base such as KO$^t$Bu in a suitable solvent such as MeOH. The amino-hydroxypyrimidine analogue (17) so formed may then be reacted with $POCl_3$ in the presence or absence of a suitable solvent to form a compound of formula (18). Compounds of formula (15) may be commercially available or easily prepared by standard methods reported in the published literature from simple starting materials known to the skilled person.

Compounds of formula (11) may be commercially available or easily prepared by standard methods reported in the published literature from simple starting materials known to the skilled person.

In process variant (B), the compound of formula (12) may be reacted with the compound of formula (13) under transition metal catalyzed coupling conditions. The transition metal catalyzed coupling reaction is typically carried out using the compound of formula (13) wherein M is present. For example, when M represents a boronic acid —B(OH)$_2$, or a boronic ester such as —B(OMe)$_2$, —B(OiPr)$_2$ or Bpin, or a lithium trialkylborate such as —B(OiPr)$_3$Li, then the transition metal catalyzed coupling reaction is typically carried out in the presence of an inorganic base such as $NaHCO_3$, $Na_2CO_3$, $K_2CO_3$, $Cs_2CO_3$ or $K_3PO_4$, in a suitable solvent such as $H_2O$, MeCN, 1,4-dioxane, THF, $Et_2O$, DME, EtOH, IPA, DMF, NMP or toluene, or a combination of suitable solvents, in the presence of a sub-stoichiometric quantity of a transition metal catalyst such as Pd(OAc)$_2$, Pd$_2$(dba)$_3$, Pd(dppf)Cl$_2$, Pd(PPh$_3$)$_2$Cl$_2$, Pd(PPh$_3$)$_4$, or a transition metal pre-catalyst such as XPhos Pd G2, optionally in the presence of a sub-stoichiometric quantity of a phosphine ligand such as PPh$_3$, P$^t$Bu$_3$, PCy$_3$ or XPhos, at a temperature between about room temperature to about 200° C., using conventional heating or optionally by heating with microwave irradiation, in an open vessel or optionally in a sealed vessel, optionally at a pressure greater than atmospheric pressure. The leaving group LG in the compound of formula

(12) may be a halogen such as Cl, Br or I, or a sulfonyloxy group such as OTs, OMs or OTf.

Alternatively, when M represents a trifluoroborate salt BF3, then the transition metal catalyzed coupling reaction is typically carried out in the presence of an inorganic base such as $Na_2CO_3$, $K_2CO_3$, $Cs_2CO_3$ or $K_3PO_4$, in a suitable solvent such as $H_2O$, MeCN, 1,4-dioxane, THF, MeOH or EtOH, or a combination of suitable solvents, in the presence of a sub-stoichiometric quantity of a transition metal catalyst such as $Pd(OAc)_2$, $Pd_2(dba)_3$, optionally in the presence of a sub-stoichiometric quantity of a phosphine ligand such as $PPh_3$, $PCy_3$ or RuPhos at a temperature between about room temperature to about 200° C., using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I.

Alternatively, when M represents a trialkyltin group such as $SnMe_3$ or $SnBu_3$, then the transition metal catalyzed coupling reaction is typically carried out in a suitable solvent such 1,4-dioxane, THF, DMF, or toluene, or a combination of suitable solvents, in the presence of a sub-stoichiometric quantity of a transition metal catalyst such as $Pd(OAc)_2$, $Pd_2(dba)_3$, $Pd(PPh_3)_2Cl_2$ or $Pd(PPh_3)_4$, optionally in the presence of an inorganic base such as $K_2CO_3$ or CsF, optionally in the presence of an additive such as LiCl, CuI, $Bu_4NBr$ or $Et_4NCl$, at a temperature between about room temperature to about 200° C., using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I.

Alternatively, when M is absent, then the transition metal catalyzed coupling reaction is typically carried out in the presence of an inorganic base such as $NaO^tBu$, $KO^tBu$, $K_3PO_4$, $K_2CO_3$ or $Cs_2CO_3$, in a suitable solvent such as 1,4-dioxane, THF, DME or toluene, or a combination of suitable solvents, in the presence of a sub-stoichiometric quantity of a transition metal catalyst such as $Pd(OAc)_2$, $Pd_2(dba)_3$, $Pd(dppf)Cl_2$, $Pd(PPh_3)_2Cl_2$ or $Pd(PPh_3)_4$, optionally in the presence of a sub-stoichiometric quantity of a phosphine ligand such as $PPh_3$, $PBu_3$, $PtBu_3$, XPhos, Xantphos or BINAP, at a temperature between about room temperature to about 200° C., using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I, or a sulfonyloxy group such as OTs, OMs, ONs or OTf.

Alternatively, when M is absent, then the transition metal catalyzed coupling reaction is typically carried out in the presence of an inorganic base such as $K_3PO_4$, $K_2CO_3$ or $Cs_2CO_3$, in a suitable solvent such as 1,4-dioxane, DMF, DMSO or toluene, or a combination of suitable solvents, in the presence of a sub-stoichiometric quantity of a transition metal catalyst such as CuI, optionally in the presence of a sub-stoichiometric quantity of an amine such as (S)-proline or trans-$N^1,N^2$-dimethylcyclohexane-1,2-diamine at a temperature between about room temperature to about 200° C., using conventional heating or optionally by heating with microwave irradiation, in an open vessel or optionally in a sealed vessel, optionally at a pressure greater than atmospheric pressure. The leaving group LG in the compound of formula (12) may be a halogen such as Cl, Br or I.

Alternatively, when M is absent, then the transition metal catalyzed coupling reaction is typically carried out in the presence of an organic base such as $nBu_4OAc$, in a suitable solvent such as 1,4-dioxane, in the presence of a sub-stoichiometric quantity of a transition metal pre-catalyst such as XPhos Pd G2, optionally in the presence of a sub-stoichiometric quantity of a phosphine ligand such as XPhos, at a temperature between about room temperature to about 200° C., using conventional heating or optionally by heating with microwave irradiation, in an open vessel or optionally in a sealed vessel, optionally at a pressure greater than atmospheric pressure. The leaving group LG in the compound of formula (12) may be a halogen such as Cl.

Alternatively, in process variant (B), the compound of formula (12) may be reacted with the compound of formula (13) under SNAr conditions. The SNAr reaction is typically carried out using the compound of formula (13) wherein M is absent, in the presence of a tertiary amine base such as TEA or DIPEA or an inorganic base such as $K_2CO_3$, $Cs_2CO_3$, $KO^tBu$, or NaH in a suitable solvent such as THF, DMF, H2O, DMSO or NMP, or a combination of suitable solvents, at a temperature between about room temperature to about 200° C., using conventional heating or optionally by heating with microwave irradiation, in an open vessel or optionally in a sealed vessel, optionally at a pressure greater than atmospheric pressure. The leaving group LG in the compound of formula (12) may be a halogen such as F, Cl or Br; an alkoxy group such as OMe; an aryloxy group such as pentafluorophenoxy; a sulfenyl group such as SMe, a sulfinyl group such as SOMe, a sulfonyl group such as $SO_2Me$, or a sulfonyloxy group such as OTs, OMs, ONs or OTf.

The compound of formula (12) can be prepared by the sequence of reactions shown in Scheme 3 below:

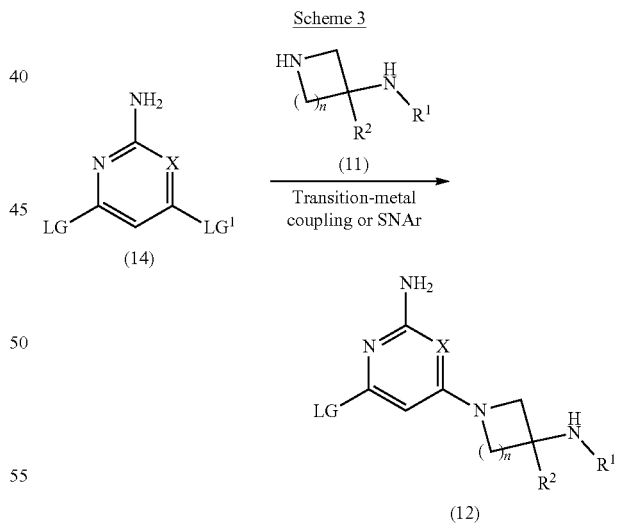

Scheme 3

Thus, a compound of formula (14), wherein X is as defined in formula (1) above, and LG and $LG^1$ may be the same or different and represent suitable leaving groups, may be reacted with a compound of formula (11), wherein $R^1$, $R^2$ and n are as defined in formula (1) above, under SNAr conditions or under transition metal catalyzed coupling conditions to form a compound of formula (12). The SNAr reaction or the transition metal catalyzed coupling reaction is typically carried as described above in process variant (A).

In process variant (C), one compound of the formula (1) can be converted into another compound of the formula (1) by methods well known to the skilled person. Examples of synthetic procedures for converting one functional group into another functional group are set out in standard texts such as *March's Advanced Organic Chemistry: Reactions, Mechanisms, and Structure,* 7th Edition, Michael B. Smith, John Wiley, 2013, (ISBN: 978-0-470-46259-1), *Organic Syntheses,* Online Edition, www.orgsyn.org, (ISSN 2333-3553) and *Fiesers' Reagents for Organic Synthesis,* Volumes 1-17, John Wiley, edited by Mary Fieser (ISBN: 0-471-58283-2).

In many of the reactions described above, it may be necessary to protect one or more groups to prevent reaction from taking place at an undesirable location on the molecule. Examples of protecting groups, and methods of protecting and deprotecting functional groups, can be found in *Greene's Protective Groups in Organic Synthesis,* Fifth Edition, Editor: Peter G. M. Wuts, John Wiley, 2014, (ISBN: 9781118057483). In particular, a useful protecting group for manipulating compounds of formula (10) or formula (12) includes the 2,5-dimethyl-1H-pyrrole group; useful protecting groups for manipulating compounds of formula (11) or formula (12) include BOC and CBZ; and useful protecting groups for manipulating compounds of formula (13) include SEM and THP.

Compounds made by the foregoing methods may be isolated and purified by any of a variety of methods well known to those skilled in the art and examples of such methods include recrystallisation and chromatographic techniques such as column chromatography (e.g. flash chromatography), HPLC and SFC.

Pharmaceutical Formulations

While it is possible for the active compound to be administered alone, it is preferable to present it as a pharmaceutical composition (e.g. formulation).

Accordingly, in another embodiment of the invention, there is provided a pharmaceutical composition comprising at least one compound of the formula (1) as defined above together with at least one pharmaceutically acceptable excipient.

The composition may be a tablet composition.

The composition may be a capsule composition.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes), binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

The pharmaceutical compositions typically comprise from approximately 1% (w/w) to approximately 95%, preferably % (w/w) active ingredient and from 99% (w/w) to 5% (w/w) of a pharmaceutically acceptable excipient (for example as defined above) or combination of such excipients. Preferably, the compositions comprise from approximately 20% (w/w) to approximately 90% (w/w) active ingredient and from 80% (w/w) to 10% of a pharmaceutically excipient or combination of excipients. The pharmaceutical compositions comprise from approximately 1% to approximately 95%, preferably from approximately 20% to approximately 90%, active ingredient.

Pharmaceutical compositions according to the invention may be, for example, in unit dose form, such as in the form of ampoules, vials, suppositories, pre-filled syringes, dragées, powders, tablets or capsules.

Tablets and capsules may contain, for example, 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition typically contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The pharmaceutical formulations may be presented to a patient in "patient packs" containing an entire course of treatment in a single package, usually a blister pack.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1-1 to 18-1

The compounds of Examples 1-1 to 18-1 shown in Table 1 below have been prepared. Their NMR and LCMS properties and the methods used to prepare them are set out in Table 3. The starting materials for each of the Examples are listed in Table 2.

TABLE 1

Example compounds

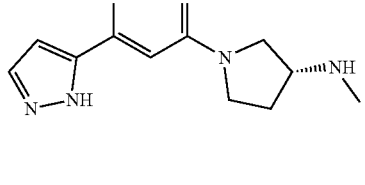

Example 1-1

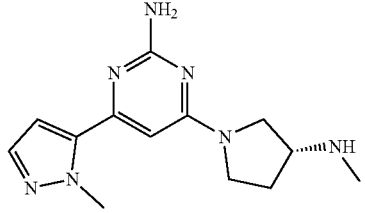 [SMILES: CN[C@@H]1CCN(c2cc(-c3ccnn3C)nc(N)n2)C1]

Example 1-2

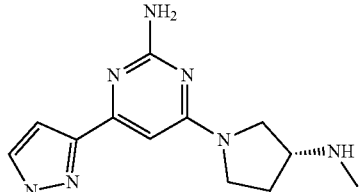

Example 2-1

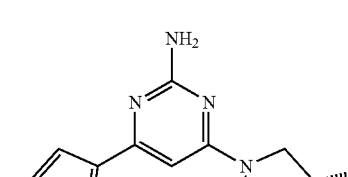

Example 2-2

TABLE 1-continued
| Example compounds | |
|---|---|
| 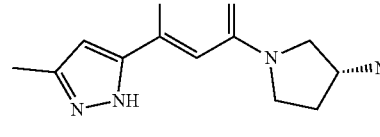 | Example 3-1 |
| 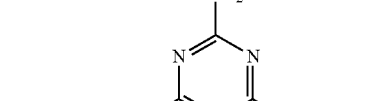 | Example 3-2 |
| 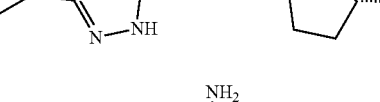 | Example 3-3 |
| 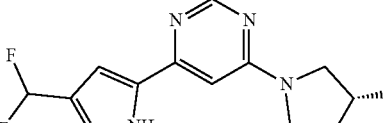 | Example 3-4 |
| 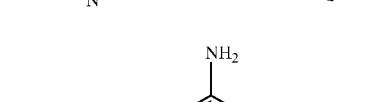 | Example 3-5 |
| 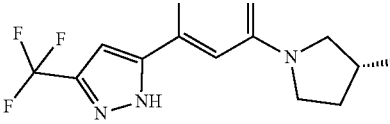 | Example 4-1 |
| 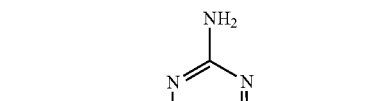 | Example 4-2 |

TABLE 1-continued
| Example compounds | |
|---|---|
| 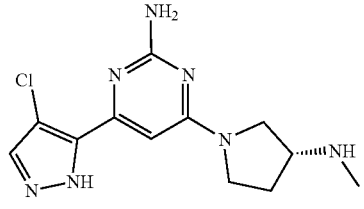 | Example 4-3 |
| 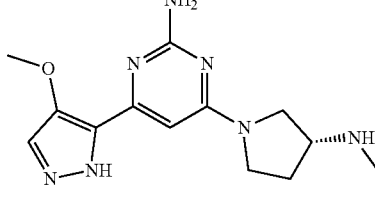 | Example 4-4 |
| 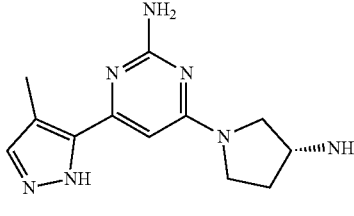 | Example 4-5 |
| 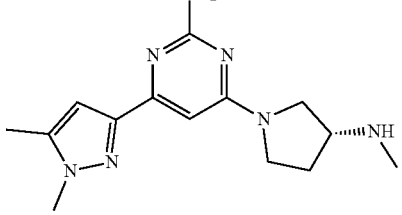 | Example 5-1 |
| 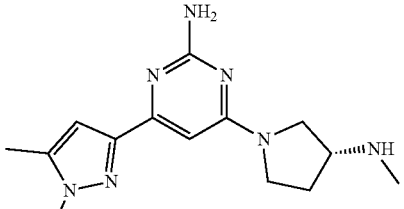 | Example 5-2 |
| 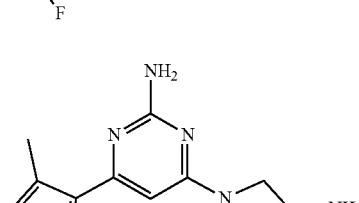 | Example 6-1 |

TABLE 1-continued
Example compounds
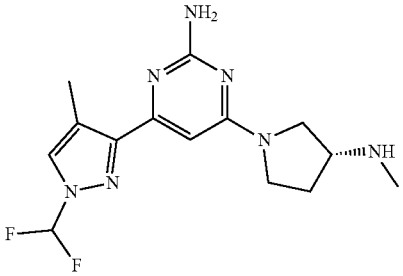 [SMILES: CN[C@@H]1CCN(c2cc(-c3ccn(C(F)F)n3)nc(N)n2)C1] Example 6-2
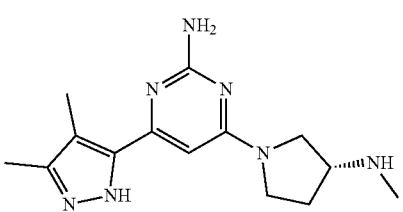 Example 7-1
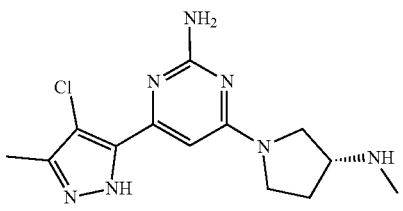 Example 7-2
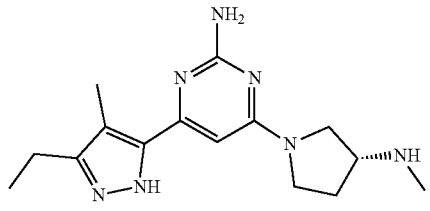 [SMILES: CCc1n[nH]c(-c2cc(N3CC[C@@H](NC)C3)nc(N)n2)c1C] Example 7-3
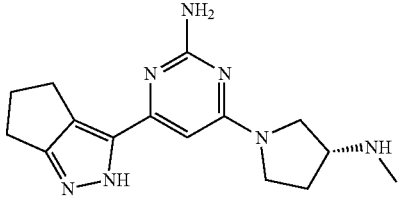 [SMILES: CN[C@@H]1CCN(c2cc(-c3[nH]nc4c3CCC4)nc(N)n2)C1] Example 7-4
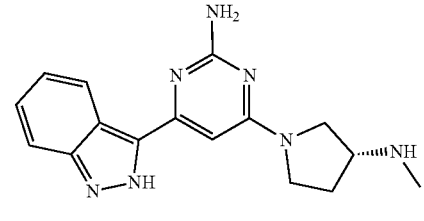 [SMILES: CN[C@@H]1CCN(c2cc(-c3[nH]nc4ccccc34)nc(N)n2)C1] Example 7-5
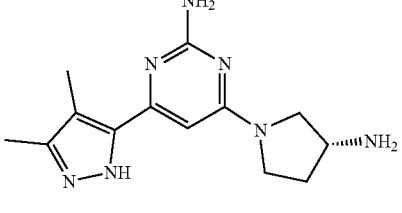 Example 7-6

TABLE 1-continued

Example compounds

| | |
|---|---|
| (structure) | Example 7-7 |
| (structure) | Example 7-8 |
| (structure) | Example 8-1 |
| (structure) | Example 8-2 |
| (structure) | Example 8-3 |
| (structure) | Example 8-4 |
| (structure) | Example 8-5 |

TABLE 1-continued

Example compounds

| Structure | Example |
|---|---|
| (difluoromethyl-pyrazole)-pyrimidine-2-amine-(3-methylamino)pyrrolidine | Example 8-6 |
| (trifluoromethyl-pyrazole)-pyrimidine-2-amine-(3-methylamino)pyrrolidine | Example 8-7 |
| (2,2,2-trifluoroethyl-pyrazole)-pyrimidine-2-amine-(3-methylamino)pyrrolidine | Example 8-8 |
| (2-hydroxyethyl-pyrazole)-pyrimidine-2-amine-(3-methylamino)pyrrolidine | Example 8-9 |
| (2-methoxyethyl-pyrazole)-pyrimidine-2-amine-(3-methylamino)pyrrolidine | Example 8-10 |
| (oxetanyl-pyrazole)-pyrimidine-2-amine-(3-methylamino)pyrrolidine | Example 8-11 |
| (2-cyanoethyl-pyrazole)-pyrimidine-2-amine-(3-methylamino)pyrrolidine | Example 8-12 |

TABLE 1-continued

Example compounds

| | |
|---|---|
| (structure) | Example 8-13 |
| (structure) | Example 8-14 |
| (structure) | Example 8-15 |
| (structure) | Example 8-16 |
| (structure) | Example 8-17 |
| (structure) | Example 8-18 |
| (structure) | Example 9-1 |

TABLE 1-continued
Example compounds
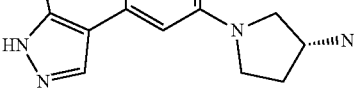
Example 9-2
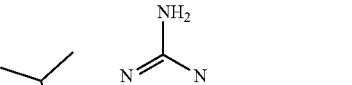
Example 9-3
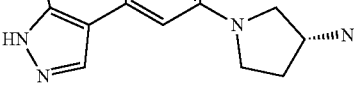
Example 9-4
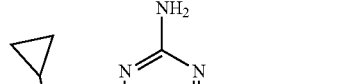
Example 9-5
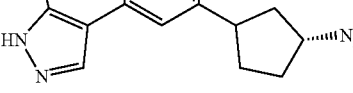
Example 9-6
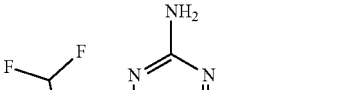
Example 9-7
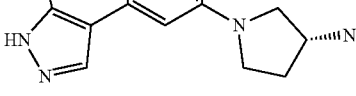
Example 10-1

TABLE 1-continued
| Example compounds | |
|---|---|
| 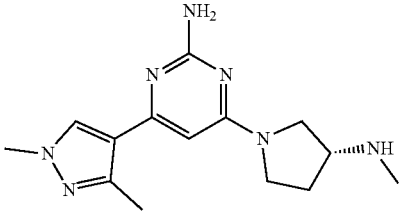 | Example 11-1 |
| 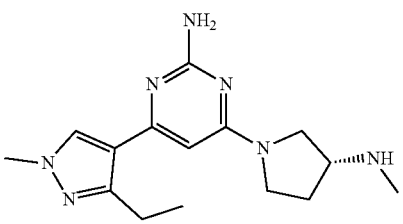 | Example 11-2 |
| 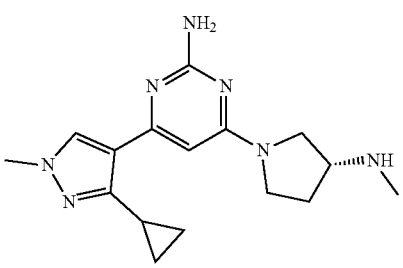 | Example 11-3 |
| 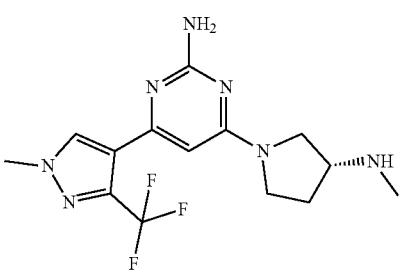 | Example 11-4 |
| 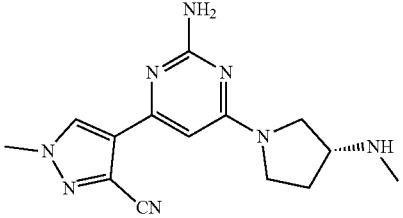 | Example 11-5 |
| 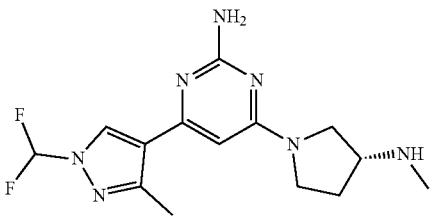 [SMILES: CN[C@@H]1CCN(c2cc(-c3cn(C(F)F)nc3C)nc(N)n2)C1] | Example 11-6 |

TABLE 1-continued

| Example compounds | |
|---|---|
| (structure) | Example 11-7 |
| (structure) | Example 11-8 |
| (structure) | Example 12-1 |
| (structure) | Example 12-2 |
| (structure) | Example 12-3 |
| (structure) | Example 12-4 |
| (structure) | Example 13-1 |

TABLE 1-continued

| Example compounds | |
|---|---|
| [structure] | Example 14-1 |
| [structure] | Example 15-1 |
| [structure] | Example 15-2 |
| [structure] | Example 16-1 |
| [structure] | Example 16-2 |
| [structure] | Example 16-3 |
| [structure] | Example 16-4 |

TABLE 1-continued
Example compounds
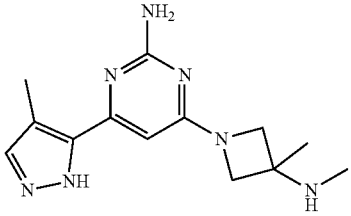 [SMILES: CNC1(C)CN(c2cc(-c3[nH]ncc3C)nc(N)n2)C1] Example 16-5
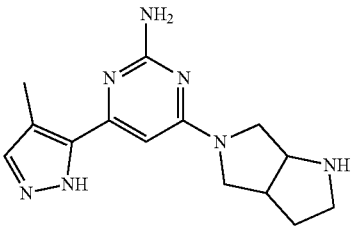 [SMILES: Cc1cn[nH]c1-c1cc(N2CC3CCNC3C2)nc(N)n1] Example 16-6
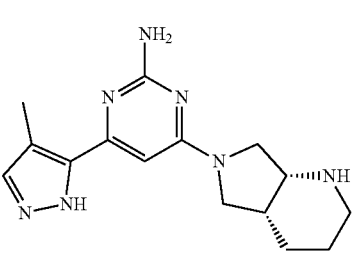 [SMILES: Cc1cn[nH]c1-c1cc(N2C[C@H]3CCCN[C@H]3C2)nc(N)n1] Example 16-7
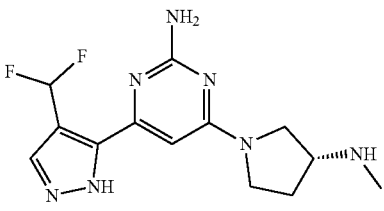 [SMILES: CN[C@@H]1CCN(c2cc(-c3[nH]ncc3C(F)F)nc(N)n2)C1] Example 16-8
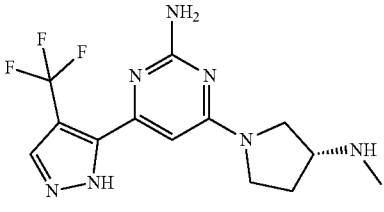 [SMILES: CN[C@@H]1CCN(c2cc(-c3[nH]ncc3C(F)(F)F)nc(N)n2)C1] Example 16-9
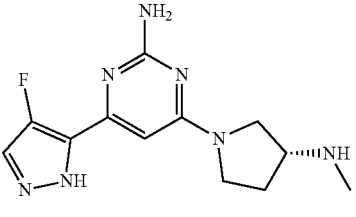 [SMILES: CN[C@@H]1CCN(c2cc(-c3[nH]ncc3F)nc(N)n2)C1] Example 16-10
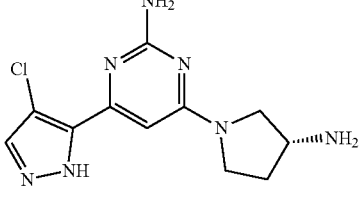 Example 16-11

TABLE 1-continued

Example compounds

| Structure | Example |
|---|---|
| (4-bromo-pyrazole)-pyrimidin-2-amine-(3-methylamino-pyrrolidine) | Example 16-12 |
| (4-bromo-pyrazole)-pyrimidin-2-amine-(3-methylamino-azetidine) | Example 16-13 |
| (4-methylthio-pyrazole)-pyrimidin-2-amine-(3-methylamino-pyrrolidine) | Example 16-14 |
| (3,4-dimethyl-pyrazole)-pyrimidin-2-amine-(3-methylamino-azetidine) | Example 17-1 |
| (3-methyl-4-trifluoromethyl-pyrazole)-pyrimidin-2-amine-(3-methylamino-pyrrolidine) | Example 17-2 |
| (4-fluoro-3-methyl-pyrazole)-pyrimidin-2-amine-(3-methylamino-pyrrolidine) | Example 17-3 |
| (4-chloro-3-methyl-pyrazole)-pyrimidin-2-amine-(3-methylamino-pyrrolidine) | Example 17-4 |

TABLE 1-continued
Example compounds
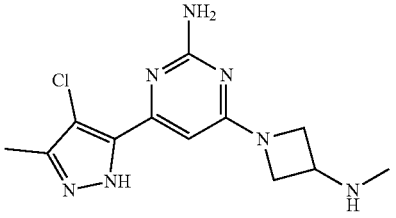
Example 17-5
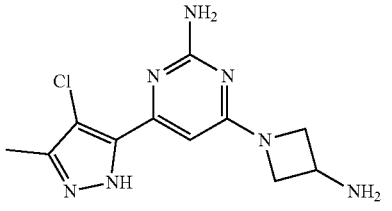 [SMILES: Cc1n[nH]c(-c2cc(N3CC(N)C3)nc(N)n2)c1Cl]
Example 17-6
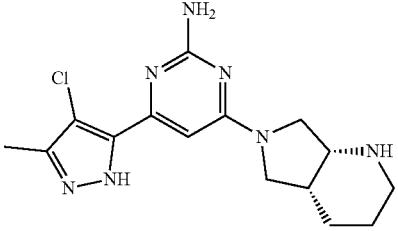 [SMILES: Cc1n[nH]c(-c2cc(N3C[C@H]4CCCN[C@H]4C3)nc(N)n2)c1Cl]
Example 17-7
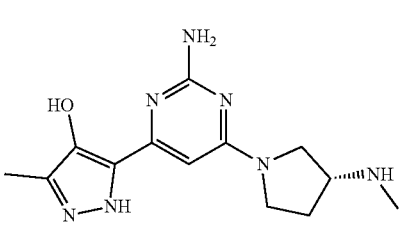
Example 17-8
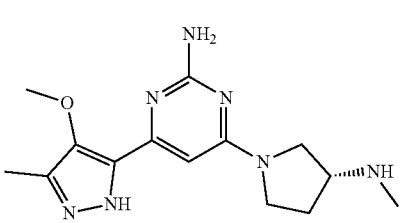
Example 17-9
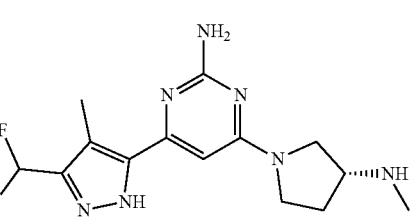
Example 17-10
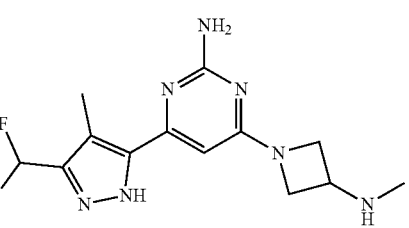
Example 17-11

TABLE 1-continued

Example compounds

| | |
|---|---|
| (structure) | Example 17-12 |
| (structure) | Example 17-13 |
| (structure) | Example 17-14 |
| (structure) | Example 17-15 |
| (structure) | Example 17-16 |
| (structure) | Example 17-17 |
| (structure) | Example 18-1 |

General Procedures

Where no preparative routes are included, the relevant intermediate is commercially available. Commercial reagents were utilized without further purification. Room temperature (rt) refers to approximately 20-27° C. 1H NMR spectra were recorded at 400 MHz on either a Bruker or Jeol instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions. Column chromatography performed using 'basic silica' refers to the use of Biotage® KP-NH silica gel. Column chromatography performed under reversed phase conditions using 'C18 silica' refers to the use of Biotage@ KP-C18 silica gel. TLC for monitoring reactions refers to TLC run using the specified mobile phase and the Silica gel F254 as a stationary phase from Merck. Microwave-mediated reactions were performed in Biotage Initiator or CEM Discover microwave reactors.

LCMS Analysis

LCMS analysis of compounds was performed under electrospray conditions using the instruments and methods given in the tables below:

| System | Instrument Name | LC Detector | Mass Detector |
|---|---|---|---|
| 1 | Waters Acquity H Class | Photo Diode Array | SQ Detector |
| 2 | Shimadzu Nexera | Photo Diode Array | LCMS-2020 |
| 3 | Agilent 1290 RRLC | Photo Diode Array | Agilent 6120 |
| 4 | Hewlett Packard HP 1100 | G1315A DAD | Micromass ZQ |
| 5 | Agilent 1260 Infinity LC | Photo Diode Array | Agilent 6120B |

| Method Name | Solvent System | Column used | Gradient | UV Range | Mass Range | Column Temp. ° C. | Flow Rate mL/min |
|---|---|---|---|---|---|---|---|
| A | (A) 5 mM ammonium acetate + 0.1% formic acid in water (B) 0.1% formic acid in acetonitrile | BEH C18 2.1 × 50 mm, 1.7 μm or equivalent | 95:5 at 0.01 min up to 0.40 min, 65:35 at 0.80 min, 45:55 at 1.20 min, 0:100 at 2.50 min up to 3.30 min, 95:5 at 3.31 min up to 4.00 min | 200-400 nm | 100-1200 amu | Ambient | 0.55 |
| B | (A) 2 mM ammonium acetate + 0.1% formic acid in water (B) 0.1% formic acid in acetonitrile | BEH C18 2.1 × 50 mm, 1.7 μm or equivalent | 98:2 at 0.01 min up to 0.30 min, 50:50 at 0.60 min, 25:75 at 1.10 min, 0:100 at 2.00 min up to 2.70 min, 98:2 at 2.71 min up to 3.00 min | 200-400 nm | 100-1200 amu | Ambient | 0.55 |
| C | (A) 20 mM ammonium acetate in water (B) methanol | X-Bridge C18 4.6 × 150 mm, 5 μm or equivalent | 100:0 at 0.01 min, 50:50 at 7.00 min, 0:100 at 9.00 min up to 11.00 min, 100:0 at 11.01 min up to 12.00 min | 200-400 nm | 60-1000 amu | Ambient | 1.00 |
| D | (A) 0.1% ammonia in water (B) 0.1% ammonia in acetonitrile | X-Bridge C18 4.6 × 50 mm, 3.5 μm or equivalent | 95:5 at 0.01 min, 10:90 at 5.00 min, 5:95 at 5.80 min up to 7.20 min, 95:5 at 7.21 min up to 10.00 min | 200-400 nm | 60-1000 amu | Ambient | 1.00 |
| E | (A) 5 mM ammonium bicarbonate in water (B) acetonitrile | X-Bridge C18 4.6 × 50 mm, 3.5 μm or equivalent | 95:5 at 0.01 min, 10:90 at 5.0 min & 5:95 at 5.80 min till 7.20 min, 95:5 at 7.21 min up to 10.0 min | 200-400 nm | 60-1000 amu | Ambient | 1.00 |
| F | (A) 2.5 L water + 2.5 mL 28% ammonia solution in water (B) 2.5 L acetonitrile + 135 mL water + 2.5 mL 28% ammonia solution in water | Gemini-NX C-18, 2.0 × 30 mm, 3 μm | 98:2 at 0.00 min up to 0.10 min, 5:95 at 2.50 min up to 3.50 min | 230-400 nm | 130-800 amu | 45 | 1.50 |
| G | (A) 2.5 L water + 2.5 mL 28% ammonia solution in water | Gemini-NX C-18, 2.0 × 30 mm, 3 μm | 98:2 at 0.00 min up to 0.10 min, 5:95 at 8.40 min up to 10.00 min | 230-400 nm | 130-800 amu | 45 | 1.50 |

| Method Name | Solvent System | Column used | Gradient | UV Range | Mass Range | Column Temp. °C. | Flow Rate mL/min |
|---|---|---|---|---|---|---|---|
| | B) 2.5 L acetonitrile + 135 mL water + 2.5 mL 28% ammonia solution in water | | | | | | |
| H | (A) 2.5 L water + 2.5 mL 28% ammonia solution in water (B) 2.5 L acetonitrile + 130 mL water + 2.5 mL 28% ammonia solution in water | Gemini-NX C-18, 2.0 × 30 mm, 3 μm | 95:5 at 0.00 min, 5:95 at 2.00 min up to 2.50 min, 95:5 at 2.60 min up to 3.0 min | 190-400 nm | 150-800 amu | 40 | 1.50 |
| I | (A) 5mM Ammonium acetate & 0.1% formic acid in water (B) 0.1% formic acid in acetonitrile | BEH C18 2.1 × 50 mm, 1.7 μm or equivalent | 98:2 at 0.01 min up to 0.5 min, 10:90 at 5.0 min, 5:95 at 6.0 min up to 7.0 min, 98:2 at 7.01 min up to 8.0 min | 200-400 nm | 60-1000 amu | Ambient | 0.45 |
| J | (A) 20 mM ammonium acetate in water (B) Methanol | X-Bridge C18 4.6 × 150 mm, 5 μm or equivalent | 90:10 at 0.01 min, 10:90 at 5.00 min, 0:100 at 7.00 min up to 11.00 min, 90:10 at 11.01 min up to 12.00 min | 200-400 nm | 60-1000 amu | Ambient | 1.00 |
| K | (A) 0.1% trifluoroacetic acid in water (B) 100% acetonitrile | YMC Triart C18 (4.6 × 150 mm), 5 μm or equivalent | 95:5 at 0.01 min, 50:50 at 5.0 min, 10:90 at 8.0 min, 0:100 at 10.0 min up to 11.0 min, 95:5 at 11.01 min up to 12.0 min | 200-400 nm | 100-1200 amu | Ambient | 1.00 |

LCMS data in the experimental section and Tables 2 and 3 are given in the format: (Instrument system, Method): Mass ion, retention time, UV detection wavelength.

Compound Purification

Final purification of compounds was performed by preparative reversed phase HPLC, chiral HPLC or chiral SFC using the instruments and methods detailed below where data is given in the following format: Purification technique: [phase (column description, column length×internal diameter, particle size), solvent flow-rate, gradient-given as % of mobile phase B in mobile phase A (over time), mobile phase (A), mobile phase (B)].

Preparative HPLC Purification:
  Shimadzu LC-20AP binary system with SPD-20A UV detector
  Gilson semi preparative HPLC system with 321 pump, GX-271 liquid handler and Gilson 171 DAD controlled with Gilson Trilution software Chiral HPLC Purification:
  Shimadzu LC-20AP binary system with SPD-20A UV detector Chiral SFC Purification:
  Waters SFC 200

Purification Method A
  Prep HPLC: [Reversed Phase (X-BRIDGE C-18, 250×19 mm, 5 μm), 15 mL/min, gradient 0%-50% (over 18 min), 100% (over 2 min), 100%-0% (over 3 min), mobile phase (A): 5 mM ammonium bicarbonate+0.1% ammonia in water, (B): acetonitrile:methanol (50:50)].

Purification Method B
  Prep HPLC: [Reversed Phase (X-BRIDGE C-18, 150×19 mm, 5 μm), 15 mL/min, gradient 0%-15% (over 21 min), 15%-15% (over 3 min), 100% (over 2 min), 100%-0% (over 2 min), mobile phase (A): 5 mM ammonium bicarbonate+0.1% ammonia in water, (B): 100% acetonitrile].

Purification Method C
  Prep HPLC: [Reversed Phase (Gemini-NX C-18, 100×30 mm, 5 μm), 30 mL/min, gradient 40%-60% (over 8.7 min), 60% (over 0.5 min), 60%-100% (over 0.2 min), 100% (over 1 min), 100%-40% (over 0.2 min), 40% (over 0.9 min), mobile phase (A): 2.5 L of water+5 mL of 28% ammonia solution in water, (B): 100% acetonitrile].

Purification Method D
  Prep HPLC: [Reversed Phase (X-BRIDGE C-18, 250×50 mm, 5 μm), 65 mL/min, gradient 0%-25% (over 30 min), 25%-25% (over 1 min), 100% (over 2 min), 100%-0% (over 5 min), mobile phase (A): 5 mM ammonium bicarbonate+0.1% ammonia in water, (B): 100% acetonitrile].

Purification Method E
  Prep HPLC: [Reversed Phase (Gemini-NX C-18, 100×30 mm, 5 μm), 30 mL/min, gradient 60%-100% (over 8.7 min), 100% (over 1.7 min), 100%-60% (over 0.2 min), 60% (over 0.9 min), mobile phase (A): 2.5 L of water+5 mL of 28% ammonia solution in water, (B): 100% acetonitrile].

Purification Method F

Prep HPLC: [Reversed Phase (Kromasil eternity C-18, 250×21.2 mm, 5 µm), 15 mL/min, gradient 7%-20% (over 27 min), 100% (over 2 min), 100%-7% (over 3 min), mobile phase (A): 0.1% trifluoroacetic acid in water, (B): 100% acetonitrile].

Purification Method G

Prep HPLC: [Reversed Phase (X-BRIDGE C-8, 150×19 mm, 5 µm), 16 mL/min, gradient 0%-25% (over 20 min), 25%-25% (over 3 min), 100% (over 2 min), 100%-0% (over 5 min), mobile phase (A): 5 mM ammonium bicarbonate+ 0.1% ammonia in water, (B): 100% acetonitrile].

Purification Method H

Prep HPLC: [Reversed Phase (Gemini-NX C-18, 100×30 mm, 5 µm), 30 mL/min, gradient 40%-70% (over 8.7 min), 70% (over 0.5 min), 70%-100% (over 0.2 min), 100% (over 1 min), 100%-40% (over 0.2 min), 40% (over 0.9 min), mobile phase (A): 2.5 L of water+5 mL of 28% ammonia solution in water, (B): 100% acetonitrile].

Purification Method I

Prep HPLC: [Reversed Phase (Gemini-NX C-18, 100×30 mm, 5 µm), 30 mL/min, gradient 5%-95% (over 8.7 min), 95% (over 0.5 min), 95%-100% (over 0.2 min), 100% (over 1 min), 100%-5% (over 0.2 min), 5% (over 0.9 min), mobile phase (A): 2.5 L of water+5 mL of 28% ammonia solution in water, (B): 100% acetonitrile].

Purification Method J

Prep HPLC: [Reversed Phase (Gemini-NX C-18, 100×30 mm, 5 µm), 30 mL/min, gradient 5%-35% (over 8.7 min), 35% (over 0.5 min), 35%-100% (over 0.2 min), 100% (over 1 min), 100%-5% (over 0.2 min), 5% (over 0.9 min), mobile phase (A): 2.5 L of water+5 mL of 28% ammonia solution in water, (B): 100% acetonitrile].

Purification Method K

Prep HPLC: [Reversed Phase (Gemini-NX C-18, 100×30 mm, 5 µm), 30 mL/min, gradient 60%-100% (over 8.7 min), 100% (over 1.7 min), 100%-60% (over 0.2 min), 60% (over 0.9 min), mobile phase (A): 2.5 L of water+5 mL of 28% ammonia solution in water, (B): 100% acetonitrile].

Purification Method L

Prep HPLC: [Reversed Phase (X-BRIDGE C-18, 250×19 mm, 5 µm), 10 mL/min, gradient 0%-20% (over 30 min), 20%-20% (over 9 min), 100% (over 3 min), 100%-0% (over 8 min), mobile phase (A): 5 mM ammonium bicarbonate+ 0.1% ammonia in water, (B): 100% acetonitrile].

Purification Method M

Prep HPLC: [Reversed Phase (X-BRIDGE C-18, 150×19 mm, 5 µm), 13 mL/min, gradient 0%-35% (over 18 min), 100% (over 3 min), 100%-0% (over 4 min), mobile phase (A): 5 mM ammonium bicarbonate+0.1% ammonia in water, (B): 100% acetonitrile].

Purification Method N

Chiral HPLC: [Normal Phase (CHIRALPAK IG, 250×21 mm, 5 µm), 18 mL/min, Isocratic (A:B) 70:30 (over 40 min), mobile phase (A): 0.1% diethylamine in hexane, (B): 0.1% diethylamine in isopropanol:methanol (50:50)].

Purification Method O

Prep HPLC: [Reversed Phase (X-BRIDGE C-18, 150×19 mm, 5 µm), 15 mL/min, gradient 10%-35% (over 20 min), 35% (over 3 min), 100% (over 2 min), 100%-10% (over 3 min), mobile phase (A): 5 mM ammonium bicarbonate+ 0.1% ammonia in water, (B): acetonitrile:methanol (1:1)].

Purification Method P SFC: [(CHIRALPAK IC, 250×21 mm, 5 µm), 80 mL/min, Isocratic (A:B) 65:35 (over 23 min), mobile phase (A): 100% liquid $CO_2$, (B): 0.1% diethylamine in isopropanol:acetonitrile (50:50)].

Purification Method Q

Prep HPLC: [Reversed Phase (Gemini-NX C-18, 100×30 mm, 5 µm), 30 mL/min, gradient 30%-60% (over 8.7 min), 60% (over 0.5 min), 60%-100% (over 0.2 min), 100% (over 1 min), 100%-30% (over 0.2 min), 30% (over 0.9 min), mobile phase (A): 2.5 L of water+5 mL of 28% ammonia solution in water, (B): 100% acetonitrile].

| Abbreviations | |
| --- | --- |
| CDI = | carbonyldiimidazole |
| DAST = | diethylaminosulfur trifluoride |
| DCM = | dichloromethane |
| DIPEA = | N,N-diisopropylethylamine |
| ESI = | electro spray ionisation |
| EtOAc = | ethyl acetate |
| h = | hour(s) |
| $H_2O$ = | water |
| HCl = | hydrogen chloride, hydrochloric acid |
| HPLC = | high performance liquid chromatography |
| IPA = | propan-2-ol |
| LC = | liquid chromatography |
| MeCN = | acetonitrile |
| MeOH = | methanol |
| min(s) = | minute(s) |
| MS = | mass spectrometry |
| nm = | nanometre(s) |
| NMR= | nuclear magnetic resonance |
| $POCl_3$ = | phosphorus oxychloride |
| RT = | room temperature |
| sat. = | saturated |
| SFC = | supercritical fluid chromatography |
| TEA = | triethylamine |
| TFA = | trifluoroacetic acid |
| THF = | tetrahydrofuran |
| TLC = | thin layer chromatography |

Synthesis of Intermediates:

Route 1

Typical Procedure for the Preparation of Pyrazoles, as Exemplified by the Preparation of Intermediate 12, 5-bromo-3-(difluoromethyl)-1-((2-(trimethylsilyl)ethoxy)methyl)-1H-pyrazole

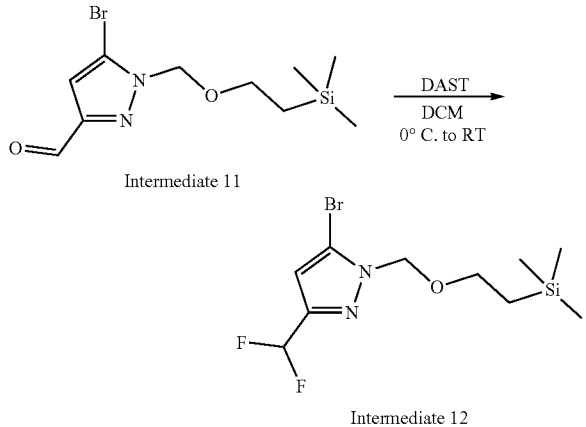

To a solution of 5-bromo-1-((2-(trimethylsilyl)ethoxy)methyl)-1H-pyrazole-3-carbaldehyde (Intermediate 11) (800 mg, 2.60 mmol) dissolved in DCM (8.7 mL) and cooled to 0° C. was added diethylaminosulfur trifluoride (0.86 mL, 6.51 mmol) dropwise. The reaction mixture was then stirred at 0° C. for 23 hours, allowing it to slowly warm to RT. The reaction mixture was then quenched at 0° C. by the addition of saturated sodium bicarbonate solution and the resulting mixture was extracted using DCM (×2). The combined organic phases were filtered through a phase separator and concentrated under reduced pressure. The crude product was then purified using column chromatography (silica, 0-50% dichloromethane in petroleum ether) to give 5-bromo-3-(difluoromethyl)-1-((2-(trimethylsilyl) ethoxy)methyl)-1H-pyrazole (Intermediate 12) (716 mg, 84%).

The data for Intermediate 12 are in Table 2.

Route 2

Typical Procedure for the Preparation of Pyrazoles, as Exemplified by the Preparation of Intermediate 15, 3-(trifluoromethyl)-1H-pyrazole-5-carboxylic acid

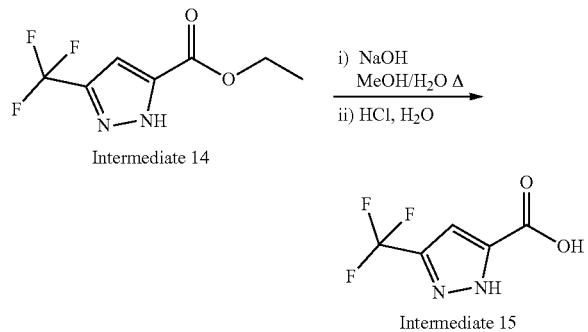

Ethyl 3-(trifluoromethyl)-1H-pyrazole-5-carboxylate (Intermediate 14) (1.50 g, 7.21 mmol) was dissolved in MeOH (15 mL) and aqueous NaOH (2 M, 10 mL) was added dropwise. The resulting reaction mixture was stirred at 70° C. for 14 h, then concentrated in-vacuo. The residue was dissolved in water (5 mL), acidified with aqueous HCl (1 M) to pH=2-3 and extracted with ethyl acetate (3×15 mL). The combined organic layers were dried ($Na_2SO_4$) and the solvent was removed in-vacuo to give the crude product which was triturated with pentane (decanting off the solvent) and dried under high vacuum to give 3-(trifluoromethyl)-1H-pyrazole-5-carboxylic acid (Intermediate 15) (1.30 g, 100%) as a solid.

The data for Intermediate 15 are in Table 2.

Route 3

Typical Procedure for the Preparation of Pyrazoles, as Exemplified by the Preparation of Intermediate 22, 4-ethyl-1-((2-(trimethylsilyl)ethoxy)methyl)-1H-pyrazole

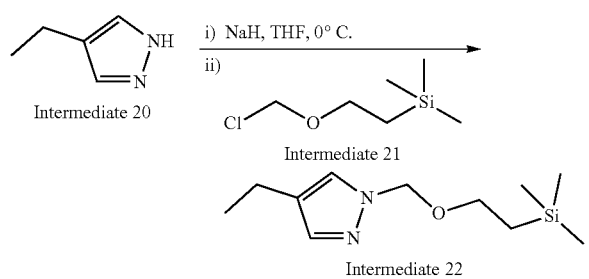

Sodium hydride suspension in mineral oil (60%, 624 mg, 15.6 mmol) was added in small increments to a solution of 4-ethyl-1H-pyrazole (Intermediate 20) (1.0 g, 10.4 mmol) in THF (5.2 mL), pre-cooled to 0° C. The reaction mixture was stirred at 0° C. for 45 min before the dropwise addition of (2-(chloromethoxy)ethyl)trimethylsilane (Intermediate 21) (2.0 mL, 11.4 mmol). The reaction mixture was stirred at room temperature for 18 h, then quenched at 0° C. by the addition of water and extracted into ethyl acetate. The aqueous layer was further extracted using ethyl acetate (×2), and the combined organic phases were washed with brine, filtered through a phase separator and concentrated under reduced pressure. The residue was purified using column chromatography (silica, 0-10% ethyl acetate in petroleum ether) to give 4-ethyl-1-((2-(trimethylsilyl)ethoxy)methyl)-1H-pyrazole, (Intermediate 22) (1.50 g, 63%).

The data for Intermediate 22 are in Table 2.

Route 4

Typical Procedure for the Preparation of Pyrimidines, as Exemplified by the Preparation of Intermediate 26, tert-butyl (R)-(1-(6-chloro-2-(2,5-dimethyl-1H-pyrrol-1-yl)pyrimidin-4-yl)pyrrolidin-3-yl)(methyl)carbamate

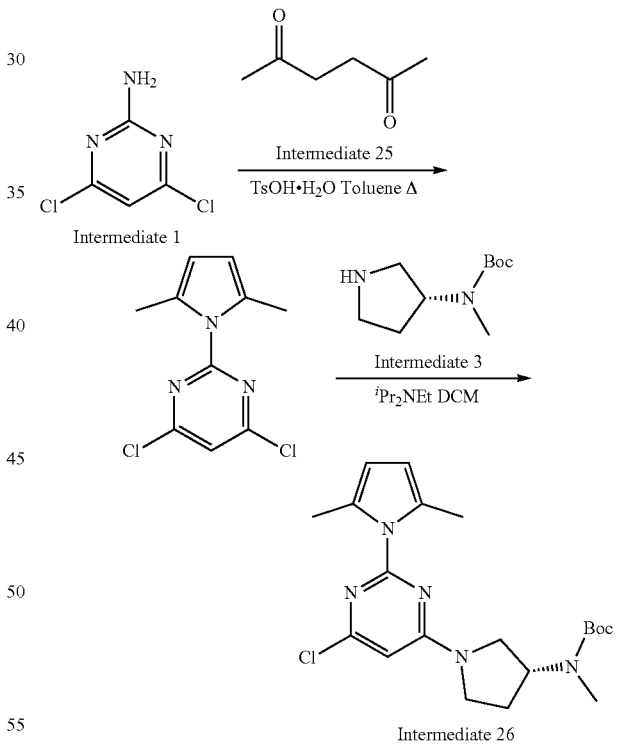

A mixture of 4,6-dichloropyrimidin-2-amine (Intermediate 1) (18.54 g, 113 mmol), hexane-2,5-dione (Intermediate 25) (26.5 mL, 226 mmol) and p-toluenesulfonic acid monohydrate (215 mg, 1.13 mmol) in dry toluene (500 mL) was heated at reflux under Dean & Stark conditions for 17 h (overnight). The reaction mixture was cooled to room temperature and washed with sat. sodium bicarbonate solution. The aqueous layer was extracted with EtOAc, and the combined organic phases were washed with water and brine, filtered through a phase separator and concentrated. The residue was then filtered through a plug of silica, washing with DCM and concentrated to give 4,6-dichloro-2-(2,5-dimethyl-1H-pyrrol-1-yl)pyrimidine (24.9 g, 91%).

1H NMR (400 MHZ, Chloroform-d) δ 7.19 (s, 1H), 5.91 (s, 2H), 2.42 (s, 6H).

To a solution of 4,6-dichloro-2-(2,5-dimethyl-1H-pyrrol-1-yl)pyrimidine (3.0 g, 12.4 mmol) dissolved in DCM (20 mL) was added N,N-diisopropylethylamine (6.48 mL, 37.2 mmol) followed by tert-butyl (R)-methyl(pyrrolidin-3-yl)carbamate (Intermediate 3) (2.61 g, 13.0 mmol) dissolved in DCM (20 mL). The reaction mixture was stirred at room temperature for 20 h, then quenched by the addition of aqueous HCl (1 M) and extracted using DCM (×2). The combined organic phases were filtered through a phase separator and concentrated under reduced pressure. The residue was then purified using column chromatography (silica, 0-25% ethyl acetate in petroleum ether) to give tert-butyl (R)-(1-(6-chloro-2-(2,5-dimethyl-1H-pyrrol-1-yl)pyrimidin-4-yl)pyrrolidin-3-yl)(methyl)carbamate (Intermediate 26) (3.87 g, 77%).

The data for Intermediate 26 are in Table 2.
Route 5

Typical Procedure for the Preparation of Pyrazoles, as Exemplified by the Preparation of Intermediate 31, 1,5-dimethyl-1H-pyrazole-3-carboxylic acid

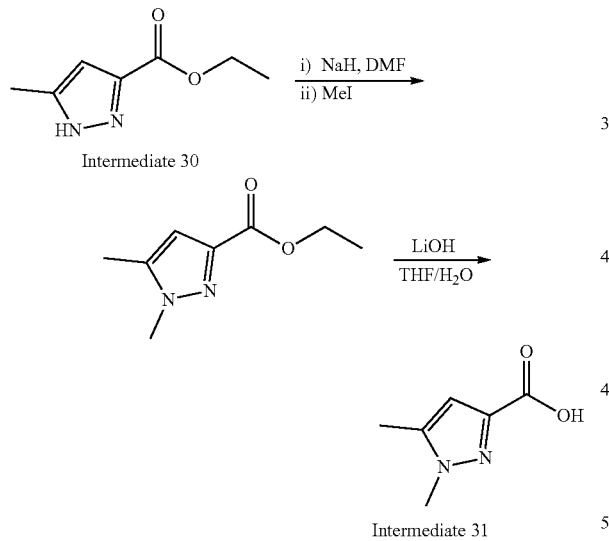

Ethyl 5-methyl-1H-pyrazole-3-carboxylate (Intermediate 30) (2.0 g, 0.01 mol) was dissolved in DMF (15 mL) and sodium hydride suspension in mineral oil (60%, 1.5 g, 0.03 mol) was added portion-wise under nitrogen at 0° C. The mixture was stirred for 1 h, then methyl iodide (3.6 g, 0.02 mol) was added dropwise under nitrogen and the resulting mixture was stirred at room temperature for 16 h. The reaction mixture was concentrated, and the residue was partitioned between H₂O (25 mL) and EtOAc (15 mL). The aqueous layer was further extracted with EtOAc (3×15 mL) and the combined organic layers were dried (Na₂SO₄) and the solvent was removed in-vacuo. The residue was purified by column chromatography (Normal-Phase 60-120 mesh silica gel, 0 to 3% MeOH in DCM) to give ethyl 1,5-dimethyl-1H-pyrazole-3-carboxylate (2.0 g, 96%) as a gum.

LCMS (System 1, Method B): m/z 169 (M+H)⁺ (ESI +ve), at 1.42 min, 230 nm.

Ethyl 1,5-dimethyl-1H-pyrazole-3-carboxylate (2.0 g, 0.01 mol), and LiOH·H₂O (1.4 g, 0.03 mol) were taken into THF (5 mL) and water (2 mL) and stirred at 0° C. for 1 h. The reaction mixture was partitioned between H₂O (25 mL) and EtOAc (15 mL), and the organic extract was discarded. The aqueous layer was acidified to pH 1-2 using aqueous HCl (1 M) and the resulting mixture was re-extracted with EtOAc (3×15 mL). The combined extracts were dried (Na₂SO₄) and the solvent was removed in-vacuo to give 1,5-dimethyl-1H-pyrazole-3-carboxylic acid (Intermediate 31) (1.3 g, 81%) as a gum.

The data for Intermediate 31 are in Table 2.
Route 6

Typical Procedure for the Preparation of Pyrazoles, as Exemplified by the Preparation of Intermediate 36, 1-(difluoromethyl)-4-methyl-1H-pyrazole-3-carboxylic acid

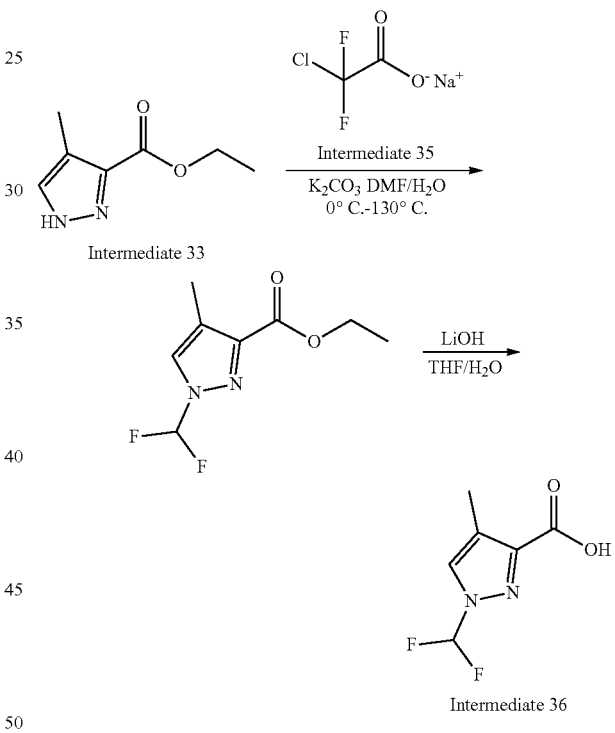

Ethyl 4-methyl-1H-pyrazole-3-carboxylate (Intermediate 33) (1.0 g, 6.49 mmol) was dissolved in DMF:H₂O (9.0 mL:1.0 mL) and K₂CO₃ (3.58 g, 25.9 mmol) and sodium 2-chloro-2,2-difluoroacetate (Intermediate 35) (3.94 g, 25.9 mmol) were added at 0° C. and then the mixture was heated at 130° C. for 20 min. The reaction mixture was cooled to RT and ice-cold water was added. The aqueous layer was extracted with EtOAc (3×50 mL) and the combined organic layer was washed with brine solution, dried over Na₂SO₄, filtered and concentrated. The residue was purified by column chromatography (Normal-Phase 60-120 mesh silica gel, 25% EtOAc in hexanes) to give ethyl 1-(difluoromethyl)-4-methyl-1H-pyrazole-3-carboxylate (325 mg, 25%) as a solid.

LCMS (System 3, Method D): m/z 205 (M+H)⁺ (ESI +ve), at 3.77 min, 202 nm.

Ethyl 1-(difluoromethyl)-4-methyl-1H-pyrazole-3-carboxylate (325 mg, 1.59 mmol) was dissolved in MeOH:H$_2$O (9:1, 10 mL), LiOH·H$_2$O (334 mg, 7.96 mol) was added 0° C. and the reaction mixture was stirred at RT overnight. The solvent was removed under reduced pressure and ice-cold water was added. The mixture was neutralized with dilute aqueous HCl and the aqueous layer was extracted with EtOAc (3×50 mL). The combined organic extracts were washed with brine solution, dried over Na$_2$SO$_4$, filtered and concentrated to give 1-(difluoromethyl)-4-methyl-1H-pyrazole-3-carboxylic acid (Intermediate 36) (251 mg, 96%) as a solid.

The data for Intermediate 36 are in Table 2.

Route 7

Typical Procedure for the Preparation of Pyrazoles, as Exemplified by the Preparation of Intermediate 63, ethyl 3-(4-(4,4,5,5-tetramethyl-1,3,2-dioxaborolan-2-yl)-1H-pyrazol-1-yl)piperidine-1-carboxylate

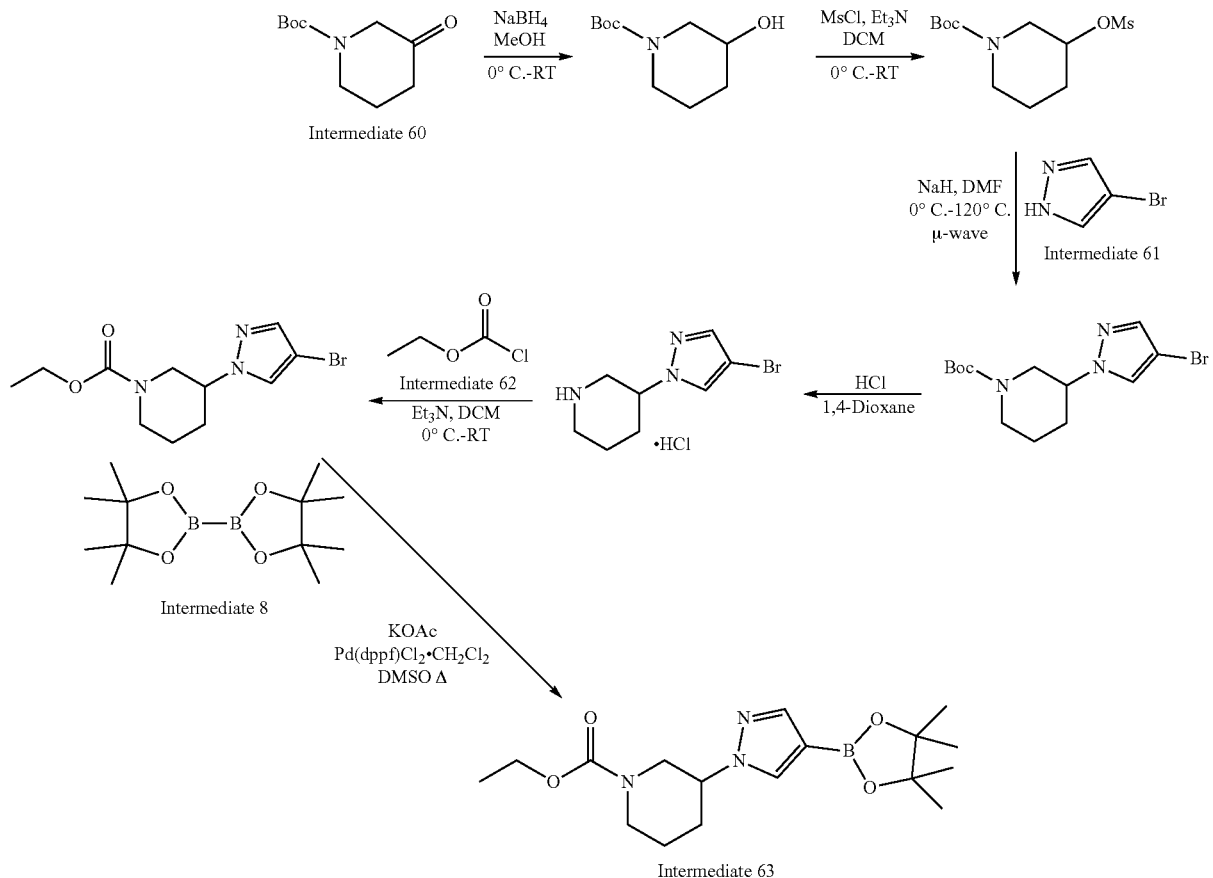

tert-Butyl 3-oxopiperidine-1-carboxylate (Intermediate 60) (1.30 g, 6.53 mmol) was dissolved in methanol (20 mL), and NaBH$_4$ (750 mg, 19.6 mmol) at was added portion-wise at 0° C. The resulting mixture was stirred at room temperature for 3 h, then partitioned between H$_2$O (50 mL) and EtOAc (20 mL). The aqueous layer was further extracted with EtOAc (2×20 mL), and the combined organic layers were dried (Na$_2$SO$_4$) and the solvent was removed in-vacuo to give crude product. The residue was purified by column chromatography (Normal-Phase 60-120 mesh silica gel, 0 to 50% EtOAc in hexanes) to give tert-butyl 3-hydroxypiperidine-1-carboxylate (1.00 g, 76%) as a solid.

LCMS (System 1, Method B): m/z 202 (M+H)$^+$ (ESI +ve), at 1.50 min, 202 nm.

tert-Butyl 3-hydroxypiperidine-1-carboxylate (1.00 g, 4.98 mmol) and TEA (2.1 mL, 14.9 mmol) were dissolved in DCM (15 mL) at 0° C., methane sulfonyl chloride (850 mg, 7.45 mmol) was added dropwise at 0° C. and the resulting mixture was stirred at room temperature for 3 h. The reaction mixture was then partitioned between H$_2$O (50 mL) and DCM (20 mL), and the aqueous layer was further extracted with DCM (2×20 mL). The combined organic layers were dried (Na$_2$SO$_4$) and the solvent was removed in-vacuo. The residue was purified by column chromatography (Normal-Phase 60-120 mesh silica gel, 0 to 30% EtOAc in hexanes) to give tert-butyl 3-((methylsulfonyl)oxy)piperidine-1-carboxylate (1.03 g, 94%) as a gum.

LCMS (System 1, Method B): m/z 280 (M+H)⁺ (ESI +ve), at 1.61 min, 202 nm.

4-Bromo-1H-pyrazole (Intermediate 61) (526 mg, 3.58 mmol) was dissolved in DMF (10 mL), sodium hydride suspension in mineral oil (60%, 260 mg, 6.45 mmol) was added at 0° C. and the resulting mixture was stirred for 30 min. tert-Butyl 3-((methylsulfonyl)oxy)piperidine-1-carboxylate (1.00 g, 3.58 mmol) as a solution in DMF (5 mL) was added dropwise at 0° C. and the mixture was stirred at 120° C. for 1 h using microwave heating. The reaction mixture was partitioned between H₂O (50 mL) and EtOAc (20 mL) and the aqueous layer was further extracted with EtOAc (2×20 mL). The combined organic layers were dried (Na₂SO₄) and the solvent was removed in-vacuo. The residue was purified by column chromatography (Normal-Phase 60-120 mesh silica gel, 0 to 3% MeOH in DCM) to give tert-butyl 3-(4-bromo-1H-pyrazol-1-yl)piperidine-1-carboxylate (1.10 g, 93%) as a gum.

LCMS (System 1, Method B): m/z 274/276 (M−56+H)⁺ (ESI +ve), at 1.82 min, 230 nm.

tert-Butyl 3-(4-bromo-1H-pyrazol-1-yl)piperidine-1-carboxylate (700 mg, 2.12 mmol) was dissolved in HCl solution in 1,4-dioxane (4 M, 15 mL) at 0° C. and the resulting mixture was stirred at room temperature for 3 h. The reaction mixture was concentrated and the residue then triturated with diethyl ether (2×10 mL) to give 3-(4-bromo-1H-pyrazol-1-yl)piperidine hydrochloride salt (400 mg, 71%) as a solid.

LCMS (System 2, Method E): m/z 230/232 (M+H)⁺ (ESI +ve), at 2.54 min, 230 nm.

3-(4-Bromo-1H-pyrazol-1-yl)piperidine hydrochloride salt (500 mg, 2.17 mmol) and TEA (0.90 mL, 6.52 mmol) were dissolved in DCM (15 mL) at 0° C. and ethyl chloroformate (Intermediate 62) (350 mg, 3.26 mmol) was added dropwise at 0° C. The resulting mixture was stirred for 3 h at room temperature, then partitioned between H₂O (20 mL) and DCM (10 mL). The aqueous layer was further extracted with DCM (2×10 mL) and the combined organic layers were dried (Na₂SO₄) and the solvent was removed in-vacuo. The residue was purified by column chromatography (Normal-Phase 60-120 mesh silica gel, 0 to 2% MeOH in DCM) to give ethyl 3-(4-bromo-1H-pyrazol-1-yl)piperidine-1-carboxylate (400 mg, 61%) as a gum.

LCMS (System 1, Method B): m/z 302/304 (M+H)⁺ (ESI +ve), at 1.67 min, 233 nm.

Ethyl 3-(4-bromo-1H-pyrazol-1-yl)piperidine-1-carboxylate (400 mg, 1.32 mmol), bis(pinacolato)diboron (Intermediate 8) (400 mg, 1.59 mmol) and potassium acetate (450 mg, 4.63 mmol) were dissolved in DMSO (5 mL) under nitrogen and the resulting solution was degassed for 15 min. [1,1'-Bis(diphenylphosphino)ferrocene]dichloropalladium (II) dichloromethane complex (CAS: 95464-05-4) (378 mg, 0.46 mmol) was added and the mixture was heated at 90° C. for 16 h. The reaction mixture was then partitioned between H₂O (25 mL) and EtOAc (15 mL), and the aqueous layer was further extracted with EtOAc (2×15 mL). The combined organic layers were dried (Na₂SO₄) and the solvent was removed in-vacuo. The residue was purified by column chromatography (Normal-Phase 60-120 mesh silica gel, 0 to 2% MeOH in DCM) to give ethyl 3-(4-(4,4,5,5-tetramethyl-1,3,2-dioxaborolan-2-yl)-1H-pyrazol-1-yl)piperidine-1-carboxylate (Intermediate 63) (200 mg, 43%) as a gum.

The data for Intermediate 63 are in Table 2.

Route 8

Typical Procedure for the Preparation of Pyrazoles, as Exemplified by the Preparation of Intermediate 71, 4-bromo-3-ethyl-1-(tetrahydro-2H-pyran-2-yl)-1H-pyrazole

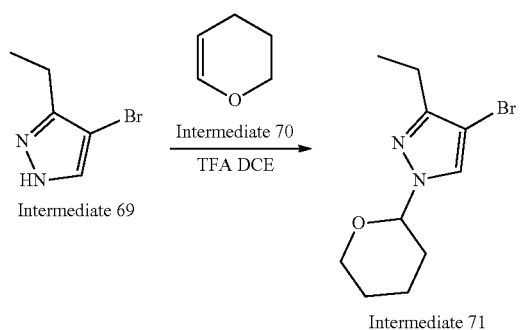

4-Bromo-3-ethyl-1H-pyrazole (Intermediate 69) (500 mg, 2.8 mmol) was dissolved in 1,2-dichloroethane (5 mL) and 3,4-dihydropyran (Intermediate 70) (482 mg, 5.7 mmol) was added. Trifluoroacetic acid (2-3 drops) was then added and the resulting mixture was stirred at RT for 24 h. The solvent was evaporated, and the residue was partitioned between ethyl acetate (25 mL) and water (15 ml). The organic layer was separated, dried (Na₂SO₄) and evaporated under reduced pressure. The residue was purified by column chromatography (silica gel 60-120 mesh, 0-20% ethyl acetate in hexane) to give 4-bromo-3-ethyl-1-(tetrahydro-2H-pyran-2-yl)-1H-pyrazole (Intermediate 71) (700 mg, 97%) as a gum.

The data for Intermediate 71 are in Table 2.

Route 9

Typical Procedure for the Preparation of Pyrrolidines, as Exemplified by the Preparation of Intermediate 88, benzyl methyl(3-methylpyrrolidin-3-yl)carbamate hydrochloride

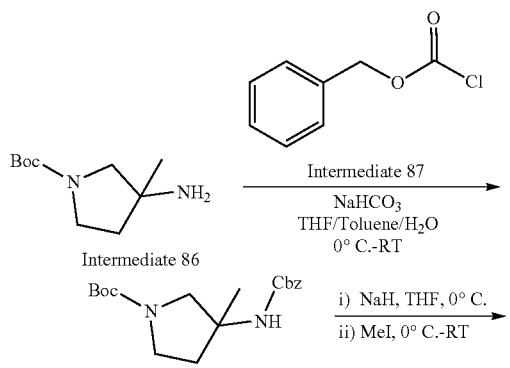

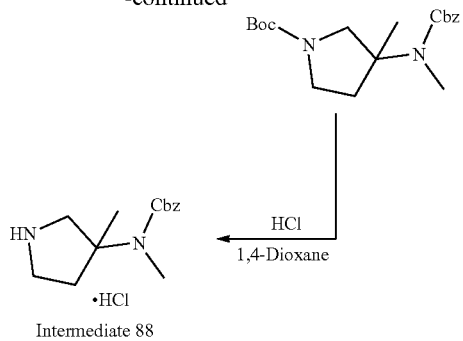

Intermediate 88 tert-Butyl 3-amino-3-methylpyrrolidine-1-carboxylate (Intermediate 86) (600 mg, 3.00 mmol) was dissolved in THF (8 mL) and a solution of NaHCO$_3$ (504 mg, 6.00 mmol) in water (8 mL) was added. The mixture was cooled to 0° C. and benzyl chloroformate (Intermediate 87) as a solution in toluene (50%, 1.1 mL, 3.30 mmol) was added, and the resulting mixture was stirred at 25° C. for 2 h. The reaction mixture was then partitioned between H$_2$O (30 mL) and ethyl acetate (20 mL), and the aqueous layer was further extracted with ethyl acetate (2×20 mL). The combined organic layers were dried (Na$_2$SO$_4$) and the solvent was removed in-vacuo. The residue was purified by triturating with pentane to give tert-butyl 3-(((benzyloxy)carbonyl)amino)-3-methylpyrrolidine-1-carboxylate (900 mg, 90%) as a gum.

LCMS (System 3, Method D): m/z 333 (M−H)$^−$ (ESI −ve), at 4.68 min, 202 nm.

tert-Butyl 3-(((benzyloxy)carbonyl)amino)-3-methylpyrrolidine-1-carboxylate (900 mg, 2.69 mmol) was dissolved in THF (15 mL) and the solution was cooled to 0° C. Sodium hydride suspension in mineral oil (60%, 323 mg, 8.08 mmol) was added and the reaction mixture was stirred at 0° C. for 30 min. Methyl iodide (573 mg, 4.04 mmol) was added at 0° C. and the resulting reaction mixture was stirred at 25° C. for 4 h. The mixture was then partitioned between H$_2$O (40 mL) and EtOAc (25 mL), and the aqueous layer was further extracted with EtOAc (2×25 mL). The combined organic layers were dried (Na$_2$SO$_4$) and the solvent was removed in-vacuo to give the crude product, which was purified by triturating with pentane to give tert-butyl 3-(((benzyloxy)carbonyl)(methyl)amino)-3-methylpyrrolidine-1-carboxylate (910 mg, 97%) as a gum.

LCMS (System 3, Method D): m/z 349 (M+H)$^+$ (ESI +ve), at 5.05 min, 202 nm.

tert-Butyl 3-(((benzyloxy)carbonyl)(methyl)amino)-3-methylpyrrolidine-1-carboxylate (900 mg, 2.59 mmol) was dissolved 1,4-dioxane (5 mL) and cooled to 0° C. HCl solution in 1,4-dioxane (4 M, 10 mL) was added under a nitrogen atmosphere and the resulting mixture was stirred at room temperature for 6 h. The reaction mixture was concentrated and the crude product salt was purified by trituration with pentane (2×2 mL) to give benzyl methyl(3-methylpyrrolidin-3-yl)carbamate hydrochloride (Intermediate 88) (640 mg, 100%) as a gum.

The data for Intermediate 88 are in Table 2.

Route 10

Typical Procedure for the Preparation of Pyrazoles, as Exemplified by the Preparation of Intermediate 111, 4-(difluoromethyl)-1-(4-methoxybenzyl)-1H-pyrazole-3-carboxylic acid

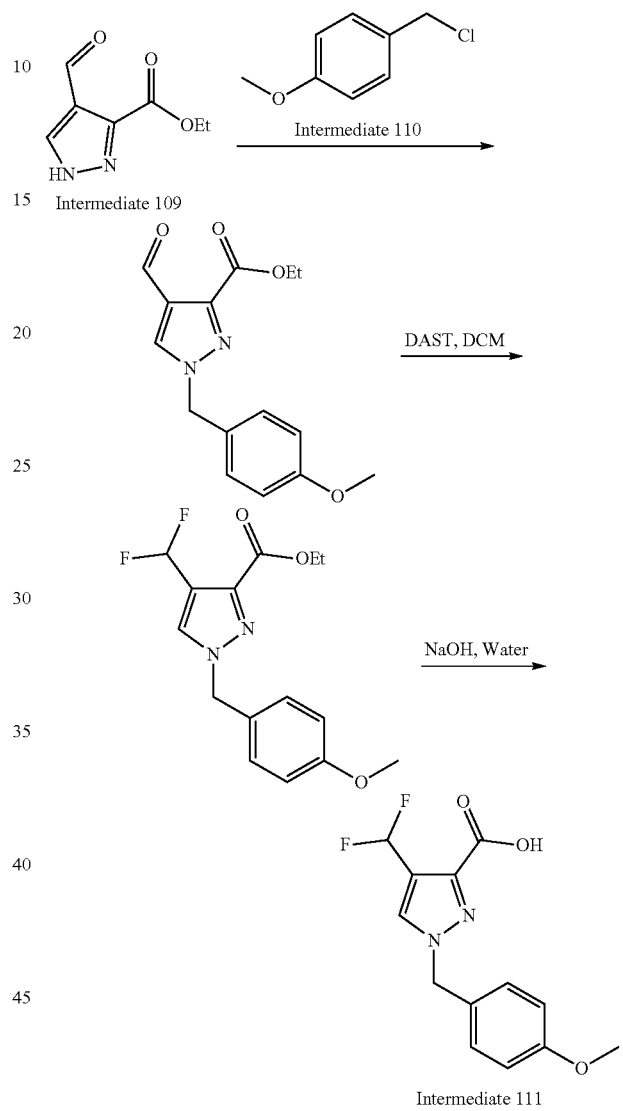

Intermediate 111

Ethyl 4-formyl-1H-pyrazole-3-carboxylate (Intermediate 109) (1 g, 5.95 mmol) was dissolved in DMF (10 mL), followed by the addition of 1-(chloromethyl)-4-methoxybenzene (Intermediate 110) (1.02 g, 6.54 mmol) at RT. To this was then added potassium carbonate (904 mg, 6.54 mmol) and potassium iodide (10 mg) and the reaction stirred at 80° C. for 16 h. The reaction mixture was partitioned between H$_2$O (250 mL) and EtOAc (500 mL) and the aqueous layer was further extracted with EtOAc (2×150 mL). The combined organic layers were dried (Na$_2$SO$_4$), filtered and concentrated in vacuo. The resulting product was purified by column chromatography (Normal-Phase 60-120 mesh silica gel, 0 to 50% EtOAc in Hexane) to give ethyl 4-formyl-1-(4-methoxybenzyl)-1H-pyrazole-3-carboxylate (1.0 g, 58%).

LCMS (System 1, Method B): m/z 289 (M+H)$^+$ (ESI +ve), at 1.61 min, 275 nm.

Ethyl 4-formyl-1-(4-methoxybenzyl)-1H-pyrazole-3-carboxylate (0.8 g, 2.77 mmol) was dissolved in DCM (8 mL). The reaction mixture was cooled to −70° C. and to this was then added dropwise diethylaminosulfur trifluoride (1.11 g, 6.94 mmol). The reaction mixture was then allowed to warm at RT and stirred for 16 h. The reaction mixture was partitioned between saturated aqueous NaHCO₃ (250 mL) and EtOAc (500 mL). The aqueous layer was further extracted with EtOAc (2×150 mL) and the combined organic layers were dried (Na₂SO₄), filtered and concentrated in vacuo. The resulting product was purified by column chromatography (Normal-Phase 60-120 mess silica gel, 0 to 18% EtOAc in Hexane) to give ethyl 4-(difluoromethyl)-1-(4-methoxybenzyl)-1H-pyrazole-3-carboxylate (0.8 g, 93%). LCMS (System 1, Method B): m/z 311 (M+H)⁺ (ESI +ve), at 1.71 min, 230 nm.

Ethyl 4-(difluoromethyl)-1-(4-methoxybenzyl)-1H-pyrazole-3-carboxylate (0.8 g, 2.58 mmol) was dissolved in THF (4 mL) and MeOH (4 mL). To this added aqueous NaOH (2M, 6.45 mL, 12.9 mmol) and stirred at RT for 16 h. The organic solvent was removed in vacuo and the resulting solution was cooled to 10° C. The reaction mixture was acidified to pH 2 using aqueous 6M HCl and the resulting precipitate was collected by filtration and dried in vacuo to give 4-(difluoromethyl)-1-(4-methoxybenzyl)-1H-pyrazole-3-carboxylic acid (Intermediate 111) (0.7 g, 96%).

The data for Intermediate 111 are in Table 2.

Route 11

Typical Procedure for the Partial Deprotection of Pyrimidines, as Exemplified by the Preparation of Intermediate 118, tert-butyl (R)-(1-(2-amino-6-(4-fluoro-1-((2-(trimethylsilyl)ethoxy)methyl)-1H-pyrazol-5-yl)pyrimidin-4-yl)pyrrolidin-3-yl)(methyl)carbamate

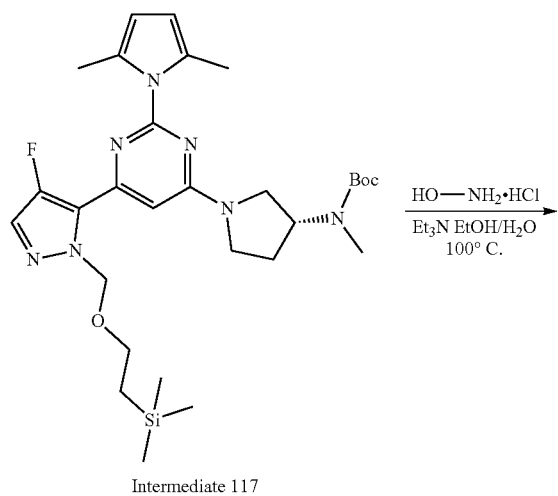

Intermediate 117

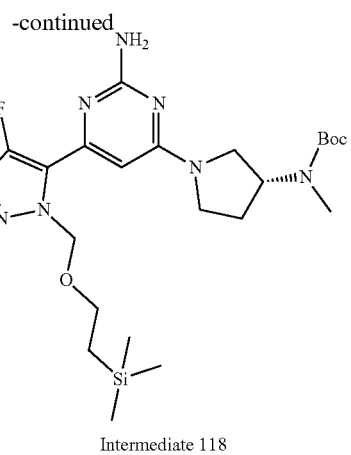

Intermediate 118

A mixture of tert-butyl (R)-(1-(2-(2,5-dimethyl-1H-pyrrol-1-yl)-6-(4-fluoro-1-((2-(trimethylsilyl)ethoxy)methyl)-1H-pyrazol-5-yl)pyrimidin-4-yl)pyrrolidin-3-yl)(methyl)carbamate (Intermediate 117) (226 mg, 0.39 mmol), hydroxylamine hydrochloride (268 mg, 3.86 mmol) and triethylamine (0.06 mL, 0.42 mmol) in ethanol (8 mL) and water (4 mL) was heated at 100° C. overnight. The reaction mixture was diluted with water and extracted with EtOAc (×3). The combined organic extracts were washed with brine, passed through a phase separator and concentrated to give tert-butyl (R)-(1-(2-amino-6-(4-fluoro-1-((2-(trimethylsilyl)ethoxy)methyl)-1H-pyrazol-5-yl)pyrimidin-4-yl)pyrrolidin-3-yl)(methyl)carbamate (Intermediate 118) (189 mg, 96%) as a gum.

The data for Intermediate 118 are in Table 2.

Route 12

Typical Procedure for the Preparation of Pyrazoles, as Exemplified by the Preparation of Intermediate 121, 4-(methylthio)-1H-pyrazole-3-carboxylic acid

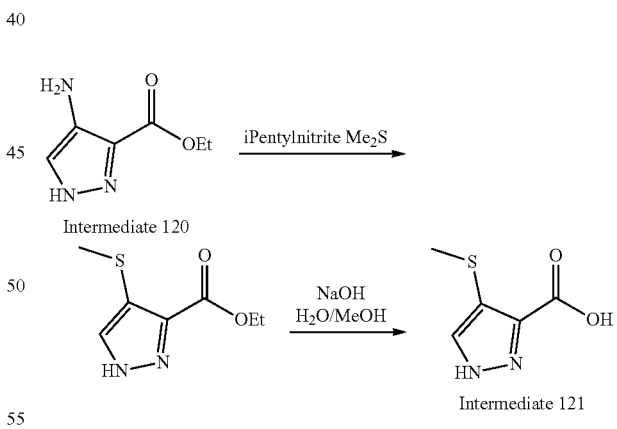

Ethyl 4-amino-1H-pyrazole-3-carboxylate (Intermediate 120) (4.00 g, 2.57 mmol) was dissolved in ACN (40.0 mL), then isopentyl nitrite(10.39 mL) was added followed by addition of dimethyl disulfide (6.87 mL, 7.73 mmol) drop wise under nitrogen at 0° C. and stirred for 1 hr. Then the reaction was heated at 80° C. with stirring for 16 hrs. Once complete consumption of starting material was achieved, the reaction mixture was cooled to about 15° C. and partitioned between H₂O (100 mL) and EtOAc (50 mL), aqueous layer was further extracted with EtOAc (2×50 mL); all organic layers combined, dried (Na₂SO₄) and solvent was removed in vacuo to give crude product. Crude product was purified by column chromatography silica gel (60-120 mesh) and gradient 0 to 50% EtOAc in hexanes. Distilled out solvent to give ethyl 4-(methylthio)-1H-pyrazole-3-carboxylate (3.0 g, 62.5%) as a yellow gum.

LCMS (System 1, Method B): m/z 187 (M+H)+ (ESI +ve), at 1.39 min, 230 nm.

Ethyl 4-(methylthio)-1H-pyrazole-3-carboxylate (3.5 g, 1.87 mmol) was dissolved methanol (25 mL), followed by addition of 2N NaOH aqueous solution (28 mL, 5.63 mmol) drop wise and stirred for 16 hr. at room temperature. The reaction mixture was concentrated, diluted with ice cold water (small quantity), acidified with diluted HCl and the resulting suspension was stirred for further 20-30 min. Solid compound was collected by filtration. The solid was dry under reduce pressure to give 4-(methylthio)-1H-pyrazole-3-carboxylic acid (2.5 g, 84.17%) as a white solid.

The data for Intermediate 121 are in Table 2.
Route 13

Typical Procedure for the Preparation of Pyrazoles, as Exemplified by the Preparation of Intermediate 127, 4-methoxy-5-methyl-1-(tetrahydro-2H-pyran-2-yl)-1H-pyrazole-3-carboxylic acid

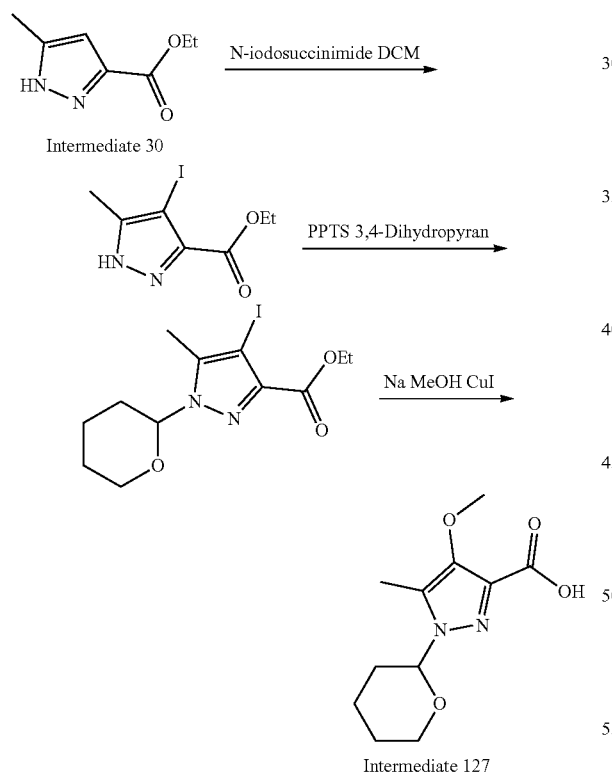

Intermediate 127

Ethyl 5-methyl-1H-pyrazole-3-carboxylate (Intermediate 30) (4.00 g, 25.9 mmol), was dissolved in DCM (100 mL), followed by addition of N-Iodo succinimide (7.09 g, 31.1 mmol) portionwise and stirred at room temperature for 16 hrs. The reaction mixture was partitioned between H2O (60 mL) and EtOAc (30 mL), aqueous layer was further extracted with EtOAc (2×30 mL); combined organic layers combined, dried (Na2SO4) and solvent was removed in vacuum to give crude product. The crude product was purified by column chromatography (60-120 mesh silica gel, 0 to 4% methanol in DCM) to ethyl 4-iodo-5-methyl-1H-pyrazole-3-carboxylate (6.80 g, 93.53%) as a colorless gum.

LCMS (System 1, Method B): m/z 281 (M+H)+ (ESI +ve), at 1.49 min, 229 nm

Ethyl 4-iodo-5-methyl-1H-pyrazole-3-carboxylate (3.10 g, 11.1 mmol) and 3,4-dihydro-2H-pyran (1.39 g, 16.6 mmol) were dissolved in DCM (50.0 mL), followed by addition of Pyridinium p-toluene sulfonate (0.28 g, 1.11 mmol) portion wise and stirred over 16 hrs. at 40° C. The reaction mixture was partitioned between H2O (50 mL) and EtOAc (20 mL), aqueous layer was further extracted with EtOAc (2×20 mL), all organic layers combined, dried (Na2SO4) and solvent was removed in vacuum to give crude product. The crude product was purified by column chromatography (60-120 mesh silica gel, 0 to 2% methanol in DCM) to give ethyl 4-iodo-5-methyl-1-(tetrahydro-2H-pyran-2-yl)-1H-pyrazole-3-carboxylate (3.20 g, 79.40%) as a white solid.

LCMS (System 1, Method B): m/z 365 (M+H)+ (ESI +ve), at 1.73 min, 235 nm

Ethyl 4-iodo-5-methyl-1-(tetrahydro-2H-pyran-2-yl)-1H-pyrazole-3-carboxylate (3.20 g, 8.80 mmol) and CuI (0.50 g, 2.64 mmol) were added to freshly prepared sodium methoxide solution (30.0 mL) and stirred at room temperature for 16 hrs. at 80° C. The reaction mixture was filtered through celite and the filtrate concentrated. The concentrated reaction mixture was dumped in to water (20 mL) and acidify by addition of 1N HCl solution (pH~4.0) and extracted with 10% MeOH in DCM (3×30 mL), all organic layers combined, dried (Na2SO4) and solvent was removed in vacuo to give 4-methoxy-5-methyl-1-(tetrahydro-2H-pyran-2-yl)-1H-pyrazole-3-carboxylic acid (2.45 g, 100% w/w) as a yellow gum.

The data for Intermediate 127 are in Table 2.
General Synthetic Procedures:
Route A Typical Procedure for the Preparation of Pyrimidines as Exemplified by the Preparation of Example 1-1, (R)-4-(3-(methylamino)pyrrolidin-1-yl)-6-(1H-pyrazol-5-yl)pyrimidin-2-amine

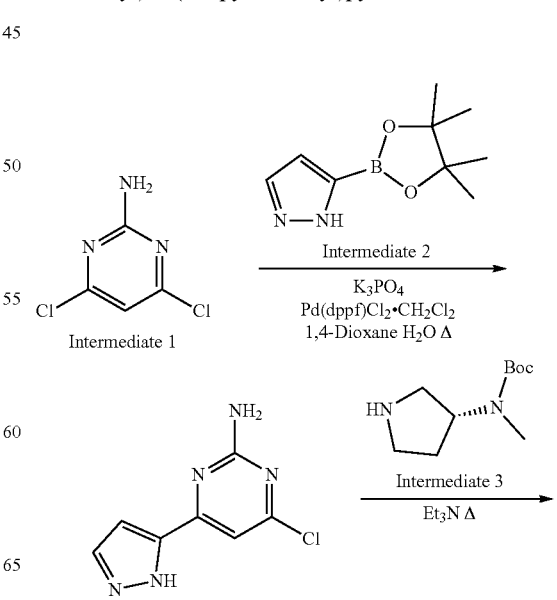

-continued

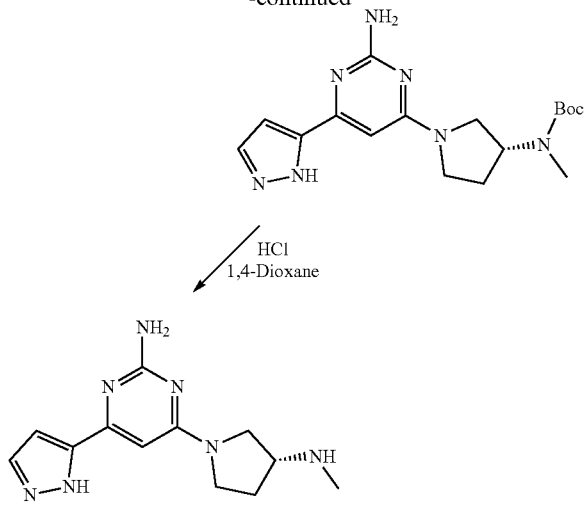

4,6-Dichloropyrimidin-2-amine (Intermediate 1) (250 mg, 1.52 mmol), 5-(4,4,5,5-tetramethyl-1,3,2-dioxaborolan-2-yl)-1H-pyrazole (Intermediate 2) (354 mg, 1.82 mmol) and $K_3PO_4$ (970 mg, 4.50 mmol) were dissolved in 1,4-dioxane (5 mL) and water (0.5 mL) under nitrogen and degassed for 20 min. Then [1,1'-bis(diphenylphosphino)ferrocene]dichloropalladium (II) dichloromethane complex (CAS: 95464-05-4) (124 mg, 0.15 mmol) was added under a nitrogen atmosphere, and the resulting mixture was stirred at 90° C. for 16 h. The reaction mixture was partitioned between $H_2O$ (25 mL) and EtOAc (15 mL), and the aqueous layer was further extracted with EtOAc (2×15 mL). The combined organic layers were dried ($Na_2SO_4$) and the solvent was removed in-vacuo to give the crude product, which was purified by column chromatography (Normal-Phase 60-120 mesh silica gel, 0 to 6% MeOH in DCM) to give 4-chloro-6-(1H-pyrazol-5-yl)pyrimidin-2-amine (75 mg, 25%) as a solid.

LCMS (System 1, Method B): m/z 196 (M+H)$^+$ (ESI +ve), at 1.38 min, 240 nm.

4-Chloro-6-(1H-pyrazol-5-yl)pyrimidin-2-amine (75 mg, 0.38 mmol) and tert-butyl (R)-methyl(pyrrolidin-3-yl)carbamate (Intermediate 3) (76 mg, 0.38 mmol) were dissolved in triethylamine (3 mL) and stirred at 90° C. for 16 h. The reaction mixture was concentrated and then partitioned between $H_2O$ (25 mL) and EtOAc (15 mL). The aqueous layer was further extracted with EtOAc (2×15 mL), and the combined organic layers were dried ($Na_2SO_4$) and solvent was removed in-vacuo to give the crude product, which was purified by column chromatography (Normal-Phase 60-120 mesh silica gel, 0 to 3% MeOH in (R)-(1-(2-amino-6-(1H-pyrazol-5-yl)pyrimidin-4-yl)pyrrolidin-3-DCM) to give tert-butyl yl)(methyl) carbamate (75 mg, 54%) as a solid.

LCMS (System 1, Method B): m/z 360 (M+H)$^+$ (ESI +ve), at 1.44 min, 220 nm.

tert-Butyl (R)-(1-(2-amino-6-(1H-pyrazol-5-yl)pyrimidin-4-yl)pyrrolidin-3-yl)(methyl)carbamate (75 mg, 0.20 mmol) was dissolved in HCl solution in 1,4-dioxane (4 M, 2 mL) under nitrogen at 0° C. and stirred for 3 h at room temperature. The reaction mixture was concentrated and triturated with diethyl ether (2×5 mL) to give the crude product, which was purified by purification Method A to give (R)-4-(3-(methylamino)pyrrolidin-1-yl)-6-(1H-pyrazol-5-yl)pyrimidin-2-amine, Example 1-1 (21 mg, 39%) as a colorless gum. The data for Example 1-1 are in Table 3.

Route B

Typical Procedure for the Preparation of Pyrimidines as Exemplified by the Preparation of Example 1-2, (R)-4-(1-methyl-1H-pyrazol-5-yl)-6-(3-(methylamino)pyrrolidin-1-yl)pyrimidin-2-amine dihydrochloride

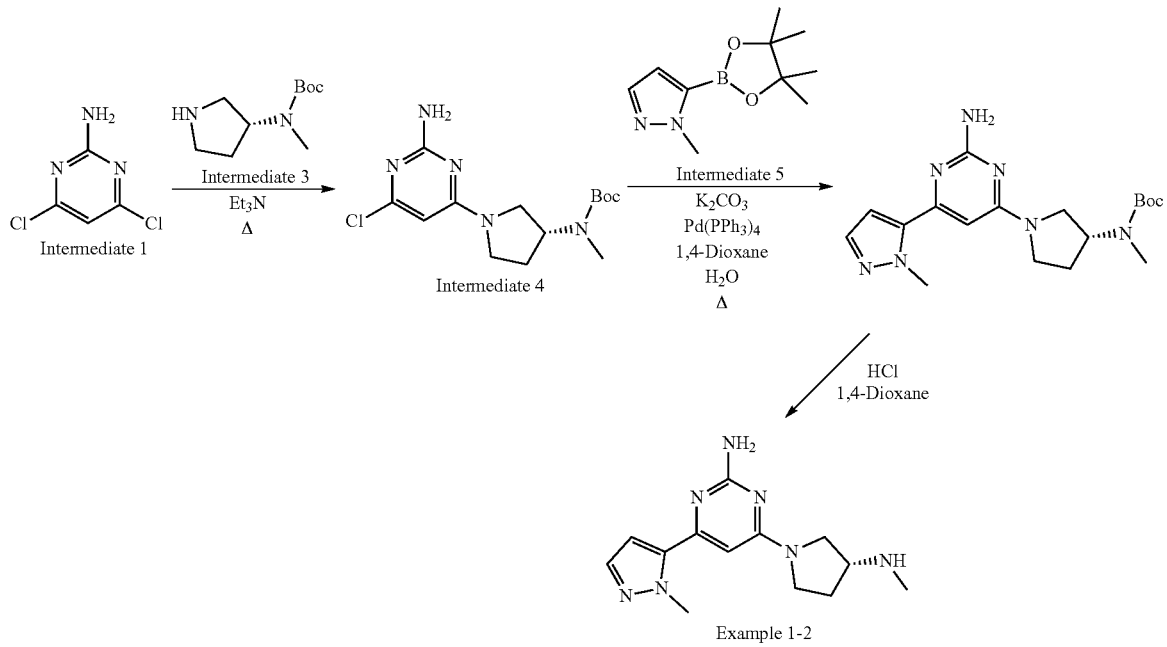 [SMILES: Nc1nc(Cl)cc(Cl)n1 ; CN(C(=O)OC(C)(C)C)[C@@H]1CCNC1 ; CN(C(=O)OC(C)(C)C)[C@@H]1CCN(c2cc(Cl)nc(N)n2)C1 ; Cn1nccc1B1OC(C)(C)C(C)(C)O1 ; CN(C(=O)OC(C)(C)C)[C@@H]1CCN(c2cc(-c3ccnn3C)nc(N)n2)C1 ; CN[C@@H]1CCN(c2cc(-c3ccnn3C)nc(N)n2)C1]

4,6-Dichloropyrimidin-2-amine (Intermediate 1) (5.5 g, 33.5 mmol) and tert-butyl (R)-methyl(pyrrolidin-3-yl)carbamate (Intermediate 3) (7.3 g, 40.2 mmol), were dissolved in triethylamine (13 mL) and the resulting solution was stirred at 90° C. for 3 h. During the reaction process the product precipitated out and it was filtered off, washed with water and dried in-vacuo to give tert-butyl (R)-(1-(2-amino-6-chloropyrimidin-4-yl)pyrrolidin-3-yl)(methyl)carbamate (Intermediate 4) (10.1 g, 92%) as an off-white solid.

The data for Intermediate 4 are in Table 2.

tert-Butyl (R)-(1-(2-amino-6-chloropyrimidin-4-yl)pyrrolidin-3-yl)(methyl)carbamate (Intermediate 4) (150 mg, 0.46 mmol), 1-methyl-5-(4,4,5,5-tetramethyl-1,3,2-dioxaborolan-2-yl)-1H-pyrazole (Intermediate 5) (115 mg, 0.55 mmol) and $K_2CO_3$ (126 mg, 0.92 mmol) were dissolved in 1,4-dioxane min. (5 mL) and water (2 mL) under nitrogen and degassed for 20 Tetrakis(triphenylphosphine)palladium (0) (CAS: 95464-05-4) (26 mg, 0.02 mmol) was added under a nitrogen atmosphere and the resulting mixture was stirred at 90° C. for 16 h. The reaction mixture was partitioned between $H_2O$ (25 mL) and EtOAc (15 mL), and the aqueous layer was further extracted with EtOAc (2×15 mL). The combined organic layers were dried ($Na_2SO_4$) and the solvent was removed in-vacuo to give the crude product, which was purified by column chromatography (Normal-Phase 60-120 mesh silica gel, 0 to 3% MeOH in DCM) to give tert-butyl (R)-(1-(2-amino-6-(1-methyl-1H-pyrazol-5-yl)pyrimidin-4-yl)pyrrolidin-3-yl)(methyl)carbamate (100 mg, 58%) as a gum.

LCMS (System 1, Method A): m/z 374 (M+H)$^+$ (ESI +ve), at 1.40 min, 296 nm.

tert-Butyl (R)-(1-(2-amino-6-(1-methyl-1H-pyrazol-5-yl)pyrimidin-4-yl)pyrrolidin-3-yl)(methyl)carbamate (100 mg, 0.27 mmol) was dissolved in HCl solution in 1,4-dioxane (4 M, 4 mL) under nitrogen and stirred at room temperature for 6 h. The reaction mixture was concentrated and then triturated with diethyl ether (2×10 mL) to give (R)-4-(1-methyl-1H-pyrazol-5-yl)-6-(3-(methylamino)pyrrolidin-1-yl)pyrimidin-2-amine dihydrochloride, Example 1-2 (59 mg, 81%) as a solid.

The data for Example 1-2 are in Table 3.

Route C

Typical Procedure for the Preparation of Pyrimidines as Exemplified by the Preparation of Example 2-1, (R)-4-(1-methyl-1H-pyrazol-3-yl)-6-(3-(methylamino)pyrrolidin-1-yl)pyrimidin-2-amine

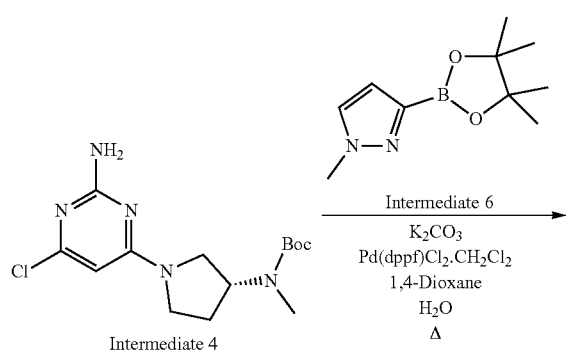

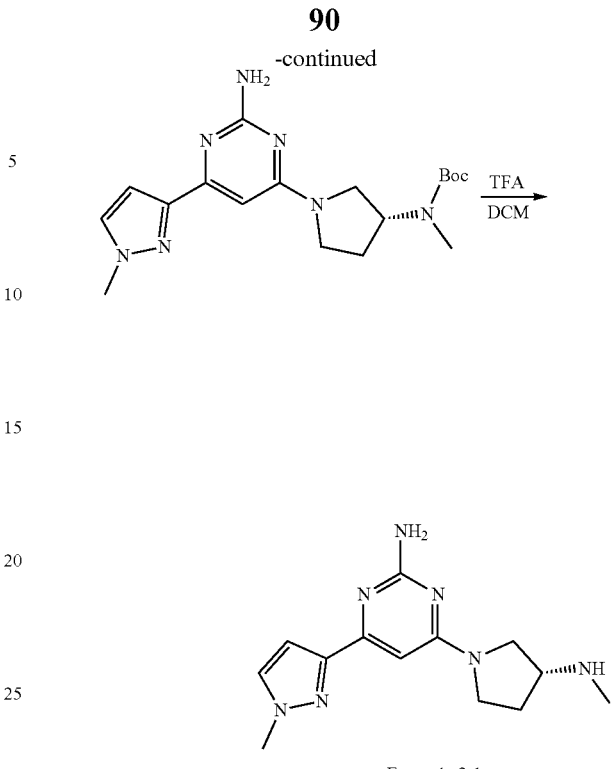

Example 2-1 tert-Butyl (R)-(1-(2-amino-6-chloropyrimidin-4-yl)pyrrolidin-3-yl)(methyl)carbamate (Intermediate 4) (150 mg, 0.45 mmol), 1-methyl-3-(4,4,5,5-tetramethyl-1,3,2-dioxaborolan-2-yl)-1H-pyrazole (Intermediate 6) (114 mg, 0.54 mmol) and $K_3PO_4$ (291 mg, 0.13 mmol) were dissolved in 1,4-dioxane (12 mL) and water (3 mL) under nitrogen and degassed for 20 min. Then [1,1'-bis(diphenylphosphino)ferrocene]dichloropalladium (II) dichloromethane complex (CAS: 95464-05-4) (37 mg, 0.04 mmol) was added under a nitrogen atmosphere and the resulting mixture was stirred at 90° C. for 16 h. The reaction mixture was partitioned between $H_2O$ (40 mL) and EtOAc (25 mL), and the aqueous layer was further extracted with EtOAc (3×25 mL). The organic layers were combined, dried ($Na_2SO_4$) and the solvent was removed in-vacuo to give the crude product, which was purified by column chromatography (Normal-Phase activated alumina, 2% to 4% MeOH in DCM) to give tert-butyl (R)-(1-(2-amino-6-(1-methyl-1H-pyrazol-3-yl)pyrimidin-4-yl)pyrrolidin-3-yl)(methyl)carbamate (169 mg, 99%) as a solid.

LCMS (System 2, Method E): m/z 374 (M+H)$^+$ (ESI +ve), at 3.31 min, 254 nm.

tert-butyl (R)-(1-(2-amino-6-(1-methyl-1H-pyrazol-3-yl)pyrimidin-4-yl)pyrrolidin-3-yl)(methyl)carbamate (169 mg, 0.45 mmol) was dissolved in a mixture of TFA (2 mL) and DCM (4 mL) under nitrogen and stirred at room temperature for 2 h. The reaction mixture was concentrated and then triturated with pentane (2×2 mL) to give the crude product, which was purified by purification Method B to give (R)-4-(1-methyl-1H-pyrazol-3-yl)-6-(3-(methylamino)pyrrolidin-1-yl)pyrimidin-2-amine, Example 2-1 (94 mg, 76%) as a solid.

The data for Example 2-1 are in Table 3.

Route D

Typical Procedure for the Preparation of Pyrimidines as Exemplified by the Preparation of Example 2-2, (R)-4-(1-(difluoromethyl)-1H-pyrazol-3-yl)-6-(3-(methylamino)pyrrolidin-1-yl)pyrimidin-2-amine dihydrochloride

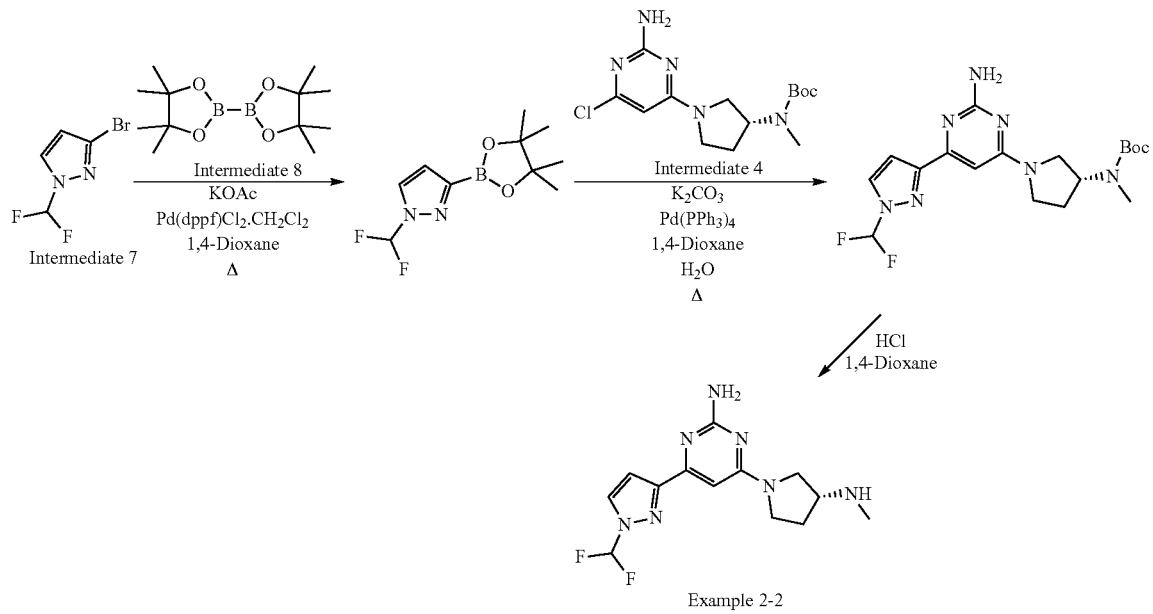

Example 2-2

A mixture of [1,1'-bis(diphenylphosphino)ferrocene]dichloropalladium (II) dichloromethane complex (CAS: 95464-05-4) (61 mg, 0.08 mmol), bis(pinacolato)diboron (Intermediate 8) (267 mg, 1.05 mmol), 3-bromo-1-(difluoromethyl)-1H-pyrazole (Intermediate 7) (148 mg, 0.75 mmol) and potassium acetate (294 mg, 3 mmol) in 1,4-dioxane (2.5 mL) was heated to 110° C. and maintained at that temperature overnight. The reaction mixture was concentrated, and the product was used directly in the next synthetic step without further isolation or purification. Assumed 100% yield.

LCMS (System 4, Method F): m/z 245 (M+H)$^+$ (ESI +ve), at 0.14 min, 254 nm.

A mixture of potassium carbonate (138 mg, 1.0 mmol), tetrakis(triphenylphosphine)palladium (0) (CAS: 95464-05-4) (58 mg, 0.05 mmol), 1-(difluoromethyl)-3-(4,4,5,5-tetramethyl-1,3,2-dioxaborolan-2-yl)pyrazole (183 mg, 0.75 mmol, assumed yield from previous step) and tert-butyl (R)-(1-(2-amino-6-chloropyrimidin-4-yl)pyrrolidin-3-yl)(methyl)carbamate (Intermediate 4) (164 mg, 0.50 mmol) in 1,4-dioxane (2.2 mL) and water (0.26 mL) was heated to 110° C. and maintained at that temperature overnight. The reaction mixture was then partitioned between EtOAc (5 mL) and water (5 mL) and the phases were separated. The aqueous phase was further extracted with EtOAc (3×5 mL) and all the organic phases were combined and concentrated to give the crude product, which was purified by purification Method C to give tert-butyl (R)-(1-(2-amino-6-(1-(difluoromethyl)-1H-pyrazol-3-yl)pyrimidin-4-yl)pyrrolidin-3-yl)(methyl)carbamate (83 mg, 41%) as a solid.

LCMS (System 4, Method F): m/z 410 (M+H)$^+$ (ESI +ve), at 2.06 min, 254 nm. tert-Butyl (R)-(1-(2-amino-6-(1-(difluoromethyl)-1H-pyrazol-3-yl)pyrimidin-4-yl)pyrrolidin-3-yl)(methyl)carbamate (83 mg, 0.20 mmol) was dissolved in DCM (2 mL), HCl solution in 1,4-dioxane (4 M, 0.25 mL, 1.01 mmol) was added and the resulting mixture was stirred at RT overnight. After this time the white precipitate was isolated to give 4-[1-(difluoromethyl)pyrazol-3-yl]-6-[(3R)-3-(methylamino)pyrrolidin-1-yl]pyrimidin-2-amine dihydrochloride, Example 2-2 (69 mg, 98%).

The data for Example 2-2 are in Table 3.

Route E

Typical Procedure for the Preparation of Pyrimidines as Exemplified by the Preparation of Example 3-1, (R)-4-(3-methyl-1H-pyrazol-5-yl)-6-(3-(methylamino)pyrrolidin-1-yl)pyrimidin-2-amine

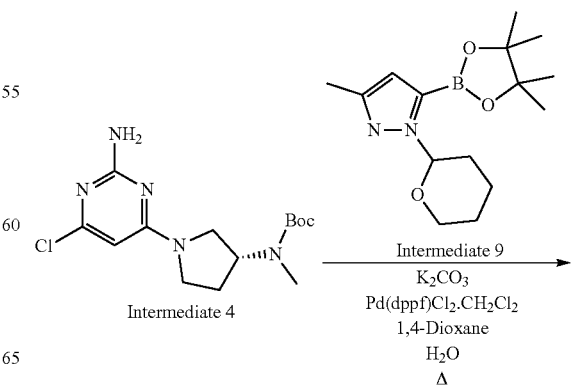

-continued

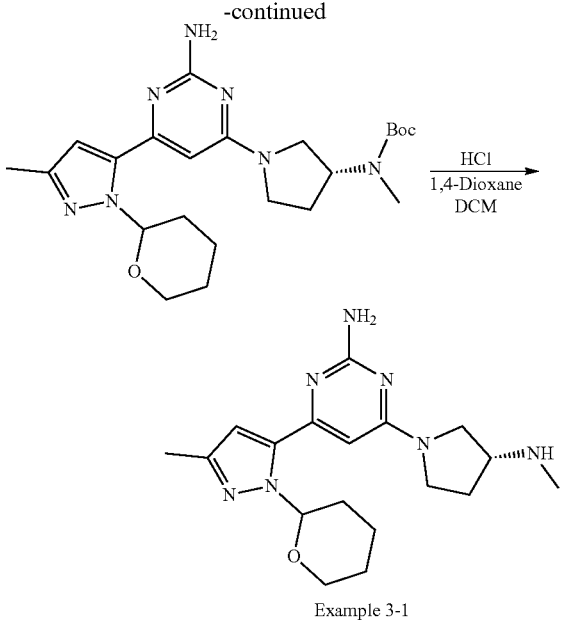

Example 3-1 tert-Butyl (R)-(1-(2-amino-6-chloropyrimidin-4-yl)pyrrolidin-3-yl)(methyl)carbamate (Intermediate 4) (1.0 g, 3.0 mmol), 3-methyl-1-(tetrahydro-2H-pyran-2-yl)-5-(4,4,5,5-tetramethyl-1,3,2-dioxaborolan-2-yl)-1H-pyrazole (Intermediate 9) (1.06 g, 3.63 mmol) and $K_3PO_4$ (1.90 g, 9.0 mol) were dissolved in 1,4-dioxane (16 mL) and water (4 mL) under nitrogen and degassed for 20 min. Then [1,1'-bis(diphenylphosphino)ferrocene]dichloropalladium (II) dichloromethane complex (CAS: 95464-05-4) (245 mg, 0.3 mol) was added under a nitrogen atmosphere and the resulting mixture was stirred at 90° C. for 16 h. The reaction mixture was partitioned between $H_2O$ (50 mL) and EtOAc (30 mL) and the aqueous layer was further extracted with EtOAc (3×50 mL). The combined organic layers were dried ($Na_2SO_4$) and the solvent was removed in-vacuo to give the crude product, which was purified by column chromatography (Normal-Phase neutral alumina, 9% MeOH in DCM) to give tert-butyl ((3R)-1-(2-amino-6-(3-methyl-1-(tetrahydro-2H-pyran-2-yl)-1H-pyrazol-5-yl)pyrimidin-4-yl)pyrrolidin-3-yl)(methyl)carbamate (1.2 g, 86%) as a solid.

LCMS (System 2, Method E): m/z 458 (M+H)⁺ (ESI +ve), at 3.96 min, 313 nm.

tert-Butyl ((3R)-1-(2-amino-6-(3-methyl-1-(tetrahydro-2H-pyran-2-yl)-1H-pyrazol-5-yl)pyrimidin-4-yl)pyrrolidin-3-yl)(methyl)carbamate (1.2 g, 0.26 mmol) was dissolved in DCM (20 mL) and cooled to 0° C. HCl solution in 1,4-dioxane (4 M, 25 mL) was added dropwise and the resulting reaction mixture was stirred at 25° C. for 2 h. The solvents were removed in-vacuo and the residue was co-evaporated from toluene (2×30 mL) to give the crude product, which was purified by purification Method D to give (R)-4-(3-methyl-1H-pyrazol-5-yl)-6-(3-(methylamino)pyrrolidin-1-yl)pyrimidin-2-amine, Example 3-1 (520 mg, 73%) as a solid.

The data for Example 3-1 are in Table 3.

Route F

Typical Procedure for the Preparation of Pyrimidines as Exemplified by the Preparation of Example 3-3, (R)-4-(3-(difluoromethyl)-1H-pyrazol-5-yl)-6-(3-(methylamino)pyrrolidin-1-yl)pyrimidin-2-amine

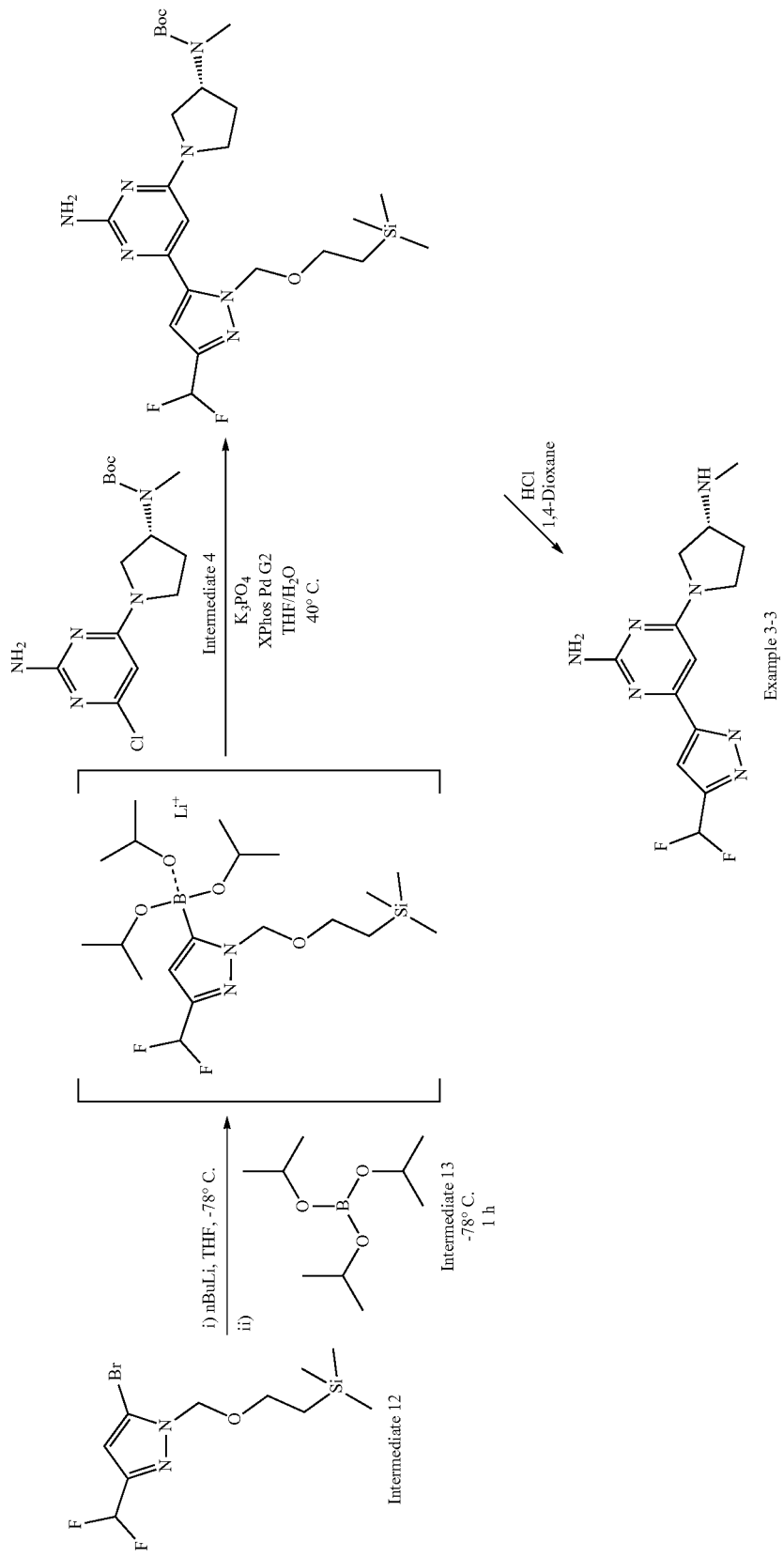

To a nitrogen purged microwave vial was added 5-bromo-3-(difluoromethyl)-1-((2-(trimethylsilyl)ethoxy)methyl)-1H-pyrazole (Intermediate 12) (100 mg, 0.31 mmol) dissolved in THF (0.40 mL) and the solution was cooled to −78° C. under an atmosphere of nitrogen. n-Butyllithium solution in hexanes (2.5 M, 0.13 mL, 0.34 mmol) was then added dropwise to the solution before the dropwise addition of triisopropyl borate (Intermediate 13) (0.08 mL, 0.34 mmol). The reaction mixture was then stirred at −78° C. for 1 h. Aqueous K₃PO₄ (0.5 M, 0.79 mL, 0.40 mmol) was then added to the reaction mixture followed by tert-butyl (R)-(1-(2-amino-6-chloropyrimidin-4-yl)pyrrolidin-3-yl)(methyl)carbamate (Intermediate 4) (70 mg, 0.21 mmol) and XPhos Pd G2 precatalyst (CAS: 1310584-14-5) (7 mg, 0.009 mmol). The microwave vial was then sealed and heated to 40° C. (conventional heating) with stirring for 18 h. The reaction mixture was added to a solution of water (20 mL) and saturated aqueous NH₄Cl (0.4 mL) and extracted using ethyl acetate. The aqueous layer was then re-extracted using ethyl acetate (×2). The combined organic extracts were filtered through a phase separator and concentrated under reduced pressure, and the residue purified using column chromatography (basic silica, 0-50% ethyl acetate in petroleum ether) to give the crude product (37 mg) as a solid. The solid was further purified by purification Method E to give tert-butyl (R)-(1-(2-amino-6-(3-(difluoromethyl)-1-((2-(trimethylsilyl)ethoxy)methyl)-1H-pyrazol-5-yl)pyrimidin-4-yl)pyrrolidin-3-yl)(methyl)carbamate (9 mg, 5%).

LCMS (System 4, Method F): m/z 540 (M+H)⁺ (ESI +ve), at 2.70 min, 254 nm.

To a solution of tert-butyl (R)-(1-(2-amino-6-(3-(difluoromethyl)-1-((2-(trimethylsilyl)ethoxy)methyl)-1H-pyrazol-5-yl)pyrimidin-4-yl)pyrrolidin-3-yl)(methyl)carbamate (8 mg, 0.01 mmol) dissolved in 1,4-dioxane (0.55 mL) was added HCl solution in 1,4-dioxane (4 M, 0.05 mL, 0.22 mmol). The reaction mixture was stirred at room temperature for 6 h, then concentrated under reduced pressure and the residue co-evaporated from toluene. The crude product was then purified using reversed phase column chromatography (C18 silica, 0-10% MeCN in 0.2% NH₃ in water) to give (R)-4-(3-(difluoromethyl)-1H-pyrazol-5-yl)-6-(3-(methylamino)pyrrolidin-1-yl)pyrimidin-2-amine, Example 3-3 (2 mg, 47%).

The data for Example 3-3 are in Table 3.

Route G

Typical Procedure for the Preparation of Pyrimidines as Exemplified by the Preparation of Example 3-4, (R)-4-(3-(difluoromethyl)-1H-pyrazol-5-yl)-6-(3-(methylamino)pyrrolidin-1-yl)pyrimidin-2-amine ditrifluoroacetate

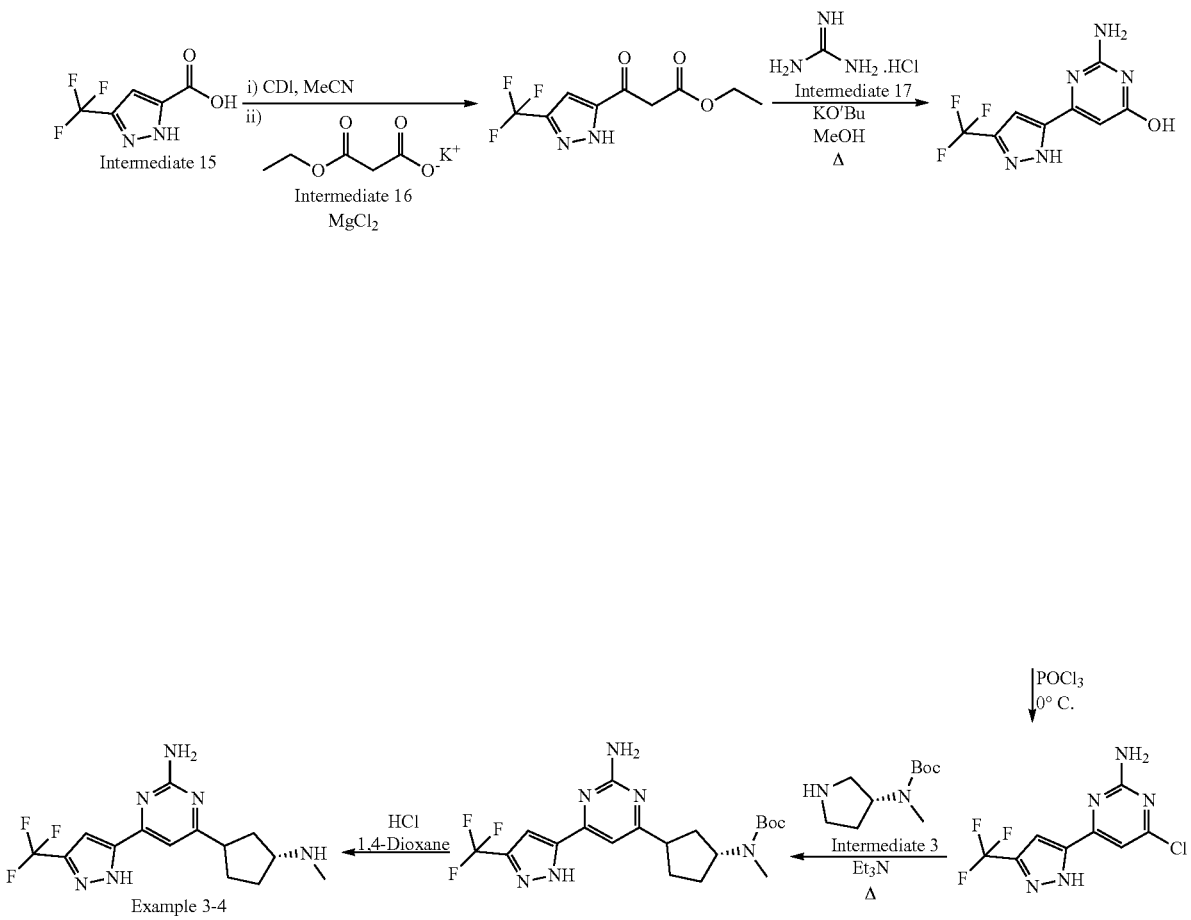

3-(Trifluoromethyl)-1H-pyrazole-5-carboxylic acid (Intermediate 15) (1.30 g, 7.20 mmol) was dissolved in acetonitrile (20 mL), CDI (1.40 g, 8.66 mmol) was added portionwise and the resulting mixture was stirred at room temperature for 2 h. Potassium 3-ethoxy-3-oxopropanoate (Intermediate 16) (1.22 g, 7.20 mmol) and MgCl$_2$ (823 mg, 7.20 mmol) were then added and the resulting reaction mixture was stirred at room temperature for 14 h. The mixture was concentrated in-vacuo, the residue was partitioned between H$_2$O (40 mL) and EtOAc (30 mL) and the layers were separated. The aqueous layer was further extracted with EtOAc (2×30 mL), the combined organic layers were dried (Na$_2$SO$_4$) and the solvent was removed in-vacuo. The crude product was purified by triturating with pentane (decanting off the solvent) and dried under high vacuum to give ethyl 3-oxo-3-(3-(trifluoromethyl)-1H-pyrazol-5-yl)propanoate (1.20 g, 67%) as a gum.

LCMS (System 2, Method E): m/z 249 (M−H)⁻ (ESI −ve), at 4.47 min, 241 nm.

Ethyl 3-oxo-3-(3-(trifluoromethyl)-1H-pyrazol-5-yl)propanoate (1.20 g, 4.80 mmol) and guanidine hydrochloride (Intermediate 17) (1.37 g, 14.4 mmol) were dissolved in methanol (20 mL) under nitrogen at 0° C. and stirred for 10 min. Potassium tert-butoxide (806 mg, 7.20 mmol) was added slowly under a nitrogen atmosphere and the resulting reaction mixture was stirred at 60° C. for 16 h. The organic solvent was removed in-vacuo to give the crude product, which was purified by triturating with pentane (decanting off the solvent) and dried under high vacuum to give 2-amino-6-(3-(trifluoromethyl)-1H-pyrazol-5-yl)pyrimidin-4-ol (2.0 g, crude) as a gum.

LCMS (System 2, Method E): m/z 246 (M+H)⁺ (ESI +ve), at 3.47 min, 237 nm.

A mixture of 2-amino-6-(3-(trifluoromethyl)-1H-pyrazol-5-yl)pyrimidin-4-ol (2.0 g, 8.16 mmol) and POCl$_3$ (5 mL) was stirred at 0° C. for 18 h. The reaction mixture was poured onto a mixture of ice and aqueous NaHCO$_3$, then partitioned between H$_2$O (50 mL) and EtOAc (40 mL) and the phases were separated. The aqueous phase was further extracted with EtOAc (2×40 mL) and the organic layers were all combined, dried (Na$_2$SO$_4$) and the solvent was removed in-vacuo. The residue was purified by column chromatography (Normal-Phase neutral activated alumina, 20% to 30% MeOH in DCM) to give 4-chloro-6-(3-(trifluoromethyl)-1H-pyrazol-5-yl)pyrimidin-2-amine (350 mg, 16%) as a gum.

LCMS (System 2, Method E): m/z 264/266 (M+H)⁺ (ESI +ve), at 4.57 min, 239 nm.

4-Chloro-6-(3-(trifluoromethyl)-1H-pyrazol-5-yl)pyrimidin-2-amine (200 mg, 0.76 mmol) was dissolved in triethylamine (5 mL) and tert-butyl (R)-methyl(pyrrolidin-3-yl)carbamate (Intermediate 3) (228 mg, 1.14 mmol) was added. The resulting reaction mixture was stirred at 90° C. for 6 h, then partitioned between H$_2$O (40 mL) and EtOAc (30 mL) and the phases were separated. The aqueous layer was further extracted with EtOAc (2×30 mL), the combined organic layers were dried (Na$_2$SO$_4$) and the solvent was removed in-vacuo. The residue was purified by column chromatography (Normal-Phase neutral activated alumina, 5% to 10% MeOH in EtOAc) to give tert-butyl (R)-(1-(2-amino-6-(3-(trifluoromethyl)-1H-pyrazol-5-yl)pyrimidin-4-yl)pyrrolidin-3-yl)(methyl)carbamate (315 mg, 97%) as a gum.

LCMS (System 2, Method E): m/z 428 (M+H)⁺ (ESI +ve), at 4.13 min, 243 nm.

tert-Butyl (R)-(1-(2-amino-6-(3-(trifluoromethyl)-1H-pyrazol-5-yl)pyrimidin-4-yl)pyrrolidin-3-yl)(methyl)carbamate (310 mg, 0.73 mmol) was dissolved 1,4-dioxane (3 mL) and the solution was cooled to 0° C. HCl solution in 1,4-dioxane (4 M, 8 mL) was added and the resulting reaction mixture was stirred at room temperature for 7 h. The reaction mixture was concentrated in-vacuo and the residue was triturated with pentane (2×3 mL) to give the crude product as an HCl salt. The crude HCl salt was purified by purification Method F to give (R)-4-(3-(methylamino)pyrrolidin-1-yl)-6-(3-(trifluoromethyl)-1H-pyrazol-5-yl)pyrimidin-2-amine ditrifluoroacetate salt, Example 3-4 (60 mg, 19%) as a gum.

The data for Example 3-4 are in Table 3.
Route H

Typical Procedure for the Preparation of Pyrimidines as Exemplified by the Preparation of Example 4-1, (R)-4-(4-methyl-1H-pyrazol-5-yl)-6-(3-(methylamino)pyrrolidin-1-yl)pyrimidin-2-amine

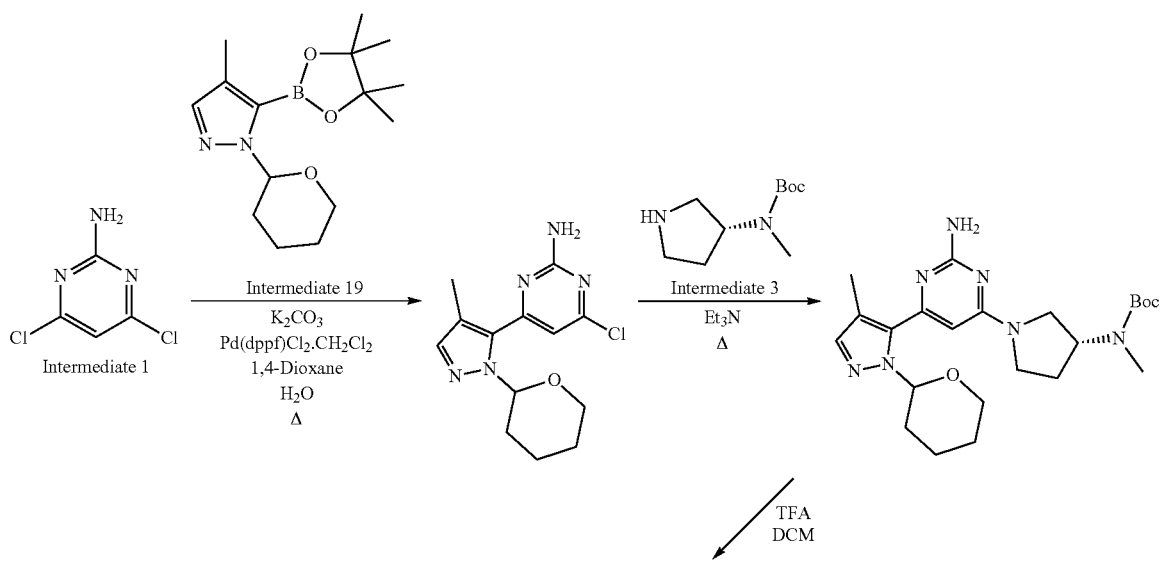

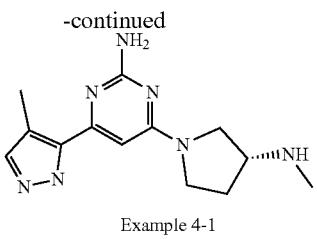

Example 4-1

4,6-Dichloropyrimidin-2-amine (Intermediate 1) (250 mg, 1.52 mmol), 4-methyl-1-(tetrahydro-2H-pyran-2-yl)-5-(4,4,5,5-tetramethyl-1,3,2-dioxaborolan-2-yl)-1H-pyrazole (Intermediate 19) (443 mg, 1.52 mmol) and $K_2CO_3$ (629 mg, 4.56 mmol) were dissolved in 1,4-dioxane (5 mL) and water (5 mL) under nitrogen and degassed for 20 min. Then [1,1'-bis(diphenylphosphino)ferrocene]dichloropalladium (II) dichloromethane complex (CAS: 95464-05-4) (124 mg, 0.15 mmol) was added under a nitrogen atmosphere and the resulting mixture was stirred at 90° C. for 16 h. The reaction mixture was partitioned between $H_2O$ (40 mL) and EtOAc (25 mL), and the aqueous layer was further extracted with EtOAc (3×25 mL). The combined organic layers were dried ($Na_2SO_4$) and the solvent was removed in-vacuo to give the crude product, which was purified by column chromatography (Normal-Phase activated $Al_2O_3$, 30% ethyl acetate in hexanes) to give 4-chloro-6-(4-methyl-1-(tetrahydro-2H-pyran-2-yl)-1H-pyrazol-5-yl)pyrimidin-2-amine (255 mg, 57%) as a solid.

LCMS (System 2, Method E): m/z 294 $(M+H)^+$ (ESI +ve), at 3.53 min, 234 nm.

4-Chloro-6-(4-methyl-1-(tetrahydro-2H-pyran-2-yl)-1H-pyrazol-5-yl)pyrimidin-2-amine (255 mg, 0.87 mmol) and tert-butyl (R)-methyl(pyrrolidin-3-yl)carbamate (Intermediate 3) was dissolved in TEA (4 mL) under a nitrogen atmosphere and the resulting reaction mixture was heated to 130° C. in a CEM microwave and stirred at that temperature for 12 h. The reaction mixture was then partitioned between $H_2O$ (25 mL) and EtOAc (15 mL), and the aqueous layer was further extracted with EtOAc (2×15 mL). The combined organic layers were dried ($Na_2SO_4$) and the solvent was removed in-vacuo to give the crude product, which was purified by column chromatography (Normal-Phase, neutral activated alumina, 1 to 2% MeOH in DCM) to give tert-butyl ((3R)-1-(2-amino-6-(4-methyl-1-(tetrahydro-2H-pyran-2-yl)-1H-pyrazol-5-yl)pyrimidin-4-yl)pyrrolidin-3-yl)(methyl)carbamate (101 mg, 25%) as a gum.

LCMS (System 2, Method E): m/z 458 $(M+H)^+$ (ESI +ve), at 3.98 min, 278 nm.

tert-Butyl ((3R)-1-(2-amino-6-(4-methyl-1-(tetrahydro-2H-pyran-2-yl)-1H-pyrazol-5-yl)pyrimidin-4-yl)pyrrolidin-3-yl)(methyl)carbamate (100 mg, 0.22 mmol) was dissolved in DCM (5 mL), TFA (0.5 mL) was added at 0° C. under an atmosphere of nitrogen and the resulting mixture was stirred at room temperature for 18 h. The reaction mixture was concentrated and the residue was triturated with pentane (2×2 mL) to give the crude product, which was purified by purification Method G to give (R)-4-(4-methyl-1H-pyrazol-5-yl)-6-(3-(methylamino)pyrrolidin-1-yl)pyrimidin-2-amine, Example 4-1 (17 mg, 28%) as a solid.

The data for Example 4-1 are in Table 3.

Route I

Typical Procedure for the Preparation of Pyrimidines as Exemplified by the Preparation of Example 4-2, (R)-4-(4-ethyl-1H-pyrazol-5-yl)-6-(3-(methylamino)pyrrolidin-1-yl)pyrimidin-2-amine

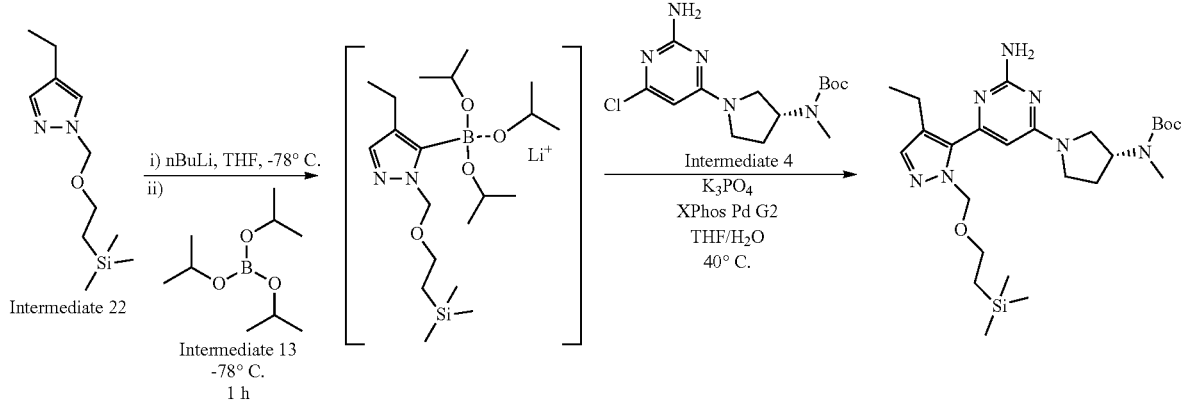

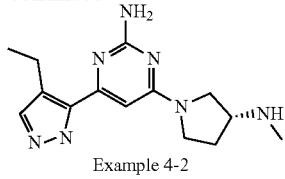

Example 4-2

To a nitrogen purged microwave vial was added 4-ethyl-1-((2-(trimethylsilyl)ethoxy)methyl)-1H-pyrazole (Intermediate 22) (500 mg, 2.21 mmol) dissolved in THF (2.9 mL) and the solution was cooled to −78° C. To this solution was then added n-butyllithium solution in hexanes (2.5 M, 0.97 mL, 2.43 mmol), dropwise over a period of 10 minutes, followed by triisopropyl borate (Intermediate 13) (0.56 mL, 2.43 mmol) added in a similar dropwise manner. The reaction mixture was stirred at −78° C. for 1 h, then aqueous $K_3PO_4$ (0.5 M, 5.74 mL, 2.87 mmol) was added, followed by tert-butyl (R)-(1-(2-amino-6-chloropyrimidin-4-yl)pyrrolidin-3-yl)(methyl)carbamate (Intermediate 4) (217 mg, 0.66 mmol) and XPhos Pd G2 precatalyst (CAS: 1310584-14-5) (52 mg, 0.04 mmol). The microwave vial was then sealed and heated to 40° C. (conventional heating) with stirring for 19 h. The reaction mixture was added to a solution of water (49 mL) and saturated aqueous $NH_4Cl$ (1 mL) and extracted using ethyl acetate. The aqueous layer was then re-extracted using ethyl acetate (2×50 mL). The combined organic extracts were then filtered through a phase separator, concentrated under reduced pressure and the residue was purified using column chromatography (silica, 0-100% ethyl acetate in petroleum ether) to give tert-butyl (R)-(1-(2-amino-6-(4-ethyl-1-((2-(trimethylsilyl)ethoxy)methyl)-1H-pyrazol-5-yl)pyrimidin-4-yl)pyrrolidin-3-yl)(methyl)carbamate (87 mg, 25%).

LCMS (System 4, Method F): m/z 518 (M+H)$^+$ (ESI +ve), at 2.58 min, 254 nm.

To a solution of tert-butyl (R)-(1-(2-amino-6-(4-ethyl-1-((2-(trimethylsilyl)ethoxy)methyl)-1H-pyrazol-5-yl)pyrimidin-4-yl)pyrrolidin-3-yl)(methyl)carbamate (87 mg, 0.17 mmol) dissolved in 1,4-dioxane (4 mL) was added HCl solution in 1,4-dioxane (4 M, 1.26 mL, 5.04 mmol). The reaction mixture was stirred at room temperature for 45 min, then concentrated under reduced pressure and the residue co-evaporated from toluene. The residue was purified by purification Method H to give (R)-4-(4-ethyl-1H-pyrazol-5-yl)-6-(3-(methylamino)pyrrolidin-1-yl)pyrimidin-2-amine, Example 4-2 (16 mg, 33%).

The data for Example 4-2 are in Table 3.

Route J

Typical Procedure for the Preparation of Pyrimidines as Exemplified by the Preparation of Example 4-3, (R)-4-(4-chloro-1H-pyrazol-5-yl)-6-(3-(methylamino)pyrrolidin-1-yl)pyrimidin-2-amine

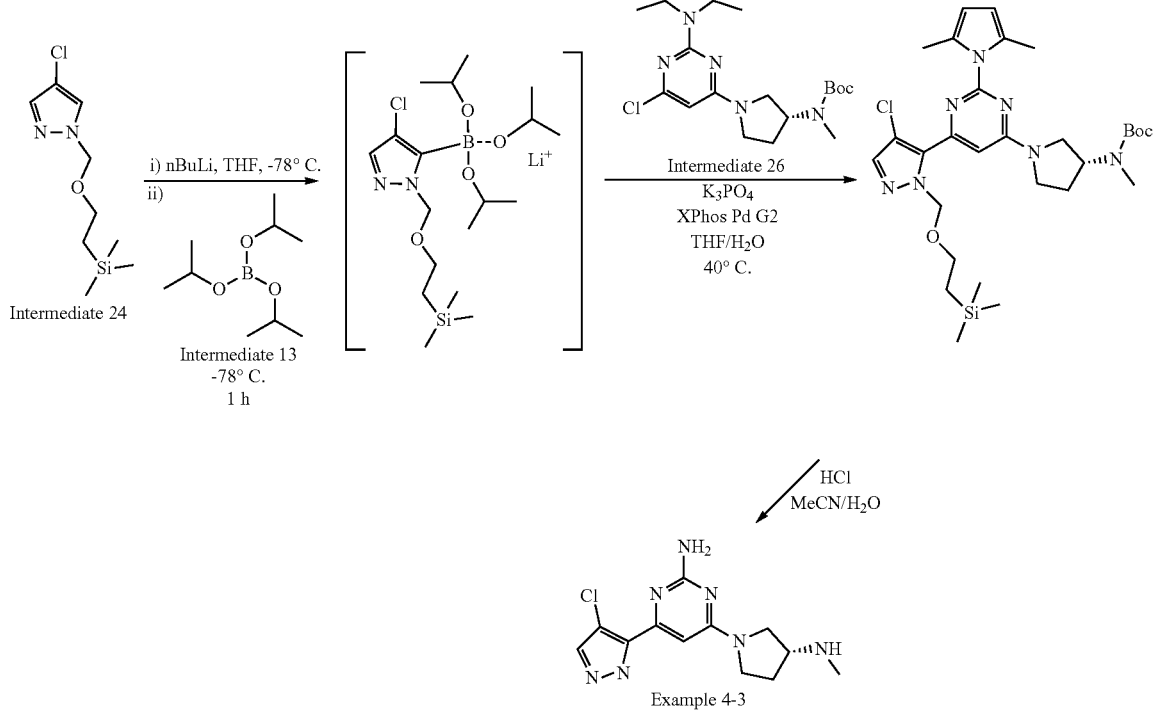

Example 4-3

To a nitrogen purged microwave vial was added 4-chloro-1-((2-(trimethylsilyl)ethoxy)methyl)-1H-pyrazole (Intermediate 24) (646 mg, 2.78 mmol) dissolved in THF (3.7 mL). The solution was cooled to −78° C. and n-butyllithium solution in hexanes (2.5 M, 1.22 mL, 3.05 mmol) was added dropwise over a period of 10 minutes before the addition of triisopropyl borate (Intermediate 13) (0.7 mL, 3.05 mmol), added in a similar dropwise manner. The reaction mixture was stirred at −78° C. for 1 hour. Aqueous aqueous $K_3PO_4$ (0.5 M, 7.22 mL, 3.61 mmol) was then added to the reaction mixture followed by tert-butyl (R)-(1-(6-chloro-2-(2,5-dimethyl-1H-pyrrol-1-yl)pyrimidin-4-yl)pyrrolidin-3-yl)(methyl)carbamate (Intermediate 26) (338 mg, 0.83 mmol) and XPhos Pd G2 precatalyst (CAS: 1310584-14-5) (66 mg, 0.08 mmol). The microwave vial was then sealed and heated to 40° C. conventionally with stirring for 1.5 h. The reaction mixture was added to a solution of water (49 mL) and saturated aqueous $NH_4Cl$ (1 mL) and extracted using ethyl acetate (50 mL). The aqueous layer was further extracted with ethyl acetate (2×50 mL) and the combined organic phases were filtered through a phase separator and concentrated under reduced pressure. The residue was then purified using column chromatography (silica, 0-25% ethyl acetate in petroleum ether) to give tert-butyl (R)-(1-(6-(4-chloro-1-((2-(trimethylsilyl)ethoxy)methyl)-1H-pyrazol-5-yl)-2-(2,5-dimethyl-1H-pyrrol-1-yl)pyrimidin-4-yl)pyrrolidin-3-yl)(methyl)carbamate (440 mg, 87%).

LCMS (System 4, Method F): m/z 602/604 (M+H)$^+$ (ESI +ve), at 3.13 min, 254 nm.

To a solution of give tert-butyl (R)-(1-(6-(4-chloro-1-((2-(trimethylsilyl)ethoxy)methyl)-1H-pyrazol-5-yl)-2-(2,5-dimethyl-1H-pyrrol-1-yl)pyrimidin-4-yl)pyrrolidin-3-yl)(methyl)carbamate (50 mg, 0.08 mmol) dissolved in MeCN (0.83 mL) was added aqueous HCl (4 M, 1.25 mL, 5 mmol). The reaction mixture was stirred at room temperature for 2.5 h and at 40° C. for 2 h. An identical reaction on the same scale was run in parallel, whereby the reaction mixture was stirred at room temperature overnight. The two reaction mixtures were combined and concentrated under reduced pressure. The residue was co-evaporated from toluene to remove traces of water and then purified by purification Method I to give (R)-4-(4-chloro-1H-pyrazol-5-yl)-6-(3-(methylamino)pyrrolidin-1-yl)pyrimidin-2-amine, Example 4-3 (3.7 mg, 8%).

The data for Example 4-3 are in Table 3.

Route K

Typical Procedure for the Preparation of Pyrimidines as Exemplified by the Preparation of Example 4-4, (R)-4-(4-methoxy-1H-pyrazol-5-yl)-6-(3-(methylamino)pyrrolidin-1-yl)pyrimidin-2-amine

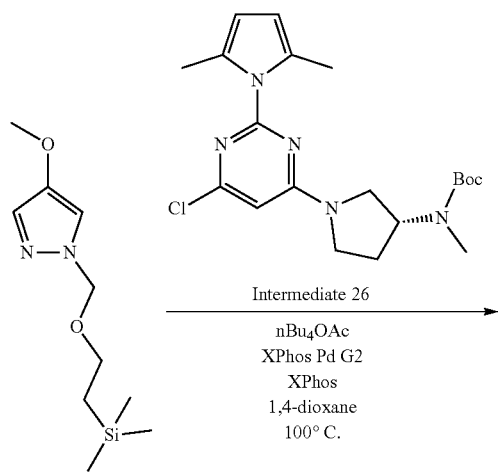

Intermediate 26 nBu₄OAc
XPhos Pd G2
XPhos
1,4-dioxane
100° C.

Intermediate 28

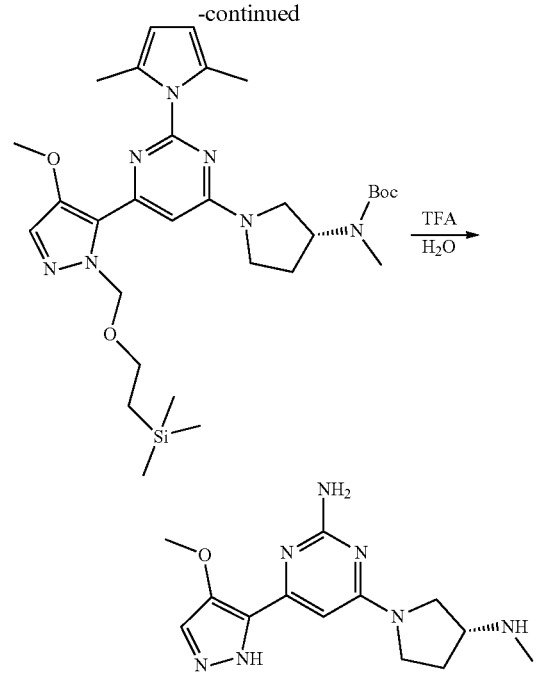

Example 4-4

1, 4-Dioxane was degassed by passing a stream of nitrogen though the liquid for 15 min. A 5 mL microwave vial containing a stirrer bar was flushed with a stream of nitrogen for 5 min, and then stoppered. To the microwave vial was added (in this order): tert-butyl (R)-(1-(6-chloro-2-(2,5-dimethyl-1H-pyrrol-1-yl)pyrimidin-4-yl)pyrrolidin-3-yl)(methyl)carbamate (Intermediate 26) (107 mg, 0.26 mmol), 4-methoxy-1-((2-(trimethylsilyl)ethoxy)methyl)-1H-pyrazole (Intermediate 28) (102 mg, 0.45 mmol), tetrabutylammonium acetate (198 mg, 0.66 mmol) (very hygroscopic!), XPhos (CAS: 564483-18-7) (13 mg, 0.03 mmol) and XPhos Pd G2 precatalyst (CAS: 1310584-14-5) (9 mg, 0.01 mmol). The vial was briefly flushed again with a stream of nitrogen and the degassed 1,4-dioxane (3 mL) was added. The vial was sealed and heated with stirring at 100° C. on a hotplate for 66 h. The reaction was repeated on a similar scale and the two reaction solutions were combined using ethyl acetate and concentrated onto flash silica (10 mL) in-vacuo. The resulting powder was purified by flash chromatography (SiO$_2$, 20%-60% EtOAc in isohexane) to give tert-butyl (R)-(1-(2-(2,5-dimethyl-1H-pyrrol-1-yl)-6-(4-methoxy-1-((2-(trimethylsilyl)ethoxy)methyl)-1H-pyrazol-5-yl)pyrimidin-4-yl)pyrrolidin-3-yl)(methyl)carbamate (197 mg, 63%) as an oil.

LCMS (System 5, Method H): m/z 598 (M+H)$^+$ (ESI +ve), at 2.21 min, 205 nm.

A mixture of trifluoroacetic acid (2.7 mL) and water (0.3 mL) was prepared and added to tert-butyl (R)-(1-(2-(2,5-dimethyl-1H-pyrrol-1-yl)-6-(4-methoxy-1-((2-(trimethylsilyl)ethoxy)methyl)-1H-pyrazol-5-yl)pyrimidin-4-yl)pyrrolidin-3-yl)(methyl)carbamate (197 mg, 0.33 mmol) to give a solution, which was stirred at RT under an atmosphere of nitrogen for 24 h. The dark red/black solution was diluted with an equal volume of toluene and concentrated in-vacuo. The residue was co-evaporated from toluene to give a dark oil which slowly solidified on standing to give a red/black solid. The solid was purified by purification Method J to give (R)-4-(4-methoxy-1H-pyrazol-5-yl)-6-(3-(methylamino) pyrrolidin-1-yl)pyrimidin-2-amine Example 4-4 (17 mg, 17%) as a solid.

The data for Example 4-4 are in Table 3.

Route L

Typical Procedure for the Preparation of Pyrimidines as Exemplified by the Preparation of Example 7-1, (R)-4-(3,4-dimethyl-1H-pyrazol-5-yl)-6-(3-(methylamino)pyrrolidin-1-yl)pyrimidin-2-amine dihydrochloride

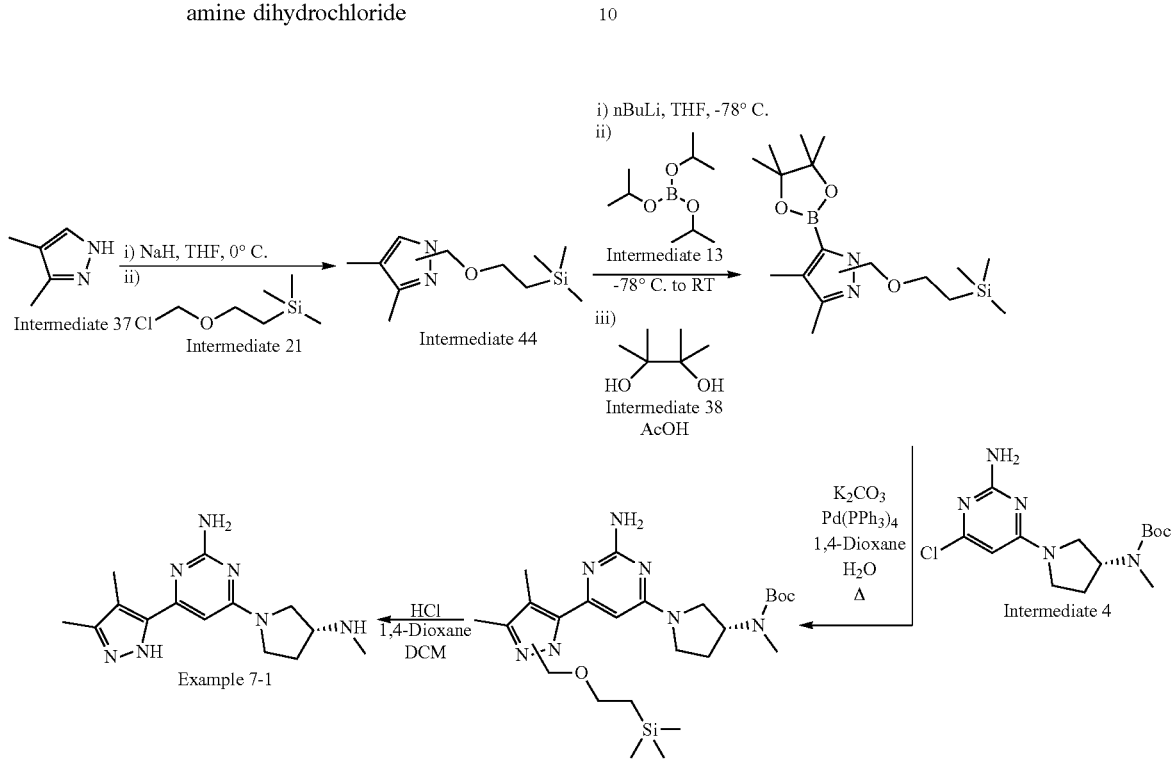

3,4-Dimethyl-1H-pyrazole (496 mg, 5.0 mmol) was dissolved in THF (20 mL), sodium hydride suspension in mineral oil (60%, 400 mg, 10 mmol) was added and the reaction was stirred at 0° C. for 1 h. (2-(Chloromethoxy) ethyl)trimethylsilane (Intermediate 21) (1.15 mL, 6.5 mmol) was added and the reaction mixture was stirred at RT overnight. The reaction mixture was partitioned between water (25 mL) and EtOAc (40 mL) and the aqueous phase was extracted further with EtOAc (3×50 mL). The combined organic phases were concentrated and the residue was purified by flash column chromatography (normal phase SiO$_2$, 0% to 100% EtOAc in isohexane) to give a ~1:1 mixture of 3,4-dimethyl-1-((2-(trimethylsilyl)ethoxy)methyl)-1H-pyrazole and 4,5-dimethyl-1-((2-(trimethylsilyl)ethoxy) methyl)-1H-pyrazole (Intermediate 44) (1100 mg, 97%) as an oil.

The data for Intermediate 44 are in Table 2.

A solution of a ~1:1 mixture of 3,4-dimethyl-1-((2-(trimethylsilyl)ethoxy)methyl)-1H-pyrazole and 4,5-dimethyl-1-((2-(trimethylsilyl)ethoxy)methyl)-1H-pyrazole (Intermediate 44) (453 mg, 2.0 mmol) dissolved in THF (10 mL) was cooled to −78° C. To this solution was added n-butyllithium solution in hexanes (2.5 M, 2.0 mL, 5.0 mmol) and the reaction mixture was stirred at −78° C. for 1 h. To the reaction mixture was then added triisopropyl borate (Intermediate 13) (1.21 mL, 6.0 mmol) as a solution in THF (1 mL) at −78° C., and the resulting mixture was stirred for 1 h then allowed to warm to RT overnight. 2,3-Dimethylbutane-2,3-diol (Intermediate 38) (355 mg, 3.0 mmol) was added followed by acetic acid (0.34 mL, 6.0 mmol) added 10 minutes later and the resulting mixture was stirred for an additional 10 min. The reaction mixture was filtered through Celite and the filtrate was concentrated to give a regio-isomeric mixture of 3,4-dimethyl-5-(4,4,5,5-tetramethyl-1, 3,2-dioxaborolan-2-yl)-1-((2-(trimethylsilyl)ethoxy) methyl)-1H-pyrazole and 4,5-dimethyl-3-(4,4,5,5-tetramethyl-1,3,2-dioxaborolan-2-yl)-1-((2-(trimethylsilyl) ethoxy)methyl)-1H-pyrazole as an oil, which was used directly in the next reaction.

LCMS (System 4, Method F): m/z 252 (boronic acid-18)$^+$ (ES$^+$), at 2.72 min, 254 nm.

A mixture of potassium carbonate (276 mg, 2.0 mmol), tetrakis(triphenylphosphine)palladium (0) (CAS: 95464-05-4) (116 mg, 0.10 mmol), a regio-isomeric mixture of 3,4-dimethyl-5-(4,4,5,5-tetramethyl-1,3,2-dioxaborolan-2-yl)-1-((2-(trimethylsilyl)ethoxy)methyl)-1H-pyrazole and 4,5-dimethyl-3-(4,4,5,5-tetramethyl-1,3,2-dioxaborolan-2-yl)-1-((2-(trimethylsilyl)ethoxy)methyl)-1H-pyrazole (352 mg, 1.0 mmol) and tert-butyl (R)-(1-(2-amino-6-chloropyrimidin-4-yl)pyrrolidin-3-yl)(methyl)carbamate (Intermediate 4) (328 mg, 1.0 mmol) in 1,4-dioxane (2.2 mL) and water (0.10 mL) was heated to 110° C. and maintained at that temperature overnight. The reaction mixture was then partitioned between DCM (5 mL) and water (5 mL), and the aqueous phase was further extracted with DCM (3×5 mL). The combined organic phases were concentrated and the residue was purified by purification Method K to give either tert-butyl (R)-(1-(2-amino-6-(4,5-dimethyl-1-((2-(trimethylsilyl)ethoxy)methyl)-1H-pyrazol-3-yl)pyrimidin-4-yl)pyrrolidin-3-yl)(methyl)carbamate or tert-butyl (R)-(1-(2-amino-6-(3,4-dimethyl-1-((2-(trimethylsilyl)ethoxy)methyl)-1H-pyrazol-5-yl)pyrimidin-4-yl)pyrrolidin-3-yl)(methyl) carbamate or a mixture of both isomers (6 mg, 1%).

LCMS (System 4, Method F): m/z 518 (M+H)+ (ES+), at 2.55 min, 254 nm.

tert-Butyl (R)-(1-(2-amino-6-(4,5-dimethyl-1-((2-(trimethylsilyl)ethoxy)methyl)-1H-pyrazol-3-yl)pyrimidin-4-yl)pyrrolidin-3-yl)(methyl)carbamate or tert-butyl (R)-(1-(2-amino-6-(3,4-dimethyl-1-((2-(trimethylsilyl)ethoxy)methyl)-1H-pyrazol-5-yl)pyrimidin-4-yl)pyrrolidin-3-yl)(methyl)carbamate or a mixture of both isomers (6 mg, 0.01 mmol) was dissolved in DCM (2 mL) and HCl solution in 1,4-dioxane (4 M, 0.01 mL, 0.0400 mmol) was added. The mixture was stirred at RT overnight and the resulting precipitate was removed by filtration to give (R)-4-(3,4-dimethyl-1H-pyrazol-5-yl)-6-(3-(methylamino)pyrrolidin-1-yl)pyrimidin-2-amine dihydrochloride, Example 7-1 (3 mg, 72%).

The data for Example 7-1 are in Table 3.

Route M

Typical Procedure for the Preparation of Pyrimidines as Exemplified by the Preparation of Example 11-1, ((R)-4-(1,3-dimethyl-1H-pyrazol-4-yl)-6-(3-(methylamino)pyrrolidin-1-yl)pyrimidin-2-amine

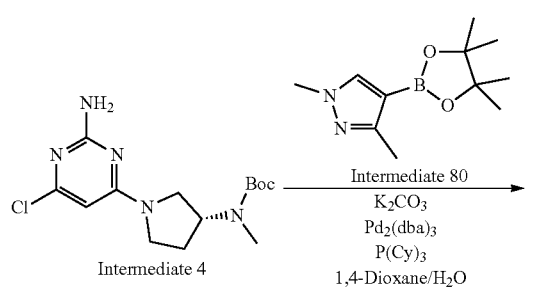

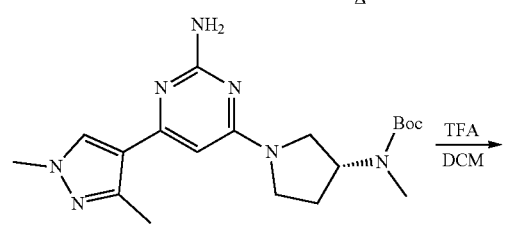

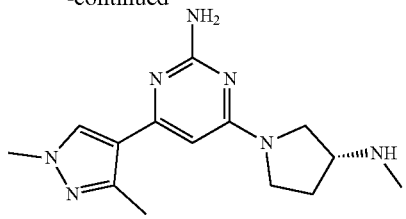

Example 11-1 tert-Butyl (R)-(1-(2-amino-6-chloropyrimidin-4-yl)pyrrolidin-3-yl)(methyl)carbamate (Intermediate 4) (1.0 g, 3.00 mmol), 1,3-dimethyl-4-(4,4,5,5-tetramethyl-1,3,2-dioxaborolan-2-yl)-1H-pyrazole (Intermediate 80) (0.87 g, 3.90 mmol), K$_2$CO$_3$ (1.65 g, 12.0 mmol) and water (4.0 mL) were dissolved in 1,4-dioxane (16.0 mL) under nitrogen and degassed for 20 min. Tricyclohexylphosphine (0.12 g, 0.4 mmol) and tris(dibenzylideneacetone)dipalladium(0) (CAS: 51364-51-3) (274 mg, 0.32 mmol) were added under a nitrogen atmosphere and the mixture was stirred at 90° C. for 12 h. The reaction mixture was partitioned between H$_2$O (40 mL) and EtOAc (25 mL), and the aqueous layer was further extracted with EtOAc (3×25 mL). The combined organic layers were dried (Na$_2$SO$_4$) and the solvent was removed in-vacuo. The residue was purified by column chromatography (Normal-Phase activated Al$_2$O$_3$, 0% to 10% MeOH in DCM) to give tert-butyl (R)-(1-(2-amino-6-(1,3-dimethyl-1H-pyrazol-4-yl)pyrimidin-4-yl)pyrrolidin-3-yl)(methyl)carbamate (1.0 g, 86%) as a solid.

LCMS (System 3, Method D): m/z 388 (M+H)+ (ESI +ve), at 3.53 min, 202 nm.

tert-Butyl (R)-(1-(2-amino-6-(1,3-dimethyl-1H-pyrazol-4-yl)pyrimidin-4-yl)pyrrolidin-3-yl)(methyl)carbamate (1.0 g, 2.58 mmol) was dissolved in DCM (20 mL), TFA (5 mL) was added at 0° C. and the mixture was stirred for 1 h at room temperature. The mixture was concentrated and the residue was triturated with pentane (2×10 mL). The residue was purified by purification Method L to afford ((R)-4-(1,3-dimethyl-1H-pyrazol-4-yl)-6-(3-(methylamino)pyrrolidin-1-yl)pyrimidin-2-amine, Example 11-1 (500 mg, 68%) as a solid.

The data for Example 11-1 are in Table 3.

Route N

Typical Procedure for the Preparation of Pyrimidines as Exemplified by the Preparation of Example 11-7, 4-(1,3-dimethyl-1H-pyrazol-4-yl)-6-(3-methyl-3-(methylamino)pyrrolidin-1-yl)pyrimidin-2-amine

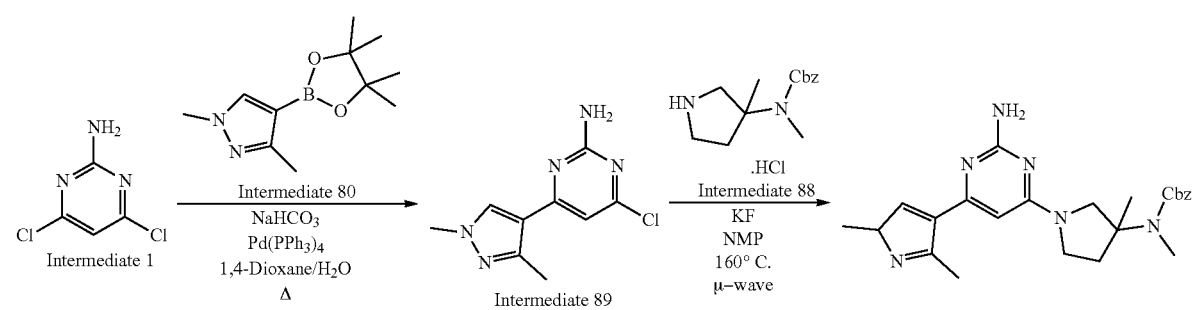

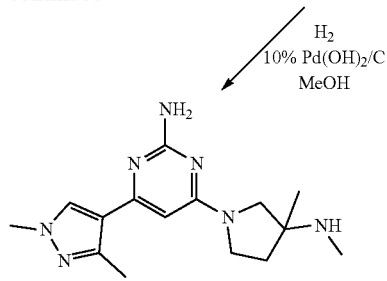

Example 11-7

4,6-Dichloropyrimidin-2-amine (Intermediate 1) (500 mg, 3.06 mmol), 1,3-dimethyl-4-(4,4,5,5-tetramethyl-1,3,2-dioxaborolan-2-yl)-1H-pyrazole (Intermediate 80) (0.68 g, 3.07 mmol) and NaHCO$_3$ (0.967 g, 9.20 mmol) were dissolved in a mixture of 1,4-dioxane (10 mL) and water (2 mL) under nitrogen and the resulting mixture was degassed for 20 min. Tetrakis(triphenylphosphine)palladium (0) (CAS: 95464-05-4) (0.355 g, 0.306 mmol) was added under a nitrogen atmosphere and the resulting mixture was stirred at 50-70° C. for 12 h. The reaction mixture was then partitioned between H$_2$O (40 mL) and EtOAc (40 mL), and the aqueous layer was further extracted with EtOAc (3×20 mL). The combined organic layers were dried (Na$_2$SO$_4$) and the solvent was removed in-vacuo. The residue was purified by column chromatography (Normal-Phase activated Al$_2$O$_3$, 20% ethyl acetate in hexane) to give 4-chloro-6-(1,3-dimethyl-1H-pyrazol-4-yl)pyrimidin-2-amine (Intermediate 89) (250 mg, 22%) as a solid.

The data for Intermediate 89 are in Table 2.

Benzyl methyl(3-methylpyrrolidin-3-yl)carbamate hydrochloride (Intermediate 88) (222 mg, 0.78 mmol) and 4-chloro-6-(1,3-dimethyl-1H-pyrazol-4-yl)pyrimidin-2-amine (Intermediate 89) were dissolved in N-methyl-2-pyrrolidinone (8 mL) under an atmosphere of nitrogen and potassium fluoride (156 mg, 2.68 mmol) was added. The resulting reaction mixture was stirred at 160° C. for 4 h using a CEM microwave. The mixture was then partitioned between H$_2$O (35 mL) and EtOAc (25 mL), and the aqueous layer was further extracted with EtOAc (2×25 mL). The combined organic layers were dried (Na$_2$SO$_4$) and the solvent was removed in-vacuo. The residue was purified by column chromatography (Normal-Phase neutral activated Al$_2$O$_3$, 2% to 6% MeOH in EtOAc) to give benzyl (1-(2-amino-6-(1,3-dimethyl-1H-pyrazol-4-yl)pyrimidin-4-yl)-3-methylpyrrolidin-3-yl)(methyl)carbamate (190 mg, 49%) as a solid.

LCMS (System 3, Method E): m/z 436 (M+H)$^+$ (ESI +ve), at 3.83 min, 247 nm.

Benzyl (1-(2-amino-6-(1,3-dimethyl-1H-pyrazol-4-yl)pyrimidin-4-yl)-3-methylpyrrolidin-3-yl)(methyl)carbamate (190 mg, 0.44 mmol) was dissolved in MeOH (15 mL) and 10% palladium hydroxide on carbon (50% moisture, 100 mg) was added. The vessel was then purged with hydrogen and stirred under an atmosphere of hydrogen at 25° C. for 6 h. The reaction mixture was filtered through Celite, washing the catalyst with MeOH, and the filtrate was concentrated in-vacuo to give the crude product, which was triturated with pentane (2×2 mL) to remove non-polar impurities. The product was purified by purification Method M followed by purification Method N to give 4-(1,3-dimethyl-1H-pyrazol-4-yl)-6-(3-methyl-3-(methylamino)pyrrolidin-1-yl)pyrimi-din-2-amine, Example 11-7 Isomer 1 (19 mg, 15%) as a solid and 4-(1,3-dimethyl-1H-pyrazol-4-yl)-6-(3-methyl-3-(methylamino)pyrrolidin-1-yl)pyrimidin-2-amine, Example 11-7 Isomer 2 (20 mg, 15%) as a solid.

The data for Example 11-7 Isomer 2 are in Table 3.

Route O

Typical Procedure for the Preparation of Pyrimidines as Exemplified by the Preparation of Example 11-8, 4-(1,3-dimethyl-11H-pyrazol-4-yl)-6-(octahydro-6H-pyrrolo[3,4-b]pyridin-6-yl)pyrimidin-2-amine

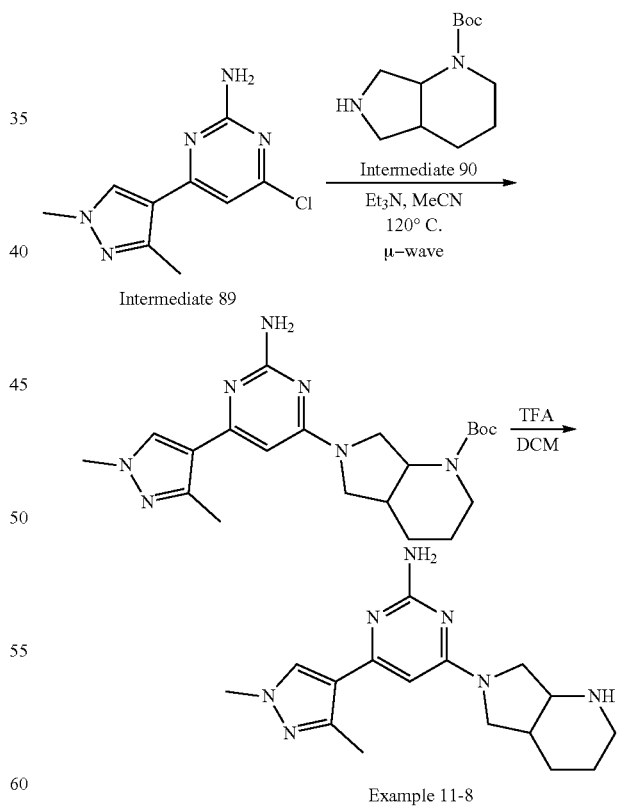

Example 11-8

4-Chloro-6-(1,3-dimethyl-1H-pyrazol-4-yl)pyrimidin-2-amine (Intermediate 89) (150 mg, 0.672 mmol) was dissolved in MeCN:TEA (1:1, 10 mL) and tert-butyl octahydro-1H-pyrrolo[3,4-b]pyridine-1-carboxylate (Intermediate 90) (228 mg, 1.01 mmol) was added at RT. The mixture was stirred at 120° C. for 6 h using a CEM microwave. The reaction mixture was concentrated in-vacuo, and the residue was purified by column chromatography (Neutral Al₂O₃, 0% to 10% MeOH:DCM) to give tert-butyl 6-(2-amino-6-(1,3-dimethyl-1H-pyrazol-4-yl)pyrimidin-4-yl)octahydro-1H-pyrrolo[3,4-b]pyridine-1-carboxylate as a solid (150 mg, 54%).

LCMS (System 3, Method D): m/z 414 (M+H)⁺ (ESI +ve), at 3.75 min, 254 nm.

tert-Butyl 6-(2-amino-6-(1,3-dimethyl-1H-pyrazol-4-yl)pyrimidin-4-yl)octahydro-1H-pyrrolo[3,4-b]pyridine-1-carboxylate (150 mg, 3.63 mmol) was dissolved DCM (10 mL) and TFA (2 mL) was added at 0° C. The resulting mixture was stirred for 1 h at room temperature, then concentrated in-vacuo and the residue was triturated with pentane (2×10 mL) to give crude product. The crude product was purified by purification Method O followed by purification Method P to give 4-(1,3-dimethyl-1H-pyrazol-4-yl)-6-(octahydro-6H-pyrrolo[3,4-b]pyridin-6-yl)pyrimidin-2-amine, Example 11-8 Isomer 1 (20 mg, 18%) and 4-(1,3-dimethyl-1H-pyrazol-4-yl)-6-(octahydro-6H-pyrrolo[3,4-b]pyridin-6-yl)pyrimidin-2-amine, Example 11-8 Isomer 2 (10 mg, 9%).

The data for Example 11-7 Isomer 1 and Isomer 2 are in Table 3.

Route P

Typical Procedure for the Preparation of Pyridines as Exemplified by the Preparation of Example 14-1, (R)-6-(1,5-dimethyl-1H-pyrazol-4-yl)-4-(3-(methylamino)pyrrolidin-1-yl)pyridin-2-amine dihydrochloride

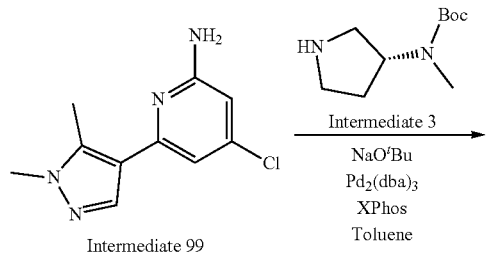

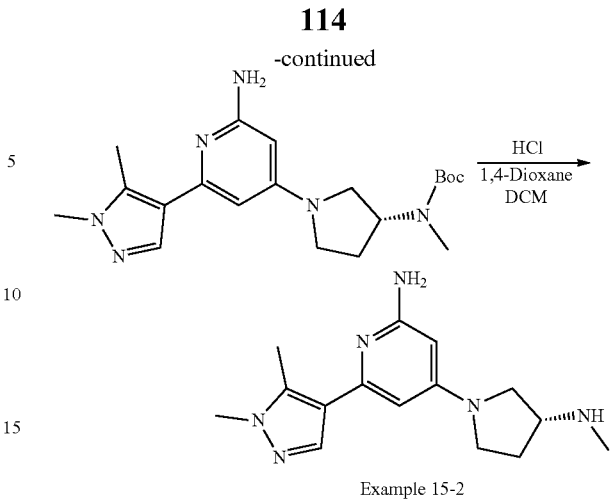

Example 15-2

To a nitrogen purged microwave vial containing XPhos (CAS: 564483-18-7) (93 mg, 0.19 mmol), 4-chloro-6-(1,5-dimethyl-1H-pyrazol-4-yl)pyridin-2-amine (Intermediate 99) (210 mg, 0.94 mmol), tris(dibenzylideneacetone)dipalladium(0) (CAS: 51364-51-3) (86 mg, 0.09 mmol) and (R)-methyl(pyrrolidin-3-yl)carbamate (Intermediate 3) (208 mg, 1.04 mmol) was added toluene (5 mL). The reaction vessel was purged with nitrogen and sodium tert-butoxide (272 mg, 2.83 mmol) was added. The vessel was then sealed and heated conventionally at 110° C. for 16 h. The reaction mixture was partitioned between EtOAc (5 mL) and water (5 mL) and the aqueous phase was further extracted with EtOAc (3×5 mL). The combined organic phases were concentrated and the residue was purified by flash column chromatography (normal phase SiO₂, 0% to 10% MeOH in DCM) to give the crude product which was further purified by purification Method Q to give tert-butyl (R-(1-(2-amino-6-(15-dimethyl-1H-pyrazol-4-yl)pyridin-4-yl)pyrrolidin-3-yl)(methyl)carbamate (5 mg, 1%) as an oil.

LCMS (System 4, Method F): m/z 387 (M+H)⁺ (ES⁺), at 2.07 min, 254 nm.

tert-Butyl (R)-(1-(2-amino-6-(1,5-dimethyl-1H-pyrazol-4-yl)pyridin-4-yl)pyrrolidin-3-yl)(methyl)-carbamate (5 mg, 0.010 mmol) was dissolved in DCM (2 mL), HCl solution in 1,4-dioxane (4 M, 0.01 mL, 0.06 mmol) was added and the resulting mixture was stirred at RT overnight. After this time the white precipitate was filtered off to give (R)-6-(1,5-dimethyl-1H-pyrazol-4-yl)-4-(3-(methylamino) pyrrolidin-1-yl)pyridin-2-amine dihydrochloride, Example 14-1 (3 mg, 78%).

TABLE 2

Intermediates
Table 2

| Intermediate Number | Name | Synthetic Route | Intermediates Used | Data |
|---|---|---|---|---|
| 1 | 4,6-Dichloropyrimidin-2-amine | — | — | Commercially available, CAS: 56-05-3 |
| 2 | 5-(4,4,5,5-Tetramethyl-1,3,2-dioxaborolan-2-yl)-1H-pyrazole | — | — | Commercially available, CAS: 844501-71-9 |
| 3 | tert-Butyl (R)-methyl(pyrrolidin-3-yl)carbamate | — | — | Commercially available, CAS: 392338-15-7 |
| 4 | tert-Butyl (R)-(1-(2-amino-6-chloropyrimidin-4-yl)pyrrolidin-3-yl)(methyl)carbamate | B (Step 1) | 1 and 3 | LCMS (System 2, Method E): m/z 328 (M + H)⁺ (ES⁺), at 3.77 min, 240 nm |
| 5 | 1-Methyl-5-(4,4,5,5-tetramethyl-1,3,2-dioxaborolan-2-yl)-1H-pyrazole | — | — | Commercially available, CAS: 847818-74-0 |

TABLE 2-continued

Intermediates Table 2

| Intermediate Number | Name | Synthetic Route | Intermediates Used | Data |
|---|---|---|---|---|
| 6 | 1-Methyl-3-(4,4,5,5-tetramethyl-1,3,2-dioxaborolan-2-yl)-1H-pyrazole | — | — | Commercially available, CAS: 1020174-04-2 |
| 7 | 3-Bromo-1-(difluoromethyl)-1H-pyrazole | — | — | Commercially available, CAS: 1224194-42-6 |
| 8 | Bis(pinacolato)diboron | — | — | Commercially available, CAS: 73183-34-3 |
| 9 | 3-Methyl-1-(tetrahydro-2H-pyran-2-yl)-5-(4,4,5,5-tetramethyl-1,3,2-dioxaborolan-2-yl)-1H-pyrazole | — | — | Commercially available, CAS: 1486485-62-4 |
| 10 | 3-Cyclopropyl-1-(tetrahydro-2H-pyran-2-yl)-5-(4,4,5,5-tetramethyl-1,3,2-dioxaborolan-2-yl)-1H-pyrazole | — | — | Commercially available, CAS: 1486485-57-7 |
| 11 | 5-Bromo-1-((2-(trimethylsilyl)ethoxy)methyl)-1H-pyrazole-3-carbaldehyde | — | — | Commercially available, Alichem (China) Co. Ltd. Product code: 049000432 |
| 12 | 5-Bromo-3-(difluoromethyl)-1-((2-(trimethylsilyl)ethoxy)methyl)-1H-pyrazole | 1 | 11 | $^1$H NMR (400 MHZ, Chloroform-d) δ 6.62 (t, J = 54.9 Hz, 1H), 6.59 (s, 1H), 5.49 (s, 1H), 3.65-3.56 (m, 2H), 0.95-0.86 (m, 2H), 0.01-0.05 (m, 9H). |
| 13 | Triisopropyl borate | — | — | Commercially available, CAS: 5419-55-6 |
| 14 | Ethyl 3-(trifluoromethyl)-1H-pyrazole-5-carboxylate | — | — | Commercially available, CAS: 129768-30-5 |
| 15 | 3-(Trifluoromethyl)-1H-pyrazole-5-carboxylic acid | 2 | 14 | LCMS (System 2, Method E): m/z 179 (M − H)$^-$ (ES$^-$, at 2.47 min, 230 nm |
| 16 | Potassium 3-ethoxy-3-oxopropanoate | — | — | Commercially available, CAS: 6148-64-7 |
| 17 | Guanidine hydrochloride | — | — | Commercially available, CAS: 50-01-1 |
| 18 | tert-Butyl (R)-pyrrolidin-3-ylcarbamate | — | — | Commercially available, CAS: 122536-77-0 |
| 19 | 4-Methyl-1-(tetrahydro-2H-pyran-2-yl)-5-(4,4,5,5-tetramethyl-1,3,2-dioxaborolan-2-yl)-1H-pyrazole | — | — | Commercially available CAS: 1492954-33-2 |
| 20 | 4-Ethyl-1H-pyrazole | — | — | Commercially available, CAS: 17072-38-7 |
| 21 | (2-(Chloromethoxy)ethyl)trimethylsilane | — | — | Commercially available, CAS: 76513-69-4 |
| 22 | 4-Ethyl-1-((2-(trimethylsilyl)ethoxy)methyl)-1H-pyrazole | 3 | 20 and 21 | $^1$H NMR (400 MHZ, Chloroform-d) δ 7.36 (s, 1H), 7.33-7.31 (m, 1H), 5.34 (s, 2H), 3.57-3.48 (m, 2H), 2.54-2.44 (m, 2H), 1.22-1.14 (m, 3H), 0.92-0.83 (m, 2H), −0.01-0.09 (m, 9H). |
| 23 | 4-Chloro-1H-pyrazole | — | — | Commercially available, CAS: 15878-00-9 |
| 24 | 4-Chloro-1-((2-(trimethylsilyl)ethoxy)methyl)-1H-pyrazole | 3 | 23 and 21 | $^1$H NMR (400 MHZ, Chloroform-d) δ 7.58-7.50 (m, 1H), 7.47-7.41 (m, 1H), 5.36 (s, 2H), 3.59-3.47 (m, 2H), 0.95-0.83 (m, 2H), −0.03 (s, 9H). |
| 25 | Hexane-2,5-dione | — | — | Commercially available, CAS: 110-13-4 |
| 26 | tert-Butyl (R)-(1-(6-chloro-2-(2,5-dimethyl-1H-pyrrol-1-yl)pyrimidin-4-yl)pyrrolidin-3-yl)(methyl)carbamate | 4 | 1, 25 and 3 | LCMS (System 4, Method F): m/z 406/408 (M + H)$^+$ (ES$^+$), at 2.72 min, 254 nm |
| 27 | 4-Methoxy-1H-pyrazole | — | — | Commercially available, CAS: 14884-01-6 |
| 28 | 4-Methoxy-1-((2-(trimethylsilyl)ethoxy)methyl)-1H-pyrazole | 3 | 27 and 21 | LCMS (System 5, Method H): m/z 229 (M + H)$^+$ (ES$^+$), at 1.47 min, 205 nm |
| 29 | 4-Methyl-1H-pyrazole-5-carboxylic acid | — | — | Commercially available, CAS: 82231-51-4 |
| 30 | Ethyl 5-methyl-1H-pyrazole-3-carboxylate | — | — | Commercially available, CAS: 4027-57-0 |
| 31 | 1,5-Dimethyl-1H-pyrazole-3-carboxylic acid | 5 | 29 | LCMS (System 1, Method B): m/z 141 (M + H)$^+$ (ESI + ve), at 1.23 min, 235 nm |

TABLE 2-continued

Intermediates Table 2

| Intermediate Number | Name | Synthetic Route | Intermediates Used | Data |
|---|---|---|---|---|
| 32 | 1-(Difluoromethyl)-5-methyl-1H-pyrazole-3-carboxylic acid | — | — | Commercially available, CAS: 1004643-64-4 |
| 33 | Ethyl 4-methyl-1H-pyrazole-3-carboxylate | — | — | Commercially available, CAS: 6076-12-6 |
| 34 | 1,4-Dimethyl-1H-pyrazole-3-carboxylic acid | 5 | 33 | LCMS (System 2, Method E): m/z 141 (M + H)$^+$ (ESI + ve), at 1.49 min, 237 nm |
| 35 | Sodium 2-chloro-2,2-difluoroacetate | — | — | Commercially available, CAS: 1895-39-2 |
| 36 | 1-(Difluoromethyl)-4-methyl-1H-pyrazole-3-carboxylic acid | 6 | 33 and 35 | LCMS (System 3, Method D): m/z 177 (M + H)$^+$ (ESI + ve), at 1.12 min, 202 nm |
| 37 | 3,4-Dimethyl-1H-pyrazole | — | — | Commercially available, CAS: 2820-37-3 |
| 38 | 2,3-Dimethylbutane-2,3-diol | — | — | Commercially available, CAS: 76-09-5 |
| 39 | 4-Chloro-3-methyl-1H-pyrazole | — | — | Commercially available, CAS: 15878-08-7 |
| 40 | 3-Ethyl-4-methyl-1H-pyrazole | — | — | Commercially available, CAS: 7231-33-6 |
| 41 | 3-Iodo-1,4,5,6-tetrahydrocyclopenta[c]pyrazole | — | — | Commercially available, CAS: 1426424-00-1 |
| 42 | Trimethyl borate | — | — | Commercially available, CAS: 121-43-7 |
| 43 | 3-(4,4,5,5-Tetramethyl-1,3-dioxolan-2-yl)-1H-indazole | — | — | Commercially available, CAS: 937366-55-7 |
| 44 | Mixture of 3,4-dimethyl-1-((2-(trimethylsilyl)ethoxy)methyl)-1H-pyrazole and 4,5-dimethyl-1-((2-(trimethylsilyl)ethoxy)methyl)-1H-pyrazole | L (Step 1) | 37 and 21 | $^1$H NMR (400 MHz, Chloroform-d) δ 7.26, 7.24 (2 × s, 1H), 5.37, 5.29 (2 × s, 2H), 3.56-3.50 (m, 2H), 2.24, 2.20 (2 × s, 3H), 2.01-1.98 (m, 3H), 0.93-0.84 (m, 2H), −0.02, −0.03 (2 × s, 9H). |
| 45 | tert-Butyl (R)-(1-(2-amino-6-chloropyrimidin-4-yl)pyrrolidin-3-yl) carbamate | B (Step 1) | 1 and 18 | LCMS (System 4, Method F): m/z 314/316 (M+H)+ (ES+), at 1.86 min, 254 nm |
| 46 | Mixture of 4-chloro-3-methyl-1-((2-(trimethylsilyl)ethoxy)methyl)-1H-pyrazole and 4-chloro-5-methyl-1-((2-(trimethylsilyl)ethoxy)methyl)-1H-pyrazole | 3 | 39 and 21 | LCMS (System 4, Method F): m/z 189/191 (M − SiMe2 + H)$^+$ (ES$^+$), at 3.08 min, 254 nm |
| 47 | 4-(4,4,5,5-Tetramethyl-1,3,2-dioxaborolan-2-yl)-1H-pyrazole | — | — | Commercially available, CAS: 269410-08-4 |
| 48 | 1-Methyl-4-(4,4,5,5-tetramethyl-1,3,2-dioxaborolan-2-yl)-1H-pyrazole | — | — | Commercially available, CAS: 761446-44-0 |
| 49 | 1-Ethyl-4-(4,4,5,5-tetramethyl-1,3,2-dioxaborolan-2-yl)-1H-pyrazole | — | — | Commercially available, CAS: 847818-70-6 |
| 50 | 1-Cyclopropyl-4-(4,4,5,5-tetramethyl-1,3,2-dioxaborolan-2-yl)-1H-pyrazole | — | — | Commercially available, CAS: 1151802-22-0 |
| 51 | 1-Cyclobutyl-4-(4,4,5,5-tetramethyl-1,3,2-dioxaborolan-2-yl)-1H-pyrazole | — | — | Commercially available, CAS: 1002309-48-9 |
| 52 | 1-(Difluoromethyl)-4-(4,4,5,5-tetramethyl-1,3,2-dioxaborolan-2-yl)-1H-pyrazole | — | — | Commercially available, CAS: 1206640-82-5 |
| 53 | 4-(4,4,5,5-Tetramethyl-1,3,2-dioxaborolan-2-yl)-1-(trifluoromethyl)-1H-pyrazole | — | — | Commercially available, CAS: 1046831-98-4 |
| 54 | 4-(4,4,5,5-Tetramethyl-1,3,2-dioxaborolan-2-yl)-1-(2,2,2-trifluoroethyl)-1H-pyrazole | — | — | Commercially available, CAS: 1049730-42-8 |
| 55 | 2-(4-(4,4,5,5-Tetramethyl-1,3,2-dioxaborolan-2-yl)-1H-pyrazol-1-yl)ethan-1-ol | — | — | Commercially available, CAS: 1040377-08-9 |
| 56 | 1-(2-Methoxyethyl)-4-(4,4,5,5-tetramethyl-1,3,2-dioxaborolan-2-yl)-1H-pyrazole | — | — | Commercially available, CAS: 847818-71-7 |
| 57 | 1-(Oxetan-3-yl)-4-(4,4,5,5-tetramethyl-1,3,2-dioxaborolan-2-yl)-1H-pyrazole | — | — | Commercially available, CAS: 1339890-99-1 |

TABLE 2-continued

Intermediates Table 2

| Intermediate Number | Name | Synthetic Route | Intermediates Used | Data |
|---|---|---|---|---|
| 58 | 3-(4-(4,4,5,5-Tetramethyl-1,3,2-dioxaborolan-2-yl)-1H-pyrazol-1-yl)propanenitrile | — | — | Commercially available, CAS: 1022092-33-6 |
| 59 | 2-(4-(4,4,5,5-Tetramethyl-1,3,2-dioxaborolan-2-yl)-1H-pyrazol-1-yl)acetonitrile | — | — | Commercially available, CAS: 1093307-35-7 |
| 60 | tert-Butyl 3-oxopiperidine-1-carboxylate | — | — | Commercially available, CAS: 98977-36-7 |
| 61 | 4-Bromo-1H-pyrazole | — | — | Commercially available, CAS: 2075-45-8 |
| 62 | Ethyl chloroformate | — | — | Commercially available, CAS: 541-41-3 |
| 63 | Ethyl 3-(4-(4,4,5,5-tetramethyl-1,3,2-dioxaborolan-2-yl)-1H-pyrazol-1-yl)piperidine-1-carboxylate | 7 | 60, 61, 62 and 8 | LCMS (System 2, Method E): m/z 350 (M + H)$^+$ (ESI + ve), at 4.14 min, 202 nm |
| 64 | tert-Butyl azetidin-3-yl(methyl) carbamate hydrochloride | — | — | Commercially available, CAS: 943060-59-1 |
| 65 | tert-Butyl (1-(2-amino-6-chloropyrimidin-4-yl)azetidin-3-yl)(methyl)carbamate | B (Step 1) (DIPEA used instead of TEA) | 1 and 64 | LCMS (System 4, Method F): m/z 258/260 (M-56 + H)$^+$ (ES$^+$), at 1.97 min, 254 nm |
| 68 | 3-Methyl-4-(4,4,5,5-tetramethyl-1,3,2-dioxaborolan-2-yl)-1H-pyrazole | — | — | Commercially available, CAS: 936250-20-3 |
| 69 | 4-Bromo-3-ethyl-1H-pyrazole | — | — | Commercially available, CAS: 15802-79-6 |
| 70 | 3,4-Dihydro-2H-pyran | — | — | Commercially available, CAS: 110-87-2 |
| 71 | 4-Bromo-3-ethyl-1-(tetrahydro-2H-pyran-2-yl)-1H-pyrazole | 8 | 69 and 70 | $^1$H NMR (400 MHZ, Chloroform-d) δ 1.22-1.29 (m, 3H), 1.50-1.75 (m, 4H), 1.97-2.06 (m, 2H), 2.58-2.79 (m, 2H), 3.99-4.16 (m, 2H), 5.23-5.32 (m, 1H), 7.55 (s, 1H). |
| 72 | 3-Ethyl-1-(tetrahydro-2H-pyran-2-yl)-4-(4,4,5,5-tetramethyl-1,3,2-dioxaborolan-2-yl)-1H-pyrazole | D (Step 1) | 71 and 8 | LCMS (System 2, Method E): m/z 307 (M + H)$^+$ (ESI + ve), at 4.47 min, 202 nm |
| 73 | 3-Isopropyl-4-(4,4,5,5-tetramethyl-1,3,2-dioxaborolan-2-yl)-1H-pyrazole | — | — | Commercially available, CAS: 1983152-92-6 |
| 74 | 3-Cyclopropyl-4-(4,4,5,5-tetramethyl-1,3,2-dioxaborolan-2-yl)-1H-pyrazole | — | — | Commercially available, CAS: 957345-32-3 |
| 75 | 4-Bromo-3-(difluoromethyl)-1H-pyrazole | — | — | Commercially available, CAS: 1451392-65-6 |
| 76 | 4-Bromo-3-(difluoromethyl)-1-(tetrahydro-2H-pyran-2-yl)-1H-pyrazole | 8 | 75 and 70 | LCMS (System 1, Method B): m/z 281/283 (M + H)$^+$ (ESI + ve), at 1.70 min, 270 nm |
| 77 | 3-(Difluoromethyl)-1-(tetrahydro-2H-pyran-2-yl)-4-(4,4,5,5-tetramethyl-1,3,2-dioxaborolan-2-yl)-1H-pyrazole | D (Step 1) | 76 and 8 | LCMS (System 1, Method B): m/z 329 (M + H)$^+$ (ESI + ve), at 1.88 min, 228 nm |
| 78 | 4-(4,4,5,5-Tetramethyl-1,3,2-dioxaborolan-2-yl)-3-(trifluoromethyl)-1H-pyrazole | — | — | Commercially available, CAS: 1218790-40-9 |
| 79 | 3,5-Dimethyl-1-(tetrahydro-2H-pyran-2-yl)-4-(4,4,5,5-tetramethyl-1,3,2-dioxaborolan-2-yl)-1H-pyrazole | — | — | Commercially available, CAS: 1126779-11-0 |
| 80 | 1,3-Dimethyl-4-(4,4,5,5-tetramethyl-1,3,2-dioxaborolan-2-yl)-1H-pyrazole | — | — | Commercially available, CAS: 1046832-21-6 |
| 81 | 3-Ethyl-1-methyl-4-(4,4,5,5-tetramethyl-1,3,2-dioxaborolan-2-yl)-1H-pyrazole | — | — | Commercially available, CAS: 1619991-78-4 |
| 82 | 3-Cyclopropyl-1-methyl-4-(4,4,5,5-tetramethyl-1,3,2-dioxaborolan-2-yl)-1H-pyrazole | — | — | Commercially available, CAS: 1257637-82-3 |
| 83 | 1-Methyl-4-(4,4,5,5-tetramethyl-1,3,2-dioxaborolan-2-yl)-3-(trifluoromethyl)-1H-pyrazole | — | — | Commercially available, CAS: 1218790-53-4 |

TABLE 2-continued

Intermediates
Table 2

| Intermediate Number | Name | Synthetic Route | Intermediates Used | Data |
|---|---|---|---|---|
| 84 | 4-Bromo-1-methyl-1H-pyrazole-3-carbonitrile | — | — | Commercially available, CAS: 287922-71-8 |
| 85 | 4-Bromo-1-(difluoromethyl)-3-methyl-1H-pyrazole | — | — | Commercially available, CAS: 1215295-92-3 |
| 86 | tert-Butyl 3-amino-3-methylpyrrolidine-1-carboxylate | — | — | Commercially available, CAS: 1158758-59-8 |
| 87 | Benzyl chloroformate | — | — | Commercially available, CAS: 501-53-1 |
| 88 | Benzyl methyl(3-methylpyrrolidin-3-yl) carbamate hydrochloride | 9 | 86 and 87 | LCMS (System 3, Method C): m/z 249 (M + H)+ (ESI + ve), at 7.99 min, 202 nm |
| 89 | 4-Chloro-6-(1,3-dimethyl-1H-pyrazol-4-yl)pyrimidin-2-amine | M (Step 1) | | LCMS (System 3, Method E): m/z 224/226 (M + H)+ (ESI + ve), at 2.79 min, 254 nm |
| 90 | tert-Butyl octahydro-1H-pyrrolo[3,4-b]pyridine-1-carboxylate | — | — | Commercially available, CAS: 159877-36-8 |
| 91 | 1,5-Dimethyl-4-(4,4,5,5-tetramethyl-1,3,2-dioxaborolan-2-yl)-1H-pyrazole | — | — | Commercially available, CAS: 1036991-40-8 |
| 92 | 4-Bromo-1-methyl-1H-pyrazole-5-carbonitrile | — | — | Commercially available, CAS: 327099-80-9 |
| 93 | 4-Bromo-1-(difluoromethyl)-5-methyl-1H-pyrazole | — | — | Commercially available, CAS: 1243250-04-5 |
| 94 | 3-(4,4,5,5-Tetramethyl-1,3,2-dioxaborolan-2-yl)-5,6-dihydro-4H-pyrrolo[1,2-b]pyrazole | — | — | Commercially available, CAS: 1314138-13-0 |
| 95 | 1,3,5-Trimethyl-4-(4,4,5,5-tetramethyl-1,3,2-dioxaborolan-2-yl)-1H-pyrazole | — | — | Commercially available, CAS: 844891-04-9 |
| 98 | 4,6-Dichloropyridin-2-amine | — | — | Commercially available, CAS: 116632-24-7 |
| 99 | 4-Chloro-6-(1,5-dimethyl-1H-pyrazol-4-yl)pyridin-2-amine | Q | 98 and 91 | LCMS (System 2, Method E): m/z 223/225 (M + H)+ (ESI + ve), at 3.00 min, 234 nm. |
| 100 | 3-(4,4,5,5-Tetramethyl-1,3,2-dioxaborolan-2-yl)cyclopent-2-en-1-one | — | — | Commercially available, CAS: 1370008-65-3 |
| 101 | 3-Ethyl-1H-pyrazole | — | — | Commercially available, CAS: 13808-71-4 |
| 102 | 3-Ethyl-1-((2-(trimethylsilyl)ethoxy)methyl)-1H-pyrazole | 3 | 101 and 21 | LCMS (System 4, Method F): m/z 169 (M − SiMe$_2$ + H)+ (ES+), at 2.39 min, 200-400 nm |
| 103 | tert-Butyl (S)-methyl(pyrrolidin-3-yl) carbamate | — | — | Commercially available, CAS: 169750-01-0 |
| 104 | N,3-Dimethylpyrrolidin-3-amine | — | — | Commercially available, CAS: 685879-85-0 |
| 105 | tert-Butyl azetidin-3-ylcarbamate | — | — | Commercially available, CAS: 91188-13-5 |
| 106 | N,3-dimethylazetidin-3-amine dihydrochloride | — | — | Commercially available, CAS: 2170250-39-0 |
| 107 | tert-Butyl hexahydropyrrolo[3,4-b]pyrrole-1(2H)-carboxylate | — | — | Commercially available, CAS: 185693-02-1 |
| 108 | tert-Butyl (4aR,7aR)-octahydro-1H-pyrrolo[3,4-b]pyridine-1-carboxylate | — | — | Commercially available, CAS: 186201-89-8 |
| 109 | Ethyl 4-formyl-1H-pyrazole-3-carboxylate | — | — | Commercially available, CAS: 179692-09-2 |
| 110 | 1-(Chloromethyl)-4-methoxybenzene | — | — | Commercially available, CAS: 824-94-2 |
| 111 | 4-(Difluoromethyl)-1-(4-methoxybenzyl)-1H-pyrazole-3-carboxylic acid | 10 | 109 and 110 | LCMS (System 1, Method B): no mass ion, at 1.50 min, 235 nm. |
| 112 | Ethyl 4-(trifluoromethyl)-1H-pyrazole-3-carboxylate | — | — | Commercially available, CAS: 934758-94-8 |
| 113 | Ethyl 1-(tetrahydro-2H-pyran-2-yl)-4-(trifluoromethyl)-1H-pyrazole-3-carboxylate | 8 | 112 and 70 | LCMS (System 2, Method E): m/z 293 (M + H)+ (ES+), at 4.21 min, 202 nm |
| 114 | 1-(Tetrahydro-2H-pyran-2-yl)-4-(trifluoromethyl)-1H-pyrazole-3-carboxylic acid | 2 | 113 | LCMS (System 2, Method E): m/z 265 (M + H)+ (ES+), at 1.82 min, 202 nm |
| 115 | 4-Fluoro-1H-pyrazole | — | — | Commercially available, CAS: 35277-02-2 |
| 116 | 4-Fluoro-1-((2-(trimethylsilyl)ethoxy)methyl)-1H-pyrazole | 3 | 115 | $^1$H NMR (400 MHZ, Chloroform-d) δ 0.02 (s, 9H), 0.84-0.94 (m, 2H), |

TABLE 2-continued

Intermediates Table 2

| Intermediate Number | Name | Synthetic Route | Intermediates Used | Data |
|---|---|---|---|---|
| 117 | tert-Butyl (R)-(1-(2-(2,5-dimethyl-1H-pyrrol-1-yl)-6-(4-fluoro-1-((2-(trimethylsilyl) ethoxy)methyl)-1H-pyrazol-5-yl)pyrimidin-4-yl)pyrrolidin-3-yl)(methyl)carbamate | K (Step 1) | 116 and 26 | 3.48-3.56 (m, 2H), 5.29-5.34 (m, 2H), 7.36-7.39 (m, 1H), 7.42-7.45 (m, 1H). LCMS (System 4, Method F): m/z 586 (M + H)$^+$ (ES$^+$), at 3.12 min, 254 nm |
| 118 | tert-Butyl (R)-(1-(2-amino-6-(4-fluoro-1-((2-(trimethylsilyl)ethoxy)methyl)-1H-pyrazol-5-yl)pyrimidin-4-yl)pyrrolidin-3-yl)(methyl)carbamate | 11 | 117 | LCMS (System 5, Method H): m/z 508 (M + H)$^+$ (ES$^+$), at 1.84 min, 205 nm |
| 119 | tert-Butyl azetidin-3-yl(methyl)carbamate | — | — | Commercially available, CAS: 577777-20-9 |
| 120 | 4-bromo-1H-Pyrazole-3-carboxylic acid, | — | — | Commercially available, CAS: 13745-17-0 |
| 121 | 4-(methylthio)-1H-pyrazole-3-carboxylic acid | 12 | | LCMS (System 1, Method B): m/z 159 (M + H)$^+$ (ES$^+$), at 1.22 min, 230 nm |
| 122 | 4,5-Dimethyl-1H-pyrazole-3-carboxylic acid | — | — | Commercially available, CAS: 89831-40-3 |
| 123 | 3-Methyl-4-(trifluoromethyl)-1H-pyrazole | — | — | Commercially available, CAS: 864239-61-2 |
| 124 | 1:1 mixture of 3-methyl-4-(trifluoromethyl)-1-((2-(trimethylsilyl)ethoxy)methyl)-1H-pyrazole and 5-methyl-4-(trifluoromethyl)-1-((2-(trimethylsilyl)ethoxy)methyl)-1H-pyrazole | 3 | 123 | LCMS (System 4, Method F): no mass ion, at 2.59 min, 254 nm |
| 125 | 4-fluoro-5-methyl-1H-pyrazole-3-carboxylic acid | — | — | Commercially available, CAS: 681034-58-2 |
| 126 | 4-Chloro-5-methyl-1H-pyrazole-3-carboxylic acid | — | — | Commercially available, CAS: 29400-84-8 |
| 127 | 4-methoxy-5-methyl-1-(tetrahydro-2H-pyran-2-yl)-1H-pyrazole-3-carboxylic acid | 13 | 30 | LCMS (System LCMS 2, Method E): m/z 241 (M + H)$^+$ (ES$^+$), at 1.71 min, 232 nm |
| 128 | 3-(Difluoromethyl)-4-methyl-1H-pyrazole | — | — | Commercially available, CAS: 1245772-27-3 |
| 129 | (3-(difluoromethyl)-4-methyl-1-(tetrahydro-2H-pyran-2-yl)-1H-pyrazol-5-yl) boronic acid | 14 | 128 | LCMS (System LCMS 2, Method E): m/z 261 (M + H)$^+$ (ES$^+$), at 3.06 min, 234 nm |
| 130 | 4-Methyl-3-trifluoromethylpyrazole | — | — | Commercially available, CAS: 153085-14-4 |
| 131 | 4-methyl-3-(trifluoromethyl)-1-((2-(trimethylsilyl)ethoxy)methyl)-1H-pyrazole | 3 | 130 | LCMS (System LCMS 4, Method F): no mass ion, at 2.68 min, 254 nm |
| 132 | 5-Ethyl-4-fluoro-1H-pyrazole-3-carboxylicacid | — | — | Commercially available, CAS: 681034-63-9 |
| 133 | 3-Chloro-4-methyl-1H-pyrazole | — | — | Commercially available, CAS: 134589-56-3 |
| 134 | 3-chloro-4-methyl-1-((2-(trimethylsilyl)ethoxy)methyl)-1H-pyrazole contains some regioisomer | 3 | 133 | LCMS (System LCMS 4, Method F): no mass ion, at 2.57 min, 254 nm |
| 135 | 4,5-Dichloro-1H-pyrazole-3-carboxylic acid | — | — | Commercially available, CAS: 115964-19-7 |
| 136 | 5-chloro-4-methyl-1H-pyrazole-3-carboxylic acid | — | — | Commercially available, CAS: 1934369-17-1 |

| Ex. No. | Name | Synthetic Method and Intermediates Used | Isolation Method | $^1$H NMR | LCMS System and Method | LCMS data |
|---|---|---|---|---|---|---|
| 1-1 | (R)-4-(3-(Methylamino)pyrrolidin-1-yl)- | A 1, 2 and 3 | RP HPLC | $^1$H NMR (400 MHz, DMSO-d6) δ 1.70-1.91 (m, 1H), 1.97-2.19 (m, 1H), 2.33 (s, 3H), 2.94-3.78 (m, 5H), 5.95 (br. s, 2H), 6.28 (s, 1H), 6.70 (s, 1H), 7.67 (br. s, 1H), 13.05 (br. s, 1H) | System 2 Method E | m/z 260 (M + H)$^+$ (ES$^+$), at |

-continued

| Ex. No. | Name | Synthetic Method and Intermediates Used | Isolation Method | ¹H NMR | LCMS System and Method | LCMS data |
|---|---|---|---|---|---|---|
| | 6-(1H-pyrazol-5-yl) pyrimidin-2-amine | | | One exchangeable proton not observed. | | 1.69 min, 240 nm |
| 1-2 | (R)-4-(1-Methyl-1H-pyrazol-5-yl)-6-(3-(methylamino) pyrrolidin-1-yl) pyrimidin-2-amine dihydrochloride | B 1, 3 and 5 | Solid isolated from deprotection step | ¹H NMR (400 MHz, DMSO-d6) δ 2.23-2.40 (m, 2H), 2.56-2.63 (m, 3H), 3.64-3.73 (m, 1H), 3.81-3.96 (m, 4H), 4.06 (s, 3H), 6.47 (s, 1H), 6.91 (d, J = 2.0 Hz, 1H), 7.64 (d, J = 2.1 Hz, 1H), 9.33-9.61 (m, 2H), 9.78 (br. s, 1H), 12.89 (br. s, 1H) One exchangeable proton not observed. | System 2 Method E | m/z 274 (M + H)⁺ (ES⁺), at 2.01 min, 202 nm |
| 2-1 | (R)-4-(1-Methyl-1H-pyrazol-3-yl)-6-(3-(methylamino) pyrrolidin-1-yl) pyrimidin-2-amine | C 4 and 6 | RP HPLC | ¹H NMR (400 MHz, DMSO-d6) δ 1.65-1.84 (m, 1H), 1.93-2.09 (m, 1H), 2.29 (s, 3H), 3.02-3.24 (m, 2H), 3.24-3.62 (m, 3H), 3.88 (s, 3H), 5.93 (br. s, 2H), 6.21 (s, 1H), 6.64 (d, J = 2.3 Hz, 1H), 7.70 (d, J = 2.2 Hz, 1H) One exchangeable proton not observed. | System 3 Method D | m/z 274 (M + H)⁺ (ES⁺), at 1.91 min, 202 nm |
| 2-2 | (R)-4-(1-(Difluoromethyl)-1H-pyrazol-3-yl)-6-(3-(methylamino) pyrrolidin-1-yl) pyrimidin-2-amine dihydrochloride | D 7, 8 and 4 | Solid isolated from deprotection step | ¹H NMR (400 MHz, DMSO-d6) δ 2.25-2.44 (m, 2H), 2.56-2.65 (m, 3H), 3.64-3.78 (m, 1H), 3.79-4.03 (m, 4H), 6.83-6.89 (m, 1H), 7.48-7.53 (m, 1H), 7.97 (t, J = 57.8 Hz, 1H), 8.51-8.56 (m, 1H), 9.29-9.87 (m, 1H), 12.24-12.44 (m, 1H) Two exchangeable protons not observed. | System 4 Method G | m/z 310 (M + H)⁺ (ES⁺), at 2.32 min, 254 nm |
| 3-1 | (R)-4-(3-Methyl-1H-pyrazol-5-yl)-6-(3-(methylamino) pyrrolidin-1-yl) pyrimidin-2-amine | E 4 and 9 | RP HPLC | ¹H NMR (400 MHz, Methanol-d4) δ 1.81-2.02 (m, 1H), 2.16-2.36 (m, 4H), 2.44 (s, 3H), 3.33-3.44 (m, 2H), 3.46-3.58 (m, 1H), 3.59-3.83 (m, 2H), 6.34 (s, 1H), 6.57 (s, 1H) Four exchangeable protons not observed. | System 3 Method D | m/z 274 (M + H)⁺ (ES⁺), at 1.99 min, 240 nm |
| 3-2 | (R)-4-(3-Cyclopropyl-1H-pyrazol-5-yl)-6-(3-(methylamino) pyrrolidin-1-yl) pyrimidin-2-amine dihydrochloride | D (Steps 2 and 3) 10 and 4 | Solid isolated from deprotection step | ¹H NMR (400 MHz, DMSO-d6) δ 0.71-0.77 (m, 2H), 0.99-1.06 (m, 2H), 1.96-2.05 (m, 1H), 2.31-2.42 (m, 1H), 2.55-2.64 (m, 4H), 3.78-3.96 (m, 5H), 6.59-6.64 (m, 1H), 6.85-6.90 (m, 1H), 9.35-9.89 (m, 2H), 12.07-12.18 (m, 1H) Three exchangeable protons not observed. | System 4 Method G | m/z 300 (M + H)⁺ (ES⁺), at 2.45 min, 254 nm |
| 3-3 | (R)-4-(3-(Difluoromethyl)-1H-pyrazol-5-yl)-6-(3-(methylamino) pyrrolidin-1-yl) pyrimidin-2-amine | F 12, 13 and 4 | RP chromatography | ¹H NMR (400 MHz, Methanol-d4) δ 2.20-2.47 (m, 1H), 2.47-2.68 (m, 1H), 2.71-2.87 (m, 3H), 3.78-4.20 (m, 5H), 6.71-6.79 (m, 1H), 6.87-7.21 (m, 1H), 7.29-7.41 (m, 1H). Four exchangeable protons not observed. | System 4 Method G | m/z 310 (M + H)⁺ (ES⁺), at 2.46 min, 254 nm |
| 3-4 | (R)-4-(3-(Methylamino) pyrrolidin-1-yl)-6-(3-(trifluoromethyl)-1H-pyrazol-5-yl) pyrimidin-2-amine ditrifluoroacetate | G 15, 16, 17 and 3 | RP HPLC | ¹H NMR (400 MHz, Methanol-d4) δ 2.21-2.66 (m, 2H), 2.81 (s, 3H), 3.70-4.16 (m, 5H), 6.76 (s, 1H), 7.52 (s, 1H) Six exchangeable protons not observed. | System 2 Method E | m/z 328 (M + H)⁺ (ES⁺), at 2.70 min, 243 nm |
| 3-5 | (R)-4-(3-Aminopyrrolidin-1-yl)-6-(3-(trifluoromethyl)-1H-pyrazol-5-yl) pyrimidin-2-amine | G 15, 16, 17 and 18 | RP HPLC | ¹H NMR (400 MHz, Methanol-d4) δ 1.76-1.99 (m, 1H), 2.07-2.34 (m, 1H), 3.40-3.88 (m, 4H), 6.30 (s, 1H), 7.14 (s, 1H) Five exchangeable protons not observed. One proton obscured by solvent peak. | System 2 Method E | m/z 314 (M + H)⁺ (ES⁺), at 2.60 min, 202 nm |
| 4-1 | (R)-4-(4-Methyl-1H-pyrazol-5-yl)-6-(3-(methylamino) pyrrolidin-1-yl) pyrimidin-2-amine | H 1, 19 and 3 | RP HPLC | ¹H NMR (400 MHz, Methanol-d4) δ 1.91-2.05 (m, 1H), 2.24-2.35 (m, 4H), 2.49 (s, 3H), 3.40-3.83 (m, 5H), 6.16 (s, 1H), 7.48 (s, 1H) Four exchangeable protons not observed. | System 2 Method E | m/z 274 (M + H)⁺ (ES⁺), at 2.26 min, 241 nm |
| 4-2 | (R)-4-(4-Ethyl-1H-pyrazol-5-yl)-6-(3-(methylamino) pyrrolidin-1-yl) pyrimidin-2-amine | I 22, 13 and 4 | RP HPLC | ¹H NMR (400 MHz, Methanol-d4) δ 1.22 (t, J = 7.5 Hz, 3H), 1.83-1.97 (m, 1H), 2.17-2.29 (m, 1H), 2.42 (s, 3H), 2.79 (q, J = 7.5 Hz, 2H), 3.32-3.42 (m, 2H), 3.44-3.55 (m, 1H), 3.57-3.81 (m, 2H), 6.12 (s, 1H), 7.48 (s, 1H) Four exchangeable protons not observed. | System 4 Method G | m/z 288 (M + H)⁺ (ES⁺), at 3.21 min, 254 nm |
| 4-3 | (R)-4-(4-Chloro-1H-pyrazol-5-yl)-6-(3-(methylamino) pyrrolidin-1-yl)pyrimidin-2-amine | J 24, 13 and 26 | RP HPLC | ¹H NMR (400 MHz, Chloroform-d) δ 1.74-2.00 (m, 1H), 2.10-2.25 (m, 1H), 2.49 (s, 3H), 3.00-3.93 (m, 5H), 4.88 (br. s, 2H), 6.57 (s, 1H), 7.51-7.61 (m, 1H) Two exchangeable protons not observed. | System 4 Method G | m/z 294/296 (M + H)⁺ (ES⁺), at 2.51 min, 254 nm |

-continued

| Ex. No. | Name | Synthetic Method and Intermediates Used | Isolation Method | $^1$H NMR | LCMS System and Method | LCMS data |
|---|---|---|---|---|---|---|
| 4-4 | (R)-4-(4-Methoxy-1H-pyrazol-5-yl)-6-(3-(methylamino)pyrrolidin-1-yl)pyrimidin-2-amine | K 28 and 26 | RP HPLC | $^1$H NMR (400 MHz, Deuterium Oxide) δ 2.29-2.42 (m, 1H), 2.53-2.67 (m, 1H), 2.83 (s, 3H), 3.74-3.89 (m, 3H), 3.95 (s, 3H), 4.02-4.11 (m, 2H), 6.61 (s, 1H), 7.68 (s, 1H).<br>Four exchangeable protons not observed. | System 4 Method G | m/z 290 (M + H)$^+$ (ES$^+$), at 2.15 min, 254 nm |
| 4-5 | (R)-4-(3-Aminopyrrolidin-1-yl)-6-(4-methyl-1H-pyrazol-5-yl)pyrimidin-2-amine | G 29, 16, 17 and 18 TFA/DCM used in final step | Free base generated from TFA salt | $^1$H NMR (400 MHz, Methanol-d4) δ 1.76-1.94 (m, 1H), 2.15-2.27 (m, 1H), 2.31 (s, 3H), 3.42-3.83 (m, 5H), 6.12 (s, 1H), 7.45 (s, 1H)<br>Five exchangeable protons not observed. | System 2 Method E | m/z 260 (M + H)$^+$ (ES$^+$), at 1.90 min, 240 nm |
| 5-1 | (R)-4-(1,5-Dimethyl-1H-pyrazol-3-yl)-6-(3-(methylamino)pyrrolidin-1-yl)pyrimidin-2-amine diformate | G 31, 16, 17 and 3 TFA/DCM used in final step | RP HPLC | $^1$H NMR (400 MHz, Methanol-d4) δ 2.37 (s, 3H), 2.45-2.64 (m, 2H), 2.75-2.84 (m, 3H), 3.53-3.59 (m, 1H), 3.63-3.72 (m, 1H), 3.72-4.11 (m, 6H), 6.53-6.58 (m, 1H), 6.78 (s, 1H)<br>Five exchangeable protons not observed. | System 2 Method E | m/z 288 (M + H)$^+$ (ES$^+$), at 2.06 min, 226 nm |
| 5-2 | (R)-4-(1-(Difluoromethyl)-5-methyl-1H-pyrazol-3-yl)-6-(3-(methylamino)pyrrolidin-1-yl)pyrimidin-2-amine | G 32, 16, 17 and 3 TFA/DCM used in final step | RP HPLC | $^1$H NMR (400 MHz, DMSO-d6) δ 1.68-1.86 (m, 1H), 1.92-2.10 (m, 1H), 2.29 (s, 3H), 2.44 (s, 3H), 3.01-3.26 (m, 2H), 3.38-3.64 (m, 3H), 6.07 (br. s, 2H), 6.23 (s, 1H), 6.68 (s, 1H), 7.85 (t, J = 57.9 Hz, 1H)<br>One exchangeable proton not observed. | System 3 Method D | m/z 324 (M + H)$^+$ (ES$^+$), at 2.59 min, 240 nm |
| 6-1 | (R)-4-(1,4-Dimethyl-1H-pyrazol-3-yl)-6-(3-(methylamino)pyrrolidin-1-yl)pyrimidin-2-amine | G 34, 16, 17 and 3 TFA/DCM used in final step | RP HPLC | $^1$H NMR (400 MHz, Methanol-d4) δ 1.85-2.01 (m, 1H), 2.19-2.32 (m, 4H), 2.44 (s, 3H), 3.34-3.43 (m, 2H), 3.47-3.59 (m, 1H), 3.60-3.80 (m, 2H), 3.88 (s, 3H), 6.17 (s, 1H), 7.43 (s, 1H)<br>Three exchangeable protons not observed. | System 2 Method E | m/z 288 (M + H)$^+$ (ES$^+$), at 2.21 min, 241 nm |
| 6-2 | (R)-4-(1-(Difluoromethyl)-4-methyl-1H-pyrazol-3-yl)-6-(3-(methylamino)pyrrolidin-1-yl)pyrimidin-2-amine | G 36, 16, 17 and 3 TFA/DCM used in final step | RP HPLC | $^1$H NMR (400 MHz, Methanol-d4) δ 1.84-2.00 (m, 1H), 2.20-2.35 (m, 4H), 2.43 (s, 3H), 3.35-3.84 (m, 5H), 6.26 (s, 1H), 7.44 (t, J = 59.8 Hz, 1H), 7.87 (s, 1H)<br>Three exchangeable protons not observed. | System 3 Method E | m/z 324 (M + H)$^+$ (ES$^+$), at 2.60 min, 214 nm |
| 7-1 | (R)-4-(3,4-Dimethyl-1H-pyrazol-5-yl)-6-(3-(methylamino)pyrrolidin-1-yl)pyrimidin-2-amine dihydrochloride | L 37, 21, 13, 38 and 4 | Solid isolated from deprotection step | $^1$H NMR (400 MHz, Methanol-d4) δ 2.18-2.30 (m, 6H), 2.32-2.69 (m, 2H), 2.75-2.90 (m, 3H), 3.76-4.15 (m, 5H), 6.30-6.41 (m, 1H)<br>Six exchangeable protons not observed. | System 4 Method G | m/z 288 (M + H)$^+$ (ES$^+$), at 2.96 min, 254 nm |
| 7-2 | (R)-4-(4-Chloro-3-methyl-1H-pyrazol-5-yl)-6-(3-(methylamino)pyrrolidin-1-yl)pyrimidin-2-amine | L 39, 21, 13, 38 and 4 | RP HPLC | $^1$H NMR (400 MHz, Methanol-d4) δ 2.24-2.44 (m, 4H), 2.46-2.65 (m, 1H), 2.77-2.86 (m, 3H), 3.73-4.15 (m, 5H), 6.80-6.89 (m, 1H)<br>Four exchangeable protons not observed. | System 4 Method G | m/z 308/310 (M + H)$^+$ (ES$^+$), at 3.13 min, 254 nm |
| 7-3 | (R)-4-(3-Ethyl-4-methyl-1H-pyrazol-5-yl)-6-(3-(methylamino)pyrrolidin-1-yl)pyrimidin-2-amine | L 40, 21, 13, 38 and 4 | RP HPLC | $^1$H NMR (400 MHz, Chloroform-d) δ 1.25 (t, J = 7.6 Hz, 3H), 1.82-1.93 (m, 1H), 2.13-2.21 (m, 1H), 2.23 (s, 3H), 2.49 (s, 3H), 2.65 (q, J = 7.6 Hz, 2H), 3.21-3.75 (m, 5H), 4.78 (br. s, 2H), 6.02 (s, 1H)<br>Two exchangeable protons not observed. | System 4 Method G | m/z 302 (M + H)$^+$ (ES$^+$), at 3.45 min, 254 nm |
| 7-4 | (R)-4-(3-(Methylamino)pyrrolidin-1-yl)-6-(2,4,5,6-tetrahydrocyclopenta[c]pyrazol-3-yl)pyrimidin-2-amine dihydrochloride | L 41, 21, 42 and 38 absent | Solid isolated from deprotection step | 1H NMR (400 MHz, Methanol-d4) δ 2.22-2.54 (m, 1H), 2.55-2.75 (m, 3H), 2.78-2.95 (m, 7H), 3.73-4.15 (m, 5H), 6.17-6.21 (m, 1H)<br>Six exchangeable protons not observed. | System 4 Method G | m/z 300 (M + H)$^+$ (ES$^+$), at 2.62 min, 254 nm |

-continued

| Ex. No. | Name | Synthetic Method and Intermediates Used | Isolation Method | $^1$H NMR | LCMS System and Method | LCMS data |
|---|---|---|---|---|---|---|
| 7-5 | (R)-4-(2H-Indazol-3-yl)-6-(3-(methylamino)pyrrolidin-1-yl)pyrimidin-2-amine dihydrochloride | D (Steps 2 and 3) 43 and 4 | Solid isolated from deprotection step | $^1$H NMR (400 MHz, Methanol-d4) δ 2.33-2.48 (m, 1H), 2.54-2.71 (m, 1H), 2.85 (s, 3H), 3.75-4.18 (m, 5H), 6.65 (s, 1H), 7.32-7.51 (m, 1H), 7.57-7.68 (m, 1H), 7.82-7.94 (m, 1H), 8.36-8.51 (m, 1H)<br>Six exchangeable protons not observed. | System 4 Method G | m/z 310 (M + H)$^+$ (ES$^+$), at 3.47 min, 254 nm |
| 7-6 | (R)-4-(3-Amino-pyrrolidin-1-yl)-6-(3,4-dimethyl-1H-pyrazol-5-yl)pyrimidin-2-amine dihydrochloride | I 44, 13 and 45 | Solid isolated from deprotection step | $^1$H NMR (400 MHz, Methanol-d4) δ 2.26 (s, 3H), 2.30 (s, 3H), 2.44-2.67 (m, 2H), 3.82-3.95 (m, 3H), 4.02-4.12 (m, 2H), 6.33, 6.29 (2 × s, 1H).<br>Seven exchangeable protons not observed. | System 4 Method G | m/z 274 (M + H)$^+$ (ES$^+$), at 2.49 min, 254 nm |
| 7-7 | (R)-4-(3-Amino-pyrrolidin-1-yl)-6-(4-chloro-3-methyl-1H-pyrazol-5-yl)pyrimidin-2-amine dihydrochloride | I 46, 13 and 45 | Solid isolated from deprotection step | $^1$H NMR (400 MHz, Methanol-d4) δ 2.18-2.33 (m, 1H), 2.35 (s, 3H), 2.47-2.66 (m, 1H), 3.73-4.19 (m, 5H), 6.81, 6.86 (2 × s, 1H).<br>Seven exchangeable protons not observed. | System 4 Method G | m/z 294/296 (M + H)$^+$ (ES$^+$), at 2.53 min, 254 nm |
| 7-8 | (R)-4-(3-Amino-pyrrolidin-1-yl)-6-(3-ethyl-4-methyl-1H-pyrazol-5-yl)pyrimidin-2-amine | L 40, 21, 13, 38 and 45 | RP HPLC | $^1$H NMR (400 MHz, Methanol-d4) δ 1.17-1.28 (m, 3H), 1.77-1.93 (m, 1H), 2.15-2.28 (m, 4H), 2.61-2.71 (m, 2H), 3.17-3.30 (m, 1H), 3.44-3.58 (m, 1H), 3.60-3.81 (m, 3H), 6.11 (s, 1H)<br>Five exchangeable protons not observed | System 4 Method G | m/z 288 (M + H)$^+$ (ES$^+$), at 2.91 min, 254 nm |
| 8-1 | (R)-4-(3-(Methylamino)pyrrolidin-1-yl)-6-(1H-pyrazol-4-yl)pyrimidin-2-amine | C 4 and 47 HCl/dioxane used in final step | RP HPLC | $^1$H NMR (400 MHz, DMSO-d6) δ 1.65-1.83 (m, 1H), 1.94-2.09 (m, 1H), 2.29 (s, 3H), 3.09-3.25 (m, 2H), 3.38-3.64 (m, 3H), 5.84 (br. s, 2H), 6.04 (s, 1H), 7.77-8.37 (m, 2H), 12.98 (br. s, 1H)<br>One exchangeable proton not observed. | System 2 Method E | m/z 260 (M + H)$^+$ (ES$^+$), at 1.70 min, 239 nm |
| 8-2 | (R)-4-(1-Methyl-1H-pyrazol-4-yl)-6-(3-(methylamino)pyrrolidin-1-yl)pyrimidin-2-amine | C 4 and 48 | RP HPLC | $^1$H NMR (400 MHz, DMSO-d6) δ 1.62-1.83 (m, 1H), 1.94-2.09 (m, 1H), 2.29 (s, 3H), 3.07-3.26 (m, 2H), 3.36-3.60 (m, 3H), 3.85 (s, 3H), 5.83 (br. s, 2H), 5.99 (s, 1H), 7.88 (s, 1H), 8.13 (s, 1H)<br>One exchangeable proton not observed. | System 2 Method E | m/z 274 (M + H)$^+$ (ES$^+$), at 1.85 min, 202 nm |
| 8-3 | (R)-4-(1-Ethyl-1H-pyrazol-4-yl)-6-(3-(methylamino)pyrrolidin-1-yl)pyrimidin-2-amine dihydrochloride | D (Steps 2 and 3) 49 and 4 | Solid isolated from deprotection step | $^1$H NMR (400 MHz, Methanol-d4) δ 1.49-1.55 (m, 3H), 2.22-2.66 (m, 2H), 2.78-2.85 (m, 3H), 3.73-4.13 (m, 5H), 4.24-4.33 (m, 2H), 6.49-6.56 (m, 1H), 8.15-8.18 (m, 1H), 8.48-8.54 (m, 1H)<br>Five exchangeable protons not observed. | System 4 Method G | m/z 288 (M + H)$^+$ (ES$^+$), at 2.24 min, 254 nm |
| 8-4 | (R)-4-(1-Cyclopropyl-1H-pyrazol-4-yl)-6-(3-(methylamino)pyrrolidin-1-yl)pyrimidin-2-amine | C 4 and 50 | RP HPLC | $^1$H NMR (400 MHz, DMSO-d6) δ 0.91-1.10 (m, 4H), 1.65-1.83 (m, 1H), 1.93-2.09 (m, 1H), 2.29 (s, 3H), 3.06-3.59 (m, 5H), 3.68-3.80 (m, 1H), 5.83 (br. s, 2H), 6.02 (s, 1H), 7.87 (s, 1H), 8.23 (s, 1H)<br>One exchangeable proton not observed. | System 2 Method E | m/z 300 (M + H)$^+$ (ES$^+$), at 2.09 min, 202 nm |
| 8-5 | (R)-4-(1-Cyclobutyl-1H-pyrazol-4-yl)-6-(3-(methylamino)pyrrolidin-1-yl)pyrimidin-2-amine | C 4 and 51 HCl/dioxane used in final step | RP HPLC | $^1$H NMR (400 MHz, Methanol-d4) δ 1.81-2.00 (m, 3H), 2.16-2.30 (m, 1H), 2.38-2.64 (m, 7H), 3.29-3.42 (m, 3H), 3.45-3.80 (m, 3H), 6.12 (s, 1H), 8.00 (s, 1H), 8.21 (s, 1H)<br>Three exchangeable protons not observed. | System 2 Method E | m/z 314 (M + H)$^+$ (ES$^+$), at 2.38 min, 202 nm |
| 8-6 | (R)-4-(1-(Difluoromethyl)-1H-pyrazol-4-yl)-6-(3-(methylamino)pyrrolidin-1-yl)pyrimidin-2-amine | C 4 and 52 HCl/dioxane used in final step | RP HPLC | $^1$H NMR (400 MHz, DMSO-d6) δ 1.65-2.13 (m, 3H), 2.30 (s, 3H), 3.13-3.25 (m, 2H), 3.39-3.66 (m, 3H), 5.95 (br. s, 2H), 6.18 (s, 1H), 7.84 (t, J = 59.1 Hz, 1H), 8.25 (s, 1H), 8.67 (s, 1H) | System 2 Method E | m/z 310 (M + H)$^+$ (ES$^+$), at 2.26 min, 202 nm |
| 8-7 | (R)-4-(3-(Methylamino)pyrrolidin-1-yl)-6-(1-(trifluoromethyl)-1H-pyrazol-4-yl)pyrimidin-2-amine dihydrochloride | D (Steps 2 and 3) 53 and 4 | Solid isolated from deprotection step | $^1$H NMR (400 MHz, DMSO-d6) δ 2.19-2.45 (m, 2H), 2.56-2.66 (m, 3H), 3.61-3.73 (m, 1H), 3.76-4.02 (m, 4H), 6.74-6.87 (m, 1H), 8.80-8.90 (m, 1H), 9.21-9.69 (m, 3H), 13.40-13.57 (m, 1H)<br>Two exchangeable proton not observed. | System 4 Method G | m/z 328 (M + H)$^+$ (ES$^+$), at 2.74 min, 254 nm |
| 8-8 | (R)-4-(3-(Methylamino)pyrrolidin-1-yl)-6-(1-(2,2,2-trifluoroethyl)-1H-pyrazol-4-yl)pyrimidin-2-amine dihydrochloride | D (Steps 2 and 3) 54 and 4 | Solid isolated from deprotection step | $^1$H NMR (400 MHz, Methanol-d4) δ 2.19-2.67 (m, 2H), 2.79-2.86 (m, 3H), 3.74-4.13 (m, 5H), 5.06-5.16 (m, 2H), 6.54-6.62 (m, 1H), 8.24-8.27 (m, 1H), 8.58-8.63 (m, 1H)<br>Five exchangeable protons not observed. | System 4 Method G | m/z 342 (M + H)$^+$ (ES$^+$), at 2.54 min, 254 nm |

-continued

| Ex. No. | Name | Synthetic Method and Intermediates Used | Isolation Method | $^1$H NMR | LCMS System and Method | LCMS data |
|---|---|---|---|---|---|---|
| 8-9 | (R)-2-(4-(2-Amino-6-(3-(methylamino)pyrrolidin-1-yl)pyrimidin-4-yl)-1H-pyrazol-1-yl)ethan-1-ol | C 4 and 55 | RP HPLC | $^1$H NMR (400 MHz, Methanol-d4) δ 1.82-2.03 (m, 1H), 2.18-2.32 (m, 1H), 2.43-2.49 (m, 1H), 3.33-3.56 (m, 3H), 3.58-3.78 (m, 2H), 3.91 (t, J = 5.3 Hz, 2H), 4.26 (t, J = 5.3 Hz, 2H), 6.11(s, 1H), 8.01 (s, 1H), 8.18 (s, 1H) Four exchangeable protons not observed. | System 2 Method E | m/z 304 (M + H)$^+$ (ES$^+$), at 1.69 min, 242 nm |
| 8-10 | (R)-4-(1-(2-Methoxyethyl)-1H-pyrazol-4-yl)-6-(3-(methylamino)pyrrolidin-1-yl)pyrimidin-2-amine | C 4 and 56 | RP HPLC | $^1$H NMR (400 MHz, DMSO-d6) δ 1.70-1.87 (m, 1H), 1.95-2.14 (m, 1H), 2.33 (s, 3H), 3.18-3.26 (m, 4H), 3.39-3.57 (m, 4H), 3.69 (t, J = 5.2 Hz, 2H), 4.27 (t, J = 5.2 Hz, 2H), 5.86 (br. s, 2H), 6.01 (s, 1H), 7.92 (s, 1H), 8.14 (s, 1H) One exchangeable proton not observed. | System 2 Method E | m/z 318 (M + H)$^+$ (ES$^+$), at 1.96 min, 254 nm |
| 8-11 | (R)-4-(3-(Methylamino)pyrrolidin-1-yl)-6-(1-(oxetan-3-yl)-1H-pyrazol-4-yl)pyrimidin-2-amine | C 4 and 57 | RP HPLC | $^1$H NMR (400 MHz, Methanol-d4) δ 1.84-2.01 (m, 1H), 2.17-2.33 (m, 1H), 2.46 (s, 3H), 3.33-3.80 (m, 5H), 4.99-5.12 (m, 4H), 5.52-5.66 (m, 1H), 6.14 (s, 1H), 8.10 (s, 1H), 8.28 (s, 1H) Three exchangeable protons not observed. | System 2 Method E | m/z 316 (M + H)$^+$ (ES$^+$), at 1.84 min, 202 nm |
| 8-12 | (R)-3-(4-(2-Amino-6-(3-(methylamino)pyrrolidin-1-yl)pyrimidin-4-yl)-1H-pyrazol-1-yl)propanenitrile | C 4 and 58 | RP HPLC | $^1$H NMR (400 MHz, Methanol-d4) δ 2.01-2.15 (m, 1H), 2.30-2.45 (m, 1H), 2.61 (s, 3H), 3.07 (t, J = 6.4 Hz, 2H), 3.51-3.74 (m, 4H), 3.76-3.85 (m, 1H), 4.48 (t, J = 6.4 Hz, 2H), 6.19 (s, 1H), 8.07 (s, 1H), 8.26 (s, 1H) Three exchangeable protons not observed. | System 2 Method E | m/z 313 (M + H)$^+$ (ES$^+$), at 1.89 min, 240 nm |
| 8-13 | (R)-2-(4-(2-amino-6-(3-(methylamino)pyrrolidin-1-yl)pyrimidin-4-yl)-1H-pyrazol-1-yl)acetonitrile trifluoroacetate | C 4 and 59 | RP HPLC | $^1$H NMR (400 MHz, Methanol-d4) δ 2.17-2.43 (m, 1H), 2.45-2.68 (m, 1H), 2.82 (s, 3H), 3.71-4.12 (m, 5H), 5.47 (s, 2H), 6.53 (s, 1H), 8.23 (s, 1H), 8.53 (s, 1H) Three exchangeable protons not observed. | System 2 Method E | m/z 299 (M + H)$^+$ (ES$^+$), at 1.88 min, 202 nm |
| 8-14 | Ethyl 3-(4-(2-amino-6-((R)-3-(methylamino)pyrrolidin-1-yl)pyrimidin-4-yl)-1H-pyrazol-1-yl)piperidine-1-carboxylate | C 4 and 63 K$_2$CO$_3$ used as base in Step 1 | RP HPLC | $^1$H NMR (400 MHz, DMSO-d6) δ 1.11-1.26 (m, 3H), 1.44-1.63 (m, 1H), 1.72-1.83 (m, 2H), 1.94-2.21 (m, 3H), 2.29 (s, 3H), 2.83-2.99 (m, 1H), 3.09-3.26 (m, 3H), 3.41-3.62 (m, 3H), 3.84-3.95 (m, 1H), 3.99-4.31 (m, 4H), 5.84 (br. s, 2H), 6.03 (s, 1H), 7.95 (s, 1H), 8.26 (s, 1H) One exchangeable proton not observed. | System 2 Method E | m/z 415 (M + H)$^+$ (ES$^+$), at 2.59 min, 202 nm |
| 8-15 | (R)-4-(3-Aminopyrrolidin-1-yl)-6-(1-(trifluoromethyl)-1H-pyrazol-4-yl)pyrimidin-2-amine dihydrochloride | D (Steps 2 and 3) 53 and 45 | Solid isolated from deprotection step | $^1$H NMR (400 MHz, Methanol-d4) δ 2.12-2.69 (m, 2H), 3.76-4.21 (m, 5H), 6.66-6.72 (m, 1H), 8.45-8.50 (m, 1H), 9.01-9.08 (m, 1H) Six exchangeable protons not observed. | System 4 Method G | m/z 314 (M + H)$^+$ (ES$^+$), at 2.40 min, 254 nm |
| 8-16 | 4-(3-(Methylamino)azetidin-1-yl)-6-(1-(trifluoromethyl)-1H-pyrazol-4-yl)pyrimidin-2-amine ditrifluoroacetate | D (Steps 2 and 3) 53 and 65 TFA/DCM used in Step 3 | Solid isolated from deprotection step | 1H NMR (400 MHz, Methanol-d4) δ 2.78 (s, 3H), 4.22-4.51 (m, 3H), 4.53-4.73 (m, 2H), 6.51 (s, 1H), 8.39-8.49 (m, 1H), 8.98-9.08 (m, 1H) Five exchangeable protons not observed. | System 4 Method G | m/z 314 (M + H)$^+$ (ES$^+$), at 2.66 min, 254 nm |
| 8-17 | (R)-4-(3-Aminopyrrolidin-1-yl)-6-(1-ethyl-1H-pyrazol-4-yl)pyrimidin-2-amine dihydrochloride | D (Steps 2 and 3) 49 and 45 | Solid isolated from deprotection step | $^1$H NMR (400 MHz, Methanol-d4) δ 1.52 (t, J = 7.3 Hz, 3H), 2.12-2.38 (m, 1H), 2.40-2.64 (m, 1H), 3.74-3.95 (m, 3H), 3.97-4.18 (m, 2H), 4.28 (q, J = 7.3 Hz, 2H), 6.49-6.54 (m, 1H), 8.17-8.21 (m, 1H), 8.51-8.58 (m, 1H) Six exchangeable protons not observed. | System 4 Method G | m/z 274 (M + H)$^+$ (ES$^+$), at 1.93 min, 254 nm |
| 8-18 | (R)-4-(3-Aminopyrrolidin-1-yl)-6-(1-(2,2,2-trifluoroethyl)-1H-pyrazol-4-yl)pyrimidin-2-amine dihydrochloride | D (Steps 2 and 3) 54 and 45 | Solid isolated from deprotection step | $^1$H NMR (400 MHz, Methanol-d4) δ 2.13-2.36 (m, 1H), 2.42-2.67 (m, 1H), 3.73-3.97 (m, 3H), 3.98-4.20 (m, 2H), 5.06-5.16 (m, 2H), 6.54-6.59 (m, 1H), 8.23-8.27 (m, 1H), 8.57-8.63 (m, 1H) Six exchangeable protons not observed. | System 4 Method G | m/z 328 (M + H)$^+$ (ES$^+$), at 2.22 min, 254 nm |
| 9-1 | (R)-4-(5-Methyl-1H-pyrazol-4-yl)-6-(3-(methylamino)pyrrolidin-1-yl)pyrimidin-2-amine | C 4 and 68 | RP HPLC | $^1$H NMR (400 MHz, Methanol-d4) δ 1.81-1.99 (m, 1H), 2.17-2.30 (m, 1H), 2.43 (s, 3H), 2.52 (s, 3H), 3.33-3.39 (m, 2H), 3.42-3.55 (m, 1H), 3.56-3.80 (m, 2H), 5.96 (s, 1H), 7.91 (s, 1H) Four exchangeable protons not observed. | System 2 Method E | m/z 274 (M + H)$^+$ (ES$^+$), at 2.73 min, 244 nm |

-continued

| Ex. No. | Name | Synthetic Method and Intermediates Used | Isolation Method | $^1$H NMR | LCMS System and Method | LCMS data |
|---|---|---|---|---|---|---|
| 9-2 | (R)-4-(5-Ethyl-1H-pyrazol-4-yl)-6-(3-(methylamino)pyrrolidin-1-yl)pyrimidin-2-amine | E 4 and 72 K$_2$CO$_3$ used as base in Step 1 | RP HPLC | $^1$H NMR (400 MHz, Methanol-d4) δ 1.26 (t, J = 7.6 Hz, 3H), 1.83-1.99 (m, 1H), 2.16-2.32 (m, 1H), 2.44 (s, 3H), 3.00 (q, J = 7.6 Hz, 2H), 3.33-3.41 (m, 2H), 3.44-3.55 (m, 1H), 3.57-3.84 (m, 2H), 5.96 (s, 1H), 7.89 (s, 1H) Four exchangeable protons not observed. | System 2 Method E | m/z 288 (M + H)$^+$ (ES$^+$), at 2.88 min, 202 nm |
| 9-3 | (R)-4-(5-Isopropyl-1H-pyrazol-4-yl)-6-(3-(methylamino)pyrrolidin-1-yl)pyrimidin-2-amine | C 4 and 73 K$_2$CO$_3$ used as base in Step 1 | RP HPLC | $^1$H NMR (400 MHz, Methanol-d4) δ 1.24-1.39 (m, 6H), 1.83-2.02 (m, 1H), 2.17-2.35 (m, 1H), 2.45 (s, 3H), 3.34-3.86 (m, 6H), 5.94 (s, 1H), 7.82 (s, 1H) Four exchangeable protons not observed. | System 3 Method D | m/z 302 (M + H)$^+$ (ES$^+$), at 2.25 min, 254 nm |
| 9-4 | (R)-4-(5-cyclopropyl-1H-pyrazol-4-yl)-6-(3-(methylamino)pyrrolidin-1-yl)pyrimidin-2-amine ditrifluoroacetate | C 4 and 74 | RP HPLC | $^1$H NMR (400 MHz, Methanol-d4) δ 0.84-0.97 (m, 2H), 1.06-1.18 (m, 2H), 2.03-2.18 (m, 1H), 2.20-2.43 (m, 1H), 2.44-2.68 (m, 1H), 2.77-2.86 (m, 3H), 3.71-4.11 (m, 5H), 6.42-6.56 (m, 1H), 8.06 (s, 1H) Six exchangeable protons not observed. | System 3 Method E | m/z 300 (M + H)$^+$ (ES$^+$), at 2.08 min, 214 nm |
| 9-5 | (R)-4-(5-(Difluoromethyl)-1H-pyrazol-4-yl)-6-(3-(methylamino)pyrrolidin-1-yl)pyrimidin-2-amine trifluoroacetate | E 4 and 77 DCM absent in Step 2 | RP HPLC | $^1$H NMR (400 MHz, Methanol-d4) δ 2.23-2.43 (m, 1H), 2.46-2.66 (m, 1H), 2.80 (s, 3H), 3.62-4.16 (m, 5H), 6.43 (s, 1H), 7.02 (t, J = 53.7 Hz, 1H), 8.34 (s, 1H) Six exchangeable protons not observed. | System 2 Method E | m/z 310 (M + H)$^+$ (ES$^+$), at 2.05 min, 202 nm |
| 9-6 | (R)-4-(3-(Methylamino)pyrrolidin-1-yl)-6-(5-(trifluoromethyl)-1H-pyrazol-4-yl)pyrimidin-2-amine | C 4 and 78 | RP HPLC | $^1$H NMR (400 MHz, DMSO-d6) δ 1.67-1.85 (m, 1H), 1.93-2.09 (m, 1H), 2.28 (s, 3H), 3.12-3.27 (m, 2H), 3.38-3.68 (m, 3H), 5.85-5.97 (m, 3H), 8.29 (s, 1H), 12.88-14.45 (br. s, 1 H) One exchangeable proton not observed. | System 3 Method D | m/z 328 (M + H)$^+$ (ES$^+$), at 2.36 min, 202 nm |
| 9-7 | (R)-4-(3-Amino-pyrrolidin-1-yl)-6-(5-methyl-1H-pyrazol-4-yl)pyrimidin-2-amine | C 45 and 68 | RP HPLC | $^1$H NMR (400 MHz, Methanol-d4) δ 1.80-1.94 (m, 1H), 2.14-2.29 (m, 1H), 2.52 (s, 3H), 3.40-3.84 (m, 5H), 5.96 (s, 1H), 7.92(s, 1H) Five exchangeable protons not observed. | System 2 Method E | m/z 260 (M + H)$^+$ (ES$^+$), at 2.56 min, 202 nm |
| 10-1 | (R)-4-(3,5-Dimethyl-1H-pyrazol-4-yl)-6-(3-(methylamino)pyrrolidin-1-yl)pyrimidin-2-amine | C 4 and 79 | RP HPLC | $^1$H NMR (400 MHz, Methanol-d4) δ 1.87-2.00 (m, 1H), 2.21-2.41 (m, 7H), 2.47 (s, 3H), 3.35-3.57 (m, 3H), 3.58-3.80 (m, 2H), 5.84 (s, 1H) Four exchangeable protons not observed. | System 3 Method D | m/z 288 (M + H)$^+$ (ES$^+$), at 1.94 min, 242 nm |
| 11-1 | (R)-4-(1,3-Dimethyl-1H-pyrazol-4-yl)-6-(3-(methylamino)pyrrolidin-1-yl)pyrimidin-2-amine | M 4 and 80 | RP HPLC | $^1$H NMR (400 MHz, DMSO-d6) δ 1.66-1.82 (m, 1H), 1.94-2.09 (m, 1H), 2.30 (s, 3H), 2.39 (s, 3H), 3.04-3.25 (m, 2H), 3.38-3.58 (m, 3H), 3.76 (s, 3H), 5.72-5.89 (m, 3H), 8.03 (s, 1H) One exchangeable proton not observed. | System 3 Method D | m/z 288 (M + H)$^+$ (ES$^+$), at 2.01 min, 245 nm |
| 11-2 | (R)-4-(3-Ethyl-1-methyl-1H-pyrazol-4-yl)-6-(3-(methylamino)pyrrolidin-1-yl)pyrimidin-2-amine dihydrochloride | D (Steps 2 and 3) 81 and 4 | Solid isolated from deprotection step | $^1$H NMR (400 MHz, DMSO-d6) δ 1.16-1.25 (m, 3H), 2.17-2.46 (m, 2H), 2.55-2.65 (m, 3H), 2.78-2.90 (m, 2H), 3.61-3.72 (m, 1H), 3.76-3.94 (m, 7H), 6.07-6.10 (m, 1H), 8.43 (s, 1H), 9.27-9.69 (m, 2H), 12.62 (br. s, 1H) Two exchangeable protons not observed. | System 4 Method G | m/z 302 (M + H)$^+$ (ES$^+$), at 2.38 min, 254 nm |
| 11-3 | (R)-4-(3-Cyclopropyl-1-methyl-1H-pyrazol-4-yl)-6-(3-(methylamino)pyrrolidin-1-yl)pyrimidin-2-amine dihydrochloride | D (Steps 2 and 3) 82 and 4 | Solid isolated from deprotection step | $^1$H NMR (400 MHz, DMSO-d6) δ 0.76-0.87 (m, 2H), 0.94-1.03 (m, 2H), 2.03-2.16 (m, 1H), 2.24-2.45 (m, 2H), 2.56-2.65 (m, 3H), 3.62-3.74 (m, 1H), 3.78-3.97 (m, 7H), 6.41 (s, 1H), 8.49 (s, 1H), 9.21-9.71 (m, 2H), 12.77 (br. s, 1H) Two exchangeable protons not observed. | System 4 Method G | m/z 314 (M + H)$^+$ (ES$^+$), at 2.47 min, 254 nm |
| 11-4 | (R)-4-(1-Methyl-3-(trifluoromethyl)-1H-pyrazol-4-yl)-6-(3-(methylamino)pyrrolidin-1-yl)pyrimidin-2-amine dihydrochloride | D (Steps 2 and 3) 83 and 4 | Solid isolated from deprotection step | $^1$H NMR (400 MHz, DMSO-d6) δ 2.25-2.44 (m, 2H), 2.53-2.62 (m, 3H), 3.54-3.96 (m, 5H), 4.02 (s, 3H), 6.12-6.22 (m, 1H), 8.61-8.67 (m, 1H), 9.46-9.69 (m, 2H), 9.87-9.99 (m, 1H), 13.09-13.21 (m, 1H) One exchangeable proton not observed. | System 4 Method G | m/z 342 (M + H)$^+$ (ES$^+$), at 2.72 min, 254 nm |
| 11-5 | (R)-4-(2-Amino-6-(3-(methylamino)pyrrolidin-1-yl)pyrimidin-4-yl)-1-methyl-1H-pyrazole- | D 84, 8 and 4 | Solid isolated from deprotection | $^1$H NMR (400 MHz, DMSO-d6) δ 2.23-2.44 (m, 2H), 2.56-2.65 (m, 3H), 3.58-3.72 (m, 1H), 3.73-3.96 (m, 4H), 4.05 (s, 3H), 6.48 (s, 1H), 8.73 (s, 1H), 9.08-9.62 (m, 2H), 13.20 (br. s, 1H) Two exchangeable protons not observed. | System 4 Method G | m/z 299 (M + H)$^+$ (ES$^+$), at 2.35 min, 254 nm |

-continued

| Ex. No. | Name | Synthetic Method and Intermediates Used | Isolation Method | $^1$H NMR | LCMS System and Method | LCMS data |
|---|---|---|---|---|---|---|
| | 3-carbonitrile dihydrochloride | | step | | | |
| 11-6 | (R)-4-(1-(difluoromethyl)-3-methyl-1H-pyrazol-4-yl)-6-(3-(methylamino)pyrrolidin-1-yl)pyrimidin-2-amine dihydrochloride | D 85, 8 and 4 | Solid isolated from deprotection step | $^1$H NMR (400 MHz, DMSO-d6) δ 2.22-2.45 (m, 2H), 2.58-2.66 (m, 3H), 3.63-3.75 (m, 1H), 3.78-3.99 (m, 4H), 6.30 (s, 1H), 7.91 (t, J = 59.0 Hz, 1H), 8.89 (s, 1H), 9.18-9.67 (m, 2H), 12.81 (br. s, 1H) Two exchangeable protons not observed and aromatic CH3 under DMSO peak. | System 4 Method G | m/z 324 (M + H)$^+$ (ES$^+$), at 2.46 min, 254 nm |
| 11-7 | Isomer 2: 4-(1,3-Dimethyl-1H-pyrazol-4-yl)-6-(3-methyl-3-(methylamino)pyrrolidin-1-yl)pyrimidin-2-amine | N 1, 80 and 88 | RP HPLC followed by Chiral HPLC | $^1$H NMR (400 MHz, Methanol-d4) δ 1.31 (s, 3H), 1.86-2.00 (m, 1H), 2.01-2.14 (m, 1H), 2.38 (s, 3H), 2.44 (s, 3H), 3.34-3.70 (m, 4H), 3.85 (s, 3H), 5.92 (s, 1H), 7.92 (s, 1H) Three exchangeable protons not observed. | System 2 Method E | m/z 302 (M + H)$^+$ (ES$^+$), at 2.92 min, 202 nm |
| 11-8 | Isomer 1: 4-(1,3-Dimethyl-1H-pyrazol-4-yl)-6-(octahydro-6H-pyrrolo[3,4-b]pyridin-6-yl)pyrimidin-2-amine | O 89 and 90 | RP HPLC followed by Chiral SFC | $^1$H NMR (400 MHz, Methanol-d4) δ 1.46-1.57 (m, 1H), 1.60-1.71 (m, 1H), 1.74-1.86 (m, 2H), 2.37-2.50 (m, 4H), 2.59-2.72 (m, 1H), 2.89-3.01 (m, 1H), 3.38-3.72 (m, 5H), 3.85 (s, 3H), 5.94 (s, 1H), 7.92 (s, 1H) Three exchangeable protons not observed. | System 3 Method D | m/z 314 (M + H)$^+$ (ES$^+$), at 2.33 min, 254 nm |
| 11-8 | Isomer 2: 4-(1,3-Dimethyl-1H-pyrazol-4-yl)-6-(octahydro-6H-pyrrolo[3,4-b]pyridin-6-yl)pyrimidin-2-amine | O 89 and 90 | RP HPLC followed by Chiral SFC | $^1$H NMR (400 MHz, Methanol-d4) δ 1.43-1.56 (m, 1H), 1.60-1.71 (m, 1H), 1.72-1.86 (m, 2H), 2.30-2.53 (m, 4H), 2.57-2.73 (m, 1H), 2.84-3.02 (m, 1H), 3.34-3.73 (m, 5H), 3.85 (s, 3H), 5.93 (s, 1H), 7.91 (s, 1H) Three exchangeable protons not observed. | System 3 Method D | m/z 314 (M + H)$^+$ (ES$^+$), at 2.32 min, 254 nm |
| 12-1 | (R)-4-(1,5-Dimethyl-1H-pyrazol-4-yl)-6-(3-(methylamino)pyrrolidin-1-yl)pyrimidin-2-amine | E 4 and 91 DCM absent in Step 2 | RP HPLC | $^1$H NMR (400 MHz, Methanol-d4) δ 1.92-2.07 (m, 1H), 2.24-2.39 (m, 1H), 2.49-2.60 (m, 6H), 3.42-3.59 (m, 3H), 3.61-3.80 (m, 2H), 3.83 (s, 3H), 5.97 (s, 1H), 7.78 (s, 1H) Three exchangeable protons not observed. | System 2 Method E | m/z 288 (M + H)$^+$ (ES$^+$), at 1.94 min, 213 nm |
| 12-2 | (R)-4-(2-Amino-6-(3-(methylamino)pyrrolidin-1-yl)pyrimidin-4-yl)-1-methyl-1H-pyrazole-5-carbonitrile dihydrochloride | D 92, 8 and 4 | Solid isolated from deprotection step | $^1$H NMR (400 MHz, DMSO-d6) δ 2.21-2.46 (m, 2H), 2.55-2.65 (m, 3H), 3.73-4.03 (m, 5H), 4.13 (s, 3H), 6.47 (s, 1H), 8.49 (s, 1H), 9.15-9.75 (m, 2H), 13.28 (br. s, 1H) Two exchangeable protons not observed. | System 4 Method G | m/z 299 (M + H)$^+$ (ES$^+$), at 2.31 min, 254 nm |
| 12-3 | (R)-4-(1-(Difluoromethyl)-5-methyl-1H-pyrazol-4-yl)-6-(3-(methylamino)pyrrolidin-1-yl)pyrimidin-2-amine dihydrochloride | D 93, 8 and 4 | Solid isolated from deprotection step | $^1$H NMR (400 MHz, DMSO-d6) δ 2.19-2.46 (m, 2H), 2.56-2.63 (m, 3H), 2.66 (s, 3H), 3.61-3.73 (m, 1H), 3.77-3.98 (m, 4H), 6.23-6.35 (m, 1H), 7.99 (t, J = 57.2 Hz, 1H), 8.24 (s, 1H), 9.27-9.78 (m, 2H), 12.84 (br. s, 1H) Two exchangeable protons not observed. | System 4 Method G | m/z 324 (M + H)$^+$ (ES$^+$), at 2.54 min, 254 nm |
| 12-4 | (R)-4-(5,6-Dihydro-4H-pyrrolo[1,2-b]pyrazol-3-yl)-6-(3-(methylamino)pyrrolidin-1-yl)pyrimidin-2-amine dihydrochloride | D (Steps 2 and 3) 94 and 4 | Solid isolated from deprotection step | $^1$H NMR (400 MHz, DMSO-d6) δ 2.20-2.44 (m, 2H), 2.56-2.71 (m, 5H), 3.15-3.26 (m, 2H), 3.61-3.73 (m, 1H), 3.74-3.96 (m, 4H), 4.12-4.23 (m, 2H), 5.96-6.03 (m, 1H), 8.35 (s, 1H), 9.18-9.43 (m, 1H), 9.54 (br. s, 1H), 12.75 (br. s, 1H) Two exchangeable protons not observed. | System 4 Method G | m/z 300 (M + H)$^+$ (ES$^+$), at 2.20 min, 254 nm |
| 13-1 | (R)-4-(3-(methylamino)pyrrolidin-1-yl)-6-(1,3,5-trimethyl-1H-pyrazol-4-yl)pyrimidin-2-amine | C 4 and 95 | RP HPLC | $^1$H NMR (400 MHz, Methanol-d4) δ 1.83-2.00 (m, 1H), 2.17-2.31 (m, 4H), 2.37 (s, 3H), 2.43 (s, 3H), 3.32-3.41 (m, 2H), 3.43-3.53 (m, 1H), 3.55-3.81 (m, 5H), 5.78 (s, 1H) Three exchangeable protons not observed. | System 2 Method E | m/z 302 (M + H)$^+$ (ES$^+$), at 2.03 min, 202 nm |
| 14-1 | (R)-6-(1,5-Dimethyl-1H-pyrazol-4-yl)-4-(3-(methylamino)pyrrolidin-1-yl)pyridin-2-amine dihydrochloride | P 99 and 3 | Solid isolated from deprotection step | $^1$H NMR (400 MHz, Methanol-d4) δ 2.29-2.38 (m, 1H), 2.49 (s, 3H), 2.52-2.62 (m, 1H), 2.82 (s, 3H), 3.88 (s, 3H), 3.83-3.98 (m, 4H), 4.00-4.08 (m, 1H), 5.78 (d, J = 2.3 Hz, 1H), 6.24 (d, J = 2.2 Hz, 1H), 7.75 (s, 1H) Five exchangeable protons not observed. | System 4 Method G | m/z 287 (M + H)$^+$ (ES$^+$), at 2.76 min, 254 nm |
| 15-1 | (R)-4-(3-Ethyl-1H-pyrazol-5-yl)-6-(3-(methylamino) | F 102, 13 and 4 | Solid isolated from | $^1$H NMR (400 MHz, Methanol-d4) δ 2.23-2.30 (m, 5H), 2.37-2.52 (m, 2H), 2.55-2.68 (m, 1H), 2.83-2.91 (m, 2H), 3.73-4.14 (m, 5H), 5.49 (s, 1H), 6.33 (s, 1H) | System 4 Method G | m/z 288 (M + H)$^+$ (ES$^+$), at |

-continued

| Ex. No. | Name | Synthetic Method and Intermediates Used | Isolation Method | ¹H NMR | LCMS System and Method | LCMS data |
|---|---|---|---|---|---|---|
| | pyrrolidin-1-yl) pyrimidin-2-amine dihydrochloride | | deprotection step | | | 2.71 min, 254 nm |
| 15-2 | 4-(3-(Methyl-amino)azetidin-1-yl)-6-(3-(trifluoromethyl)-1H-pyrazol-5-yl) pyrimidin-2-amine | G 15, 16, 17 and 119 | RP HPLC | ¹H NMR (400 MHz, Methanol-d4) δ 2.37 (s, 3H), 3.65-3.74 (m, 1H), 3.79-3.87 (m, 2H), 4.22-4.30 (m, 2H), 6.17 (s, 1H), 7.12 (s,1H) | System 2 Method E | m/z 314 (M + H)⁺ (ES⁺), at 2.60 min, 243 nm |
| 16-1 | (S)-4-(4-Methyl-1H-pyrazol-5-yl)-6-(3-(methylamino) pyrrolidin-1-yl) pyrimidin-2-amine ditrifluoroacetate | H 1, 19 and 103 | RP HPLC | ¹H NMR (400 MHz, Methanol-d4) δ 2.23-2.42 (m, 1H), 2.36 (s, 3H), 2.46-2.66 (m, 1H), 2.82 (s, 3H), 3.76-3.93 (m, 2H), 3.96-4.12 (m, 3H), 6.33 (s, 1H), 7.67 (s, 1H) | System 2 Method E | m/z 274 (M + H)⁺ (ES⁺), at 2.01 min, 241 nm |
| 16-2 | 4-(4-Methyl-1H-pyrazol-5-yl)-6-(3-methyl-3-(methylamino) pyrrolidin-1-yl) pyrimidin-2-amine ditrifluoroacetate | H 1, 19 and 104 HCl/ dioxane used in final step | RP HPLC | ¹H NMR (400 MHz, Methanol-d4) δ 1.59 (d, J = 7.0 Hz, 3H), 2.24-2.44 (m, 1H), 2.37 (d, J = 5.9 Hz, 3H), 2.46-2.55 (m, 1H), 2.77 (d, J = 8.3 Hz, 3H), 3.78-4.12 (m, 4H), 6.32 (d, J = 3.9 Hz, 1H), 7.67 (s, 1H) | System 1 Method I | m/z 288 (M + H)⁺ (ES⁺), at 1.88 min, 240 nm |
| 16-3 | 4-(4-Methyl-1H-pyrazol-5-yl)-6-(3-(methylamino) azetidin-1-yl) pyrimidin-2-amine ditrifluoroacetate | H 1, 19 and 119 | RP HPLC | ¹H NMR (400 MHz, Methanol-d4) δ 2.34 (s, 3H), 2.79 (s, 3H), 4.19-4.52 (m, 3H), 4.53-4.75 (m, 2H), 6.16 (s, 1H), 7.66 (s, 1H) | System 2 Method E | m/z 260 (M + H)⁺ (ES⁺), at 2.05 min, 202 nm |
| 16-4 | 4-(3-Aminoazetidin-1-yl)-6-(4-methyl-1H-pyrazol-5-yl) pyrimidin-2-amine ditrifluoroacetate | H 1, 19 and 105 | RP HPLC | ¹H NMR (400 MHz, Methanol-d4) δ 2.34 (s, 3H), 4.22-4.43 (m, 3H), 4.53-4.76 (m, 2H), 6.16 (s, 1H), 7.66 (s, 1H) | System 2 Method E | m/z 246 (M + H)⁺ (ES⁺), at 1.92 min, 202 nm |
| 16-5 | 4-(4-Methyl-1H-pyrazol-5-yl)-6-(3-methyl-3-(methylamino) azetidin-1-yl) pyrimidin-2-amine ditrifluoroacetate | H 1, 19 and 106 HCl/ dioxane used in final step | RP HPLC | ¹H NMR (400 MHz, Methanol-d4) δ 1.74 (s, 3H), 2.34 (s, 3H), 2.79 (s, 3H), 4.20-4.61 (m, 4H), 6.17 (s, 1H), 7.67 (s, 1H) | System 2 Method E | m/z 274 (M + H)⁺ (ES⁺), at 2.15 min, 240 nm |
| 16-6 | 4-(Hexahydropyrrolo [3,4-b]pyrrol-5(1H)-yl)-6-(4-methyl-1H-pyrazol-5-yl) pyrimidin-2-amine | H 1, 19 and 107 | RP HPLC | ¹H NMR (400 MHz, DMSO-d6) δ 1.73-1.78 (m, 1H), 1.98-2.03 (m, 1H), 2.29 (s, 3H), 2.59-2.67 (m, 1H), 2.74-2.89 (m, 2H), 2.90-3.00 (m, 1H), 3.16-3.92 (m, 5H), 4.07-4.48 (m, 4H), 5.87 (s, 1H), 5.94 (s, 1H), 6.12 (s, 1H), 7.43 (s, 1H) | System 3 Method J | m/z 286 (M + H)⁺ (ES⁺), at 4.46 min, 304 nm |
| 16-7 | 4-(4-Methyl-1H-pyrazol-5-yl)-6-((4aR,7aR)-octahydro-6H-pyrrolo[3,4-b] pyridin-6-yl) pyrimidin-2-amine ditrifluoroacetate | H 1, 19 and 108 HCl/ dioxane used in final step | RP HPLC | ¹H NMR (400 MHz, Methanol-d4) δ 1.77-2.06 (m, 4H), 2.37 (s, 3H), 2.78-3.02 (m, 1H), 3.02-3.15 (m, 1H), 3.35-3.46 (m, 1H), 3.59-3.76 (m, 1H), 3.84-4.20 (m, 4H), 6.32 (d, J = 14.3 Hz, 1H), 7.67 (s, 1H) | System 3 Method J | m/z 300 (M + H)⁺ (ES⁺), at 3.76 min, 254 nm |
| 16-8 | (R)-4-(4-(Difluoromethyl)-1H-pyrazol-5-yl)-6-(3-(methylamino) pyrrolidin-1-yl) pyrimidin-2-amine ditrifluoroacetate | G 111, 16, 17 and 3 TFA and TfOH, microwave 80° C. used in final step | RP HPLC | ¹H NMR (400 MHz, Methanol-d4) δ 2.20-2.36 (m, 1H), 2.45-2.59 (m, 1H), 2.79 (s, 3H), 3.62-3.89 (m, 3H), 3.89-4.05 (m, 2H), 6.49 (s, 1H), 7.37 (t, J = 55.4 Hz, 1H), 8.08 (s, 1H) | System 2 Method E | m/z 308 (M − H)⁻ (ES⁻), at 2.27 min, 238 nm |
| 16-9 | (R)-4-(3-(Methylamino) pyrrolidin-1-yl)-6-(4-(trifluoromethyl)-1H-pyrazol-5-yl) pyrimidin-2-amine ditrifluoroacetate | G 114, 16, 17 and 3 TFA/ DCM used in final step | RP HPLC | ¹H NMR (400 MHz, Methanol-d4) δ 2.21-2.43 (m, 1H), 2.47-2.65 (m, 1H), 2.81 (s, 3H), 3.72-3.89 (m, 2H), 3.93-4.11 (m, 3H), 6.47 (s, 1H), 8.43 (s, 1H) | System 2 Method E | m/z 328 (M + H)⁺ (ES⁺), at 2.33 min, 236 nm |

-continued

| Ex. No. | Name | Synthetic Method and Intermediates Used | Isolation Method | ¹H NMR | LCMS System and Method | LCMS data |
|---|---|---|---|---|---|---|
| 16-10 | (R)-4-(4-Fluoro-1H-pyrazol-5-yl)-6-(3-(methylamino)pyrrolidin-1-yl)pyrimidin-2-amine ditrifluoroacetate | I (Step 3) 118 | RP HPLC | ¹H NMR (400 MHz, Deuterium Oxide) δ 2.27-2.47 (m, 1H), 2.52-2.68 (m, 1H), 2.84 (s, 3H), 3.77-3.95 (m, 2H), 3.97-4.16 (m, 3H), 6.53 (s, 1H), 7.84 (d, J = 4.4 Hz, 1H) | System 4 Method G | m/z 278 (M + H)⁺ (ES⁺), at 2.26 min, 254 nm |
| 16-11 | (R)-4-(3-aminopyrrolidin-1-yl)-6-(4-chloro-1H-pyrazol-5-yl)pyrimidin-2-amine dihydrochloride | I 18 and 24 | Solid isolated from deprotection step | ¹H NMR (400 MHz, Methanol-d4) δ 2.16-2.36 (m, 1H), 2.42-2.65 (m, 1H), 3.49-4.20 (m, 5H), 6.82 (s, 1H), 8.01 (s, 1H) | System 4 Method G | m/z 280 (M + H)⁺ (ES⁺), at 2.14 min, 254 nm |
| 16-12 | (R)-4-(4-bromo-1H-pyrazol-3-yl)-6-(3-(methylamino)pyrrolidin-1-yl)pyrimidin-2-amine | G 3, 16, 17 and 120 | RP HPLC | ¹H NMR (400 MHz, Methanol-d4) δ 1.96 (brs, 1H), 2.28 (brs, 1H), 2.46 (s, 3H), 3.33-3.41 (m, 2H), 3.54 (brs, 1H), 3.67-3.76 (m, 2H), 6.57 (s, 1H), 7.71 (s, 1H) | System 3 Method K | m/z 338/340 (M + H)⁺ (ES⁺), at 4.49 min, 240 nm |
| 16-13 | 4-(4-bromo-1H-pyrazol-3-yl)-6-(3-(methylamino)azetidin-1-yl)pyrimidin-2-amine | G 3, 16, 17 and 119 | RP HPLC | ¹H NMR (400 MHz, Methanol-d4) δ 2.38 (s, 3H), 3.70-3.75 (m, 1H), 3.83-3.86 (m, 2H), 4.26-4.30 (m, 2H), 6.42 (s, 1H), 7.70 (brs, 1H) | System 2 Method E | m/z 324/326 (M + H)⁺ (ES⁺), at 2.18 min, 215 nm |
| 16-14 | (R)-4-(3-(methylamino)pyrrolidin-1-yl)-6-(4-(methylthio)-1H-pyrazol-3-yl)pyrimidin-2-amine | G 3, 16, 17 and 121 | RP HPLC | ¹H NMR (400 MHz, Methanol-d4) δ 1.95 (1H, s), 2.27 (1H, s), 2.41 (3H, s), 2.45 (3H, s), 3.39 (2H, m), 3.51-3.54 (1H, s), 3.68-3.75 (2H, m), 6.72(1H, s), 7.66(1H, s) | System 1 Method I | m/z 306 (M + H)⁺ (ES⁺), at 2.14 min, 220 nm |
| 17-1 | 4-(4,5-dimethyl-1H-pyrazol-3-yl)-6-(3-(methylamino)azetidin-1-yl)pyrimidin-2-amine | G 3, 16, 17 and 122 | RP HPLC | ¹H NMR (400 MHz, Methanol-d4) δ 2.24 (s, 6H), 2.39 (s, 3H), 3.73 (brs, 1H), 3.85 (t, J = 4.8 Hz, 2H), 4.29 (t, J = 7.2 Hz, 2H), 6.01 (brs, 1H) | System 2 Method E | m/z 274 (M + H)⁺ (ES⁺), at 2.12 min, 241 nm |
| 17-2 | (R)-4-(5-methyl-4-(trifluoromethyl)-1H-pyrazol-3-yl)-6-(3-(methylamino)pyrrolidin-1-yl)pyrimidin-2-amine ditrifluoroacetate | I 4, 13, 124 | RP HPLC | ¹H NMR (400 MHz, Methanol-d4) δ 2.24-2.64 (m, 5H), 2.80 (s, 3H), 3.70-4.10 (m, 5H), 6.43 (s, 1H) | System 4 Method G | m/z 342 (M + H)⁺ (ES⁺), at 2.99 min, 254 nm |
| 17-3 | (R)-4-(4-fluoro-5-methyl-1H-pyrazol-3-yl)-6-(3-(methylamino)pyrrolidin-1-yl)pyrimidin-2-amine ditrifluoroacetate | G 3, 16, 17 and 125 | PR HPLC | ¹H NMR (400 MHz, DMSO-d6 + Deuterium Oxide) δ 2.30 (s, 3H), 2.39 (brs, 2H), 2.66 (s, 3H), 3.85-3.72 (m, 3H), 3.93 (brs, 2H), 6.31 (s, 1H) | System 2 Method E | m/z 292 (M + H)⁺ (ES⁺), at 2.16 min, 239 nm |
| 17-4 | (S)-4-(4-chloro-3-methyl-1H-pyrazol-5-yl)-6-(3-(methylamino)pyrrolidin-1-yl)pyrimidin-2-amine dihydrochloride | G 16, 17, 103 and 126 | Solid isolated from deprotection step | ¹H NMR (400 MHz, Methanol-d4) δ 2.24-2.64 (m, 5H), 2.80 (s, 3H), 3.70-4.10 (m, 5H), 6.43 (s, 1H) | System 4 Method G | m/z 308 (M + H)⁺ (ES⁺), at 2.29 min, 254 nm |
| 17-5 | 4-(4-chloro-5-methyl-1H-pyrazol-3-yl)-6-(3-(methylamino)azetidin-1-yl)pyrimidin-2-amine | G 16, 17, 119 and 126 | RP HPLC | ¹H NMR (400 MHz, DMSO-d6) δ 2.10 (s, 3H), 2.66 (s, 3H), 4-1-4-3 (m, 2H), 4.44 (m, 2H), 4.61 (s, 1H), 6.50 (s, 1H), 7.31 (brs, 1H), 8.47 (brs,1H), 9.75(brs,1H), 11.98(brs,1H), 1 4.13 (s, 1H) | System 2 Method E | m/z 294 (M + H)⁺ (ES⁺), at 2.35 min, 241 nm |
| 17-6 | 4-(3-aminoazetidin-1-yl)-6-(4-chloro-5-methyl-1H-pyrazol-3-yl)pyrimidin-2-amine ditrifluoroacetate | G 16, 17, 105 and 126 | RP HPLC | ¹H NMR (400 MHz, DMSO-d6) δ 14.10 (s, 1H), 11.95 (s, 1H), 8.48 (s, 3H), 7.29 (s, 1H), 6.49 (s, 1H), 4.61 (s, 1H), 4.45 (s, 1H), 4.1-4.3 (m, 3H), 2.32 (s, 3H). | System 2 Method E | m/z 280 (M + H)⁺ (ES⁺), at 2.09 min, 202 nm |

-continued

| Ex. No. | Name | Synthetic Method and Intermediates Used | Isolation Method | $^1$H NMR | LCMS System and Method | LCMS data |
|---|---|---|---|---|---|---|
| 17-7 | 4-(4-chloro-5-methyl-1H-pyrazol-3-yl)-6-((4aR,7aR)-octahydro-6H-pyrrolo[3,4-b]pyridin-6-yl)pyrimidin-2-amine dihydrochloride | G 16, 17, 108 and 126 | Solid isolated from deprotection step | $^1$H NMR (400 MHz, DMSO-d6) δ 1.60-1.77 (m, 5H), 2.32 (s, 3H) 2.79-2.91 (m, 2H), 3.22-3.14 (m, 1H), 3.62-4.05 (m, 4H), 6.63 (s, 1H), 7.46 (s, 1H), 8.42 (s, 1H), 9.10-9.30 (m, 1H), 10.06 (s, 1H), 11.99 (s, 1H), 14.23 (s, 1H). | System 4 Method G | m/z 334 (M + H)$^+$ (ES$^+$), at 2.96 min, 254 nm |
| 17-8 | (R)-3-(2-amino-6-(3-(methylamino)pyrrolidin-1-yl)pyrimidin-4-yl)-5-methyl-1H-pyrazol-4-ol | G 3, 16, 17 and 127 BBr3 final step | RP HPLC | $^1$H NMR (400 MHz, Methanol-d4) 1.97 (brs, 1H), 2.22 (s, 3H), 2.30 (m, 1H), 2.48(s, 3H), 3.2-3.8 (m, 5H) 6.29 (s, 1H) | System 2 Method E | m/z 290 (M + H)$^+$ (ES$^+$), at 1.95 min, 202 nm |
| 17-9 | (R)-4-(4-methoxy-5-methyl-1H-pyrazol-3-yl)-6-(3-(methylamino)pyrrolidin-1-yl)pyrimidin-2-amine | G 3, 16, 17 and 127 BBr3 final step | RP HPLC | $^1$H NMR (400 MHz, DMSO-d6) 1.78 (s, 1H), 2.02 (s, 1H), 2.14 (s, 3H), 2.28 (s, 3H), 3.20-3.58 (m, 5H), 3.73 (s, 3H), 5.86 (s, 2H), 6.19 (s, 1H), 12.45 (s, 1H) | System 2 Method E | m/z 304 (M + H)$^+$ (ES$^+$), at 2.03 min, 202 nm |
| 17-10 | (R)-4-(3-(difluoromethyl)-4-methyl-1H-pyrazol-5-yl)-6-(3-(methylamino)pyrrolidin-1-yl)pyrimidin-2-amine ditrifluoroacetate | H 1, 3 and 129 | RP HPLC | $^1$H NMR (400 MHz, Methanol-d4) δ 2.33-2.34 (m, 1H), 2.43 (s, 3H), 2.61 (brs, 1H), 2.85 (s, 3H), 3.89-4.08 (m, 5H), 6.38 (s, 1H), 6.77 (t, J = 55.2 Hz, 1H) | System 2 Method E | m/z 324 (M + H)$^+$ (ES$^+$), at 2.51 min, 245 nm |
| 17-11 | 4-(3-(difluoromethyl)-4-methyl-1H-pyrazol-5-yl)-6-(3-(methylamino)azetidin-1-yl)pyrimidin-2-amine ditrifluoroacetate | H 1, 119 and 129 | RP HPLC | $^1$H NMR (400 MHz, Methanol-d4) δ 2.35 (s, 3H), 2.81 (s, 3H), 4.28-4.33 (m, 1H), 4.42 (brs, 2H), 4.66 (brs, 2H), 6.23 (s, 1H), 7.08 (t, J = 53.4 Hz, 1H) | System 2 Method E | m/z 310 (M + H)$^+$ (ES$^+$), at 2.13 min, 245 nm |
| 17-12 | (R)-4-(4-methyl-3-(trifluoromethyl)-1H-pyrazol-5-yl)-6-(3-(methylamino)pyrrolidin-1-yl)pyrimidin-2-amine dihydrochloride | F 4, 13 and 131 | Solid isolated from deprotection step | $^1$H NMR (400 MHz, Methanol-d4) δ 2.16-2.36 (m, 3H), 2.42-2.67 (m, 2H), 3.65 (s, 3H), 3.71-4.20 (m, 5H), 6.85 (s, 1H) | System 4 Method G | m/z 341 (M + H)$^+$ (ES$^+$), at 3.26 min, 254 nm |
| 17-13 | (R)-4-(5-ethyl-4-fluoro-1H-pyrazol-3-yl)-6-(3-(methylamino)pyrrolidin-1-yl)pyrimidin-2-amine ditrifluoroacetate | G 3, 16, 17 and 132 | RP HPLC | $^1$H NMR (400 MHz, DMSO-d6) δ 13.76 (s, 1H), 11.99 (s, 1H), 9.07 (s, 1H), 8.96 (s, 1H), 8.39 (s, 1H), 7.21 (s, 1H), 6.32 (d, J = 10.9 Hz, 1H), 3.91-3.71 (m, 6H), 2.70 (dd, J = 17.5, 8.9 Hz, 5H), 2.29 (m, 1H), 1.26 (t, J = 7.6 Hz, 3H). | System 2 Method E | m/z 304 (M + H)$^+$ (ES$^+$), at 2.44 min, 202 nm |
| 17-14 | (R)-4-(3-chloro-4-methyl-1H-pyrazol-5-yl)-6-(3-(methylamino)pyrrolidin-1-yl)pyrimidin-2-amine dihydrochloride | F 4, 13 and 134 | Solid isolated from deprotection step | $^1$H NMR (400 MHz, Methanol-d4) δ 2.20-2.30 (s, 4H), 2.35-2.65 (m, 2H), 2.81 (s, 3H), 3.76-4.15 (m, 4H), 6.36 (s, 1H) | System 4 Method G | m/z 308 (M + H)$^+$ (ES$^+$), at 2.82 min, 254 nm |
| 17-15 | (R)-4-(4,5-dichloro-1H-pyrazol-3-yl)-6-(3-(methylamino)pyrrolidin-1-yl)pyrimidin-2-amine | G 3, 16, 17 and 135 | RP HPLC | $^1$H NMR (400 MHz, Methanol-d4) δ 1.89 (brs, 1H), 2.21 (brs, 1H), 2.40 (s, 3H,) 3.25-3.8(m, 5H) 6.44(s, 1H) | System 2 Method E | m/z 328 (M + H)$^+$ (ES$^+$), at 2.81 min, 245 nm |
| 17-16 | 4-(4, 5-dichloro-1H-pyrazol-3-yl)-6-(3-(methylamino)azetidin-1-yl)pyrimidin-2-amine | G 16, 17, 119 and 135 | RP HPLC | $^1$H NMR (400 MHz, Methanol-d4) δ 2.78 (s, 3H), 4.18-4.20 (m, 3H), 4.47 (brs, 2H), 6.46 (s, 1H) | System 2 Method E | m/z 314 (M + H)$^+$ (ES$^+$), at 2.71 min, 245 nm |
| 17-17 | (R)-4-(4-chloro-3-methoxy- | G 3, 16, 17 | Solid isolated | $^1$H NMR (400 MHz, Methanol-d4) δ 2.05-2.60 (m, 3H), 2.69 (s, 3H), 3.43-3.82 (m, 4H), 3.95 (s, 3H), 6.62 (s, 1H) | System 4 Method G | m/z 324 (M + H)$^+$ |

-continued

| Ex. No. | Name | Synthetic Method and Intermediates Used | Isolation Method | $^1$H NMR | LCMS System and Method | LCMS data |
|---|---|---|---|---|---|---|
| | 1H-pyrazol-5-yl)-6-(3-(methylamino)pyrrolidin-1-yl)pyrimidin-2-amine dihydrochloride | and 136 | from deprotection step | | | (ES$^+$), at 2.71 min, 254 nm |
| 18-1 | (R)-6-(4-methyl-1H-pyrazol-5-yl)-4-(3-(methylamino)pyrrolidin-1-yl)pyridin-2-amine ditrifluoroacetate | H 3, 19 and 98 | RP HPLC | $^1$H NMR (400 MHz, Methanol-d4) δ 2.37 (4H, s), 2.58-2.63 (1H, m), 2.85 (3H, s), 3.75 (3H, s), 3.96 (1H, s), 4.05-4.07 (1H, m), 5.81 (1H, s), 6.47 (1H, s), 7.67 (1H, s) | System 08 Method J | m/z 273 (M + H)$^+$ (ES$^+$), at 1.91 min, 254 nm |

Biological Activity

Example A

H4 Antagonist Functional cAMP Gi Assay

HEKf cells were infected overnight using baculovirus expressing the human H4 receptor, then centrifuged at 1,200 rpm for 5 min, frozen in cell freezing medium (Sigma) and stored at −150° C. On the day of assay, the cells were thawed and resuspended in HBSS with 500 nM IBMX to achieve a density of 1,500 cells/well. H4 ligands were prepared in DMSO and stamped by LabCyte ECHO acoustic dispensing at 25 nL in low volume plates. 10 μL/well cells were plated in the presence of 1 μM forskolin, subjected to centrifugation at 1,200 rpm for 1 min and incubated for 30 min prior to addition of Cisbio cAMP detection reagents to a total volume 20 μL/well. For the antagonist assay, cells were pre-incubated with H4 antagonist ligands for 30 min prior to addition of EC80 concentration of histamine and a further 30 min incubation. Following detection reagent addition and shaking at room temperature for 60 min, cAMP accumulation was measured using HTRF on a PheraStar plate reader. EC50 values were generated using a 4-parameter logistical fit equation to quantify agonist potencies. Functional antagonist affinity values were generated using the Cheng-Prusoff equation to calculate a pKb value using the antagonist assay data.

H4 Antagonist Functional Dynamic Mass Redistribution Assay

HEKf cells were infected using baculovirus expressing the human H4 receptor, plated into fibronectin-coated EPIC plates at a density of 10,000 cells/well and incubated overnight at 37° C. The medium on cells was changed to 30 μL HBSS with 20 mM HEPES per well and 30 nL DMSO were added per well by LabCyte ECHO acoustic dispensing. Following 2 h equilibration at room temperature, 30 nL of H4 ligands prepared in DMSO were stamped by LabCyte ECHO acoustic dispensing into seeded EPIC plates and cellular dynamic mass redistribution was monitored using a Corning EPIC plate reader. Following 45 min measurement, 30 nL/well of histamine EC80 was added and monitored to obtain antagonist assay data. Maximum baseline-corrected responses in μm were used to generate concentration response curves. EC50 values were generated using a 4-parameter logistical fit equation to quantify agonist potencies. Functional antagonist affinity values were generated using the Cheng-Prusoff equation to calculate a pKb value using the antagonist assay data.

hERG Assay hERG assay data was determined by Metrion Biosciences, Cambridge, UK, using the experimental protocols detailed below:

A Chinese Hamster Ovary (CHO) cell line stably expressing the human ether-à-go-go related gene was grown and passaged under standard culture conditions. Cells were prepared for assays using dissociation protocols designed to optimise cell health, yield, and seal and assay quality. Test samples were provided as 10 mM stock solutions in 100% DMSO. All sample handling and serial dilutions were performed using glass containers and glass-lined plates. A top working concentration of 30 μM was prepared from the 10 mM sample stock solution using a 1:333-fold dilution into external recording solution (0.3% DMSO v/v). In the single-concentration assay, test samples were screened at 30 μM against a minimum of three separate cells. In the pIC$_{50}$ assay, test samples were screened at 1, 3, 10 and 30 μM against a minimum of three separate cells. Each four-point concentration-response curve was constructed using cumulative double sample additions of each concentration to the same cell.

All experiments were performed on the QPatch gigaseal automated patch clamp platform. The composition of external and internal recording solutions for the QPatch experiments is shown in Table A below. All solutions were filtered (0.2 μm) prior to each experiment.

TABLE A

The composition of external and internal solutions (in mM) used in the hERG study

| Constituent | Intracellular Solution (mM) | Extracellular Solution (mM) |
|---|---|---|
| NaCl | — | 140 |
| KCl | 70 | 2 |
| KF | 60 | — |
| HEPES | 10 | 10 |
| MgCl$_2$ | 1 | 1 |
| CaCl$_2$ | — | 2 |
| Glucose | — | 5 |
| EGTA | 5 | — |
| MgATP | 5 | — |
| pH | 7.2 (KOH) | 7.4 (NaOH) |

All recordings were made in the conventional whole-cell configuration and performed at room temperature (~21° C.) using standard single hole chips (Rchip 1.5-4 MΩ). Series resistance (4-15 MΩ) was compensated by >80%. Currents were elicited from a holding potential of −90 mV using the industry standard "+40/−40" voltage protocol as shown in FIG. 1 this was applied at a stimulus frequency of 0.1 Hz.

On achieving the whole-cell configuration, vehicle (0.3% DMSO v/v in external recording solution) was applied to each cell in two bolus additions with a two-minute recording period between each addition to allow stable recordings to be achieved. Following the vehicle period, either:

i) For the single concentration assay—a single concentration of test sample was applied at 30 µM as five bolus additions per test concentration at two-minute intervals; or ii) For the $pIC_{50}$ assay—four concentrations of test sample were applied from 1 µM to 30 µM as two bolus additions per test concentration at two-minute intervals;

and then the effects on hERG tail current amplitude were measured during the four-minute recording period. For each sweep of the voltage protocol, membrane current and the passive properties of the individual cells were recorded by the QPatch assay software (version 5.0). Peak outward tail current amplitude elicited during the test pulse to −40 mV was measured relative to the instantaneous leak current measured during the initial pre-pulse step to −40 mV. For QC purposes, the minimum current amplitude for the assay is >200 pA peak outward current, measured at the end of the vehicle period. The QPatch analysis software calculates the mean peak current for the last three sweeps at the end of each concentration application period and the data is exported to Excel and interrogated using a bioinformatics suite developed running in Pipeline Pilot (Biovia, USA). The template calculates percent inhibition for each test concentration application period as the reduction in mean peak current or charge relative to the value measured at the end of the control (i.e. vehicle) period. The percent inhibition values from each cell are used to construct concentration-response curves employing a four-parameter logistic fit with 0 and 100% inhibition levels fixed at very low and very high concentrations, respectively, and a free Hill slope factor. The $IC_{50}$ (50% inhibitory concentration) and Hill coefficient are then determined, but only data from cells with Hill slopes within 0.5>nH<2.0 are included. The $IC_{50}$ data reported below represents the mean of at least three separate cells (N≥3). By convention, a test sample that fails to achieve >40% block at the top concentration will yield an ambiguous $IC_{50}$ value due to a poor or unconstrained fit. In this instance an arbitrary $IC_{50}$ value is returned that is 0.5 log unit above the highest concentration tested. For example, if a sample fails to demonstrate a mean inhibition of >40% block at a top concentration of 30 µM then an $IC_{50}$ value of 100 µM is reported, i.e. $pIC_{50≤4.0}$.

For compounds containing a pyrrolidine amine, the vast majority of examples have been prepared as single enantiomers with (R)-stereochemistry. Some compounds, however, have been prepared as racemates and then the enantiomers have been separated using the techniques of chiral HPLC or chiral SFC. For these compounds, isomer assignment (Isomer 1, Isomer 2) is based on the retention time of the compound using the separation technique that was performed in the final chiral separation step. By implication, this could be chiral HPLC or chiral SFC retention time, and this will vary from compound to compound.

TABLE 4

H4 and hERG Activity
Table 4

| | H4 Antagonist Activity | | hERG Activity | |
|---|---|---|---|---|
| Ex. No. | Human H4 CAMP fp$K_b$ | Human H4 DMR fp$K_b$ | hERG p$IC_{50}$ | hERG % inhibition at 30 µM |
| Thioperamide[1] | 7.2 | 6.5 | — | — |
| JNJ-7777120[2] | 8.0 | 8.5 | ≤4.0 | — |
| JNJ-39758979[3] | 8.1 | 8.5 | ≤4.0 | — |
| Toreforant[4] | 7.7 | 7.9 | 5.5 | 89 |
| PF-3893787[5] | 9.1 | 9.1 | 5.1 | 67 |
| Compound 61[6] | 9.0 | 9.1 | 5.2 | — |
| Compound 48[7] | 8.1 | 9.0 | — | 55 |
| 1-1 | 7.3 | — | ≤4.0 | — |
| 1-2 | 6.1 | — | — | — |
| 2-1 | 7.4 | — | ≤4.0 | — |
| 2-2 | 7.3 | — | — | 99 |
| 3-1 | 8.1 | — | — | <1 |
| 3-2 | 7.0 | — | — | 39 |
| 3-3 | 7.3 | — | — | — |
| 3-4 | 7.2 | — | — | 45 |
| 3-5 | 7.0 | — | — | 19 |
| 4-1 | 8.9 | 9.3 | ≤4.0 | 14 |
| 4-2 | 8.0 | — | — | 25 |
| 4-3 | 8.9 | 8.9 | — | 34 |
| 4-4 | 7.1 | — | — | 14 |
| 4-5 | 8.0 | 8.6 | — | 18 |
| 5-1 | 6.4 | — | — | — |
| 5-2 | 6.4 | — | — | 71 |
| 6-1 | 7.7 | — | — | 12 |
| 6-2 | 7.4 | — | — | 94 |
| 7-1 | 8.2 | 7.7 | — | 14 |
| 7-2 | 9.6 | — | — | 39 |
| 7-3 | 7.5 | 7.7 | — | — |
| 7-4 | 8.2 | — | — | 16 |
| 7-5 | — | — | — | — |
| 7-6 | 6.4 | — | — | — |
| 7-7 | 8.7 | — | — | 30 |
| 7-8 | 6.9 | — | — | — |
| 8-1 | 7.0 | — | ≤4.0 | — |
| 8-2 | 7.5 | 8.9 | — | 13 |
| 8-3 | 7.4 | — | — | 12 |
| 8-4 | 7.3 | 7.7 | — | 54 |
| 8-5 | 6.6 | — | — | 77 |
| 8-6 | 7.7 | — | 5.2 | — |
| 8-7 | 8.5 | 8.4 | 4.5 | 49 |
| 8-8 | 6.4 | — | — | 44 |
| 8-9 | 6.2 | — | — | — |
| 8-10 | 6.9 | 6.9 | ≤4.0 | — |
| 8-11 | 6.3 | — | — | — |
| 8-12 | 6.1 | — | — | — |
| 8-13 | 6.7 | — | — | — |
| 8-14 | 6.1 | — | — | — |
| 8-15 | 8.6 | — | ≤4.0 | 44 |
| 8-16 | 9.1 | 8.8 | <4 | 33 |
| 8-17 | 7.3 | — | — | 10 |
| 8-18 | 6.3 | — | — | — |
| 9-1 | 8.1 | 8.4 | ≤4.0 | — |
| 9-2 | 7.9 | — | — | 12 |
| 9-3 | 7.8 | 7.8 | — | 24 |
| 9-4 | 7.6 | — | — | 17 |
| 9-5 | 7.4 | — | — | — |
| 9-6 | 8.2 | 8.6 | — | 18 |
| 9-7 | 7.8 | 8.0 | — | 12 |
| 10-1 | 7.3 | 7.4 | — | 21 |
| 11-1 | 7.9 | 8.6 | ≤4.0 | 2 |
| 11-2 | 7.1 | 7.1 | — | 20 |
| 11-3 | 6.3 | — | — | 34 |
| 11-4 | 6.5 | — | — | 46 |
| 11-5 | 6.1 | — | — | — |
| 11-6 | 8.2 | 8.4 | — | 90 |
| 11-7 Isomer 2 | 6.2 | — | — | — |
| 11-8 Isomer 1 | 6.6 | — | — | 28 |
| 11-8 Isomer 2 | 7.9 | 8.1 | — | 34 |
| 12-1 | 8.1 | 8.6 | ≤4.0 | — |
| 12-2 | 6.6 | — | — | 14 |
| 12-3 | 7.8 | 8.2 | — | 47 |
| 12-4 | 6.8 | — | — | 1 |

TABLE 4-continued

H4 and hERG Activity
Table 4

| Ex. No. | H4 Antagonist Activity | | hERG Activity | |
|---|---|---|---|---|
| | Human H4 CAMP fp$K_b$ | Human H4 DMR fp$K_b$ | hERG p$IC_{50}$ | hERG % inhibition at 30 μM |
| 13-1 | 7.7 | 8.3 | — | 7 |
| 14-1 | 7.7 | 7.9 | — | — |
| 15-1 | 8.5 | — | — | 68 |
| 15-2 | — | 8.0 | — | — |
| 16-1 | 7.5 | — | — | 32 |
| 16-2 | 7.3 | — | — | 9 |
| 16-3 | 8.1 | — | — | — |
| 16-4 | 6.4 | — | — | — |
| 16-5 | 7.7 | — | — | — |
| 16-6 | 6.2 | — | — | — |
| 16-7 | — | 8.2 | ≤4.0 | — |
| 16-8 | — | 7.6 | — | — |
| 16-9 | — | 7.7 | — | — |
| 16-10 | 7.9 | — | — | 21 |
| 16-11 | 8.1 | — | — | 27 |
| 16-12 | 9.4 | 9.9 | — | 45 |
| 16-13 | — | 8.3 | — | — |
| 16-14 | — | 7.6 | — | — |
| 17-1 | — | 8.8 | ≤4.5 | — |
| 17-2 | 8.3 | — | — | 39 |
| 17-3 | — | 8.4 | — | — |
| 17-4 | — | 8.3 | — | 39 |
| 17-5 | — | 9.1 | 4.6 | — |
| 17-6 | — | 7.9 | — | — |
| 17-7 | — | 7.5 | — | 38 |
| 17-8 | — | 7.4 | — | — |
| 17-9 | — | 8.4 | — | — |
| 17-10 | 9.6 | — | — | 57 |
| 17-11 | — | 8.5 | — | — |
| 17-12 | 8.8 | — | — | 60 |
| 17-13 | — | 7.3 | — | — |
| 17-14 | 10.2 | — | — | 44 |
| 17-15 | 10.3 | — | — | 75 |
| 17-16 | — | 8.2 | — | — |
| 17-17 | — | 8.3 | — | 49 |
| 18-1 | — | 9.2 | — | — |

[1] Changlu Liu et al, J Pharmacol Exp Ther., 299, (2001), 121-130.
[2] Jennifer D. Venable et al, J. Med. Chem., 48, (2005), 8289-8298.
[3] Brad M. Savall et al, J. Med. Chem., 57, (2014), 2429-2439.
[4] Robin L Thurmond et al, Ann Pharmacol Pharm., 2, (2017), 1-11.
[5] Charles E. Mowbray et al, Bioorg. Med. Chem. Lett., 21, (2011), 6596-6602.
[6] Rogier A. Smits et al, Bioorg. Med. Chem. Lett., 23, (2013), 2663-2670.
[7] Chan-Hee Park et al, J. Med. Chem., 61, (2018), 2949-2961.

The invention claimed is:

1. A compound of the formula (1):

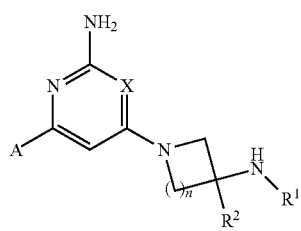

(1)

or a salt thereof, wherein;

X is CH or N;

n is 2;

$R^1$ is selected from H or $C_{1-3}$ alkyl;

$R^2$ is H or methyl; and

A represents an optionally substituted pyrazole ring which is linked to the ring containing X by a carbon-carbon bond, wherein A is selected from the group consisting of:

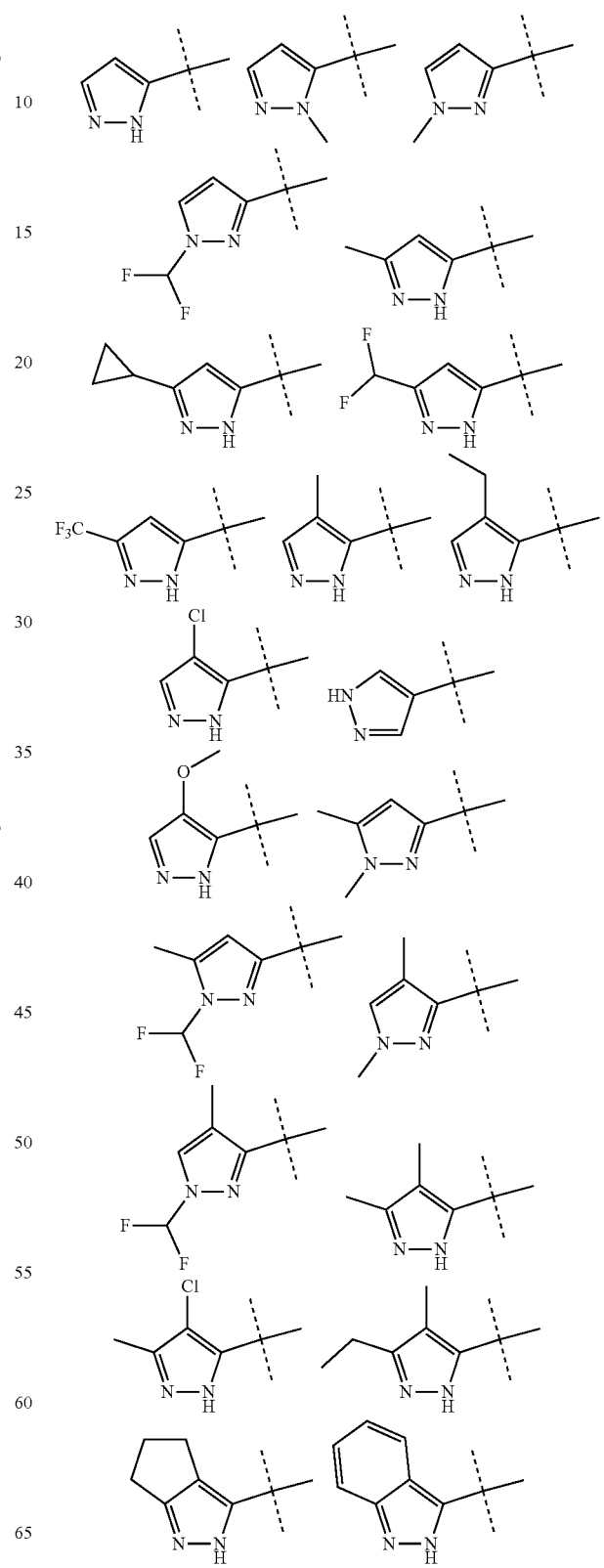

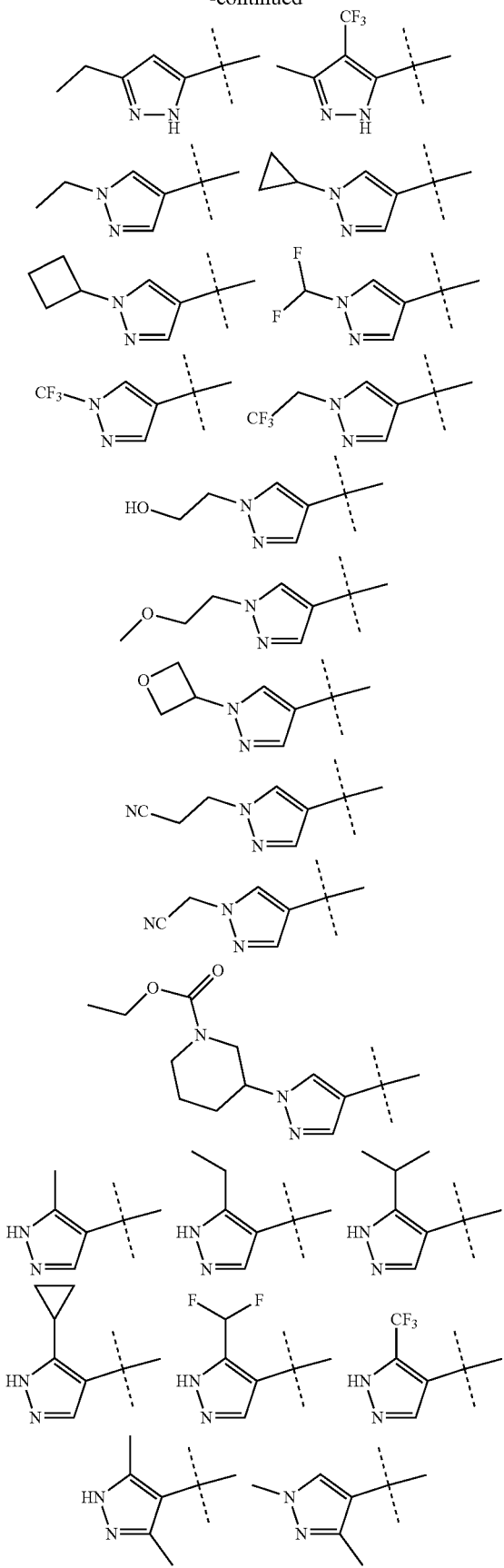
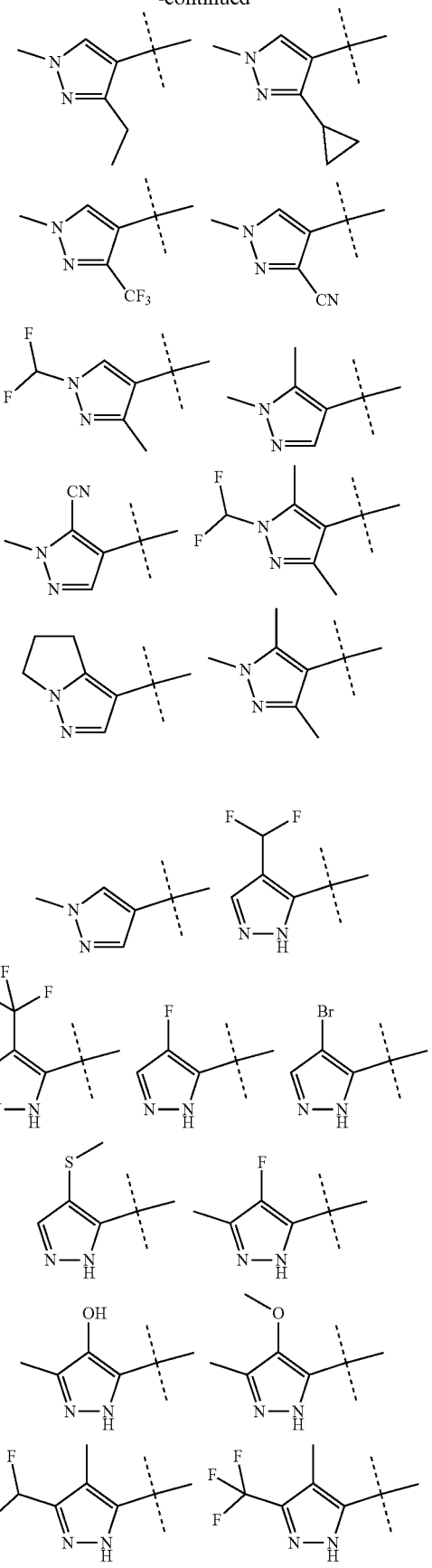

-continued

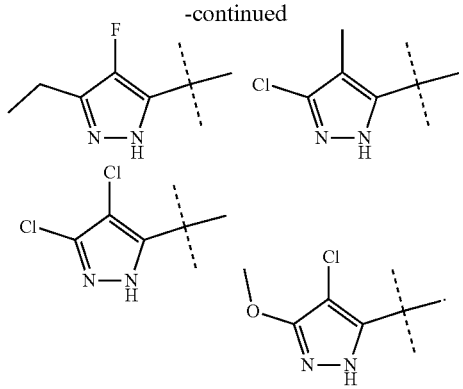

2. The compound according to claim 1, wherein X is N.

3. The compound according to claim 1, wherein $R^1$ is H or methyl.

4. The compound according to claim 1, wherein $R^2$ is H.

5. The compound according to claim 1 which is a compound of formula (2a) or (2b):

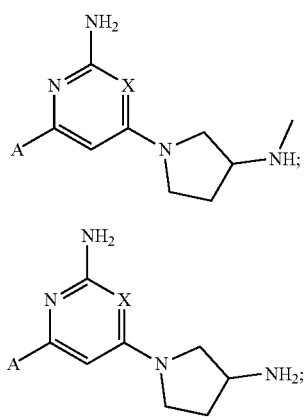

or a salt thereof.

6. The compound according to claim 1 which is a compound of formula (3a) or (3b):

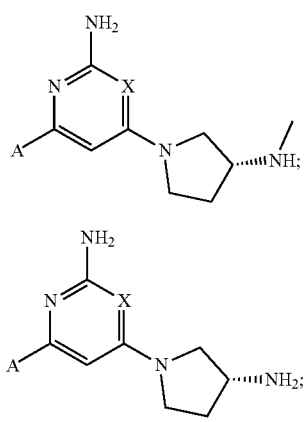

or a salt thereof.

7. The compound according to claim 1 wherein A is:

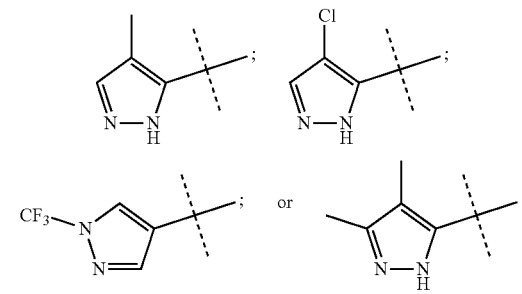

8. The compound according to claim 1 which is selected from the group consisting of:

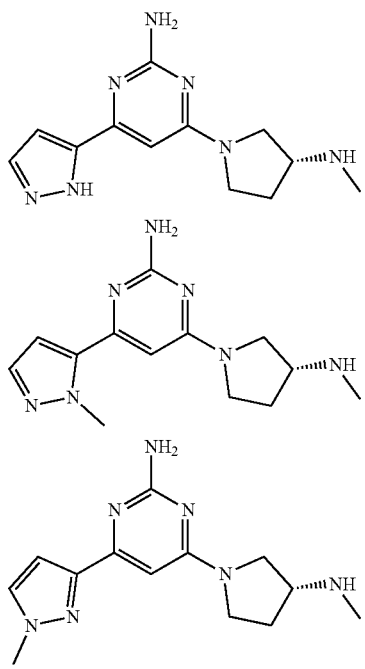

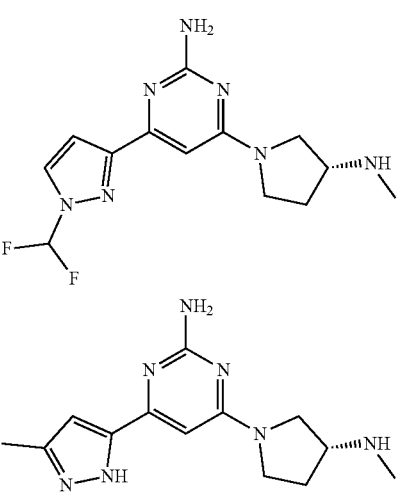

-continued
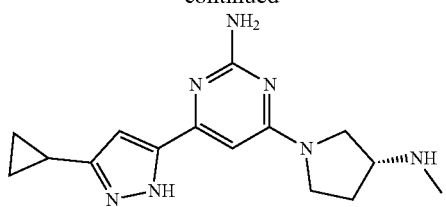
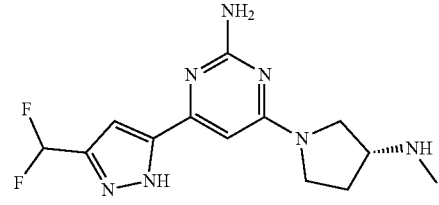
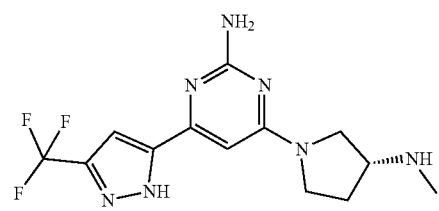
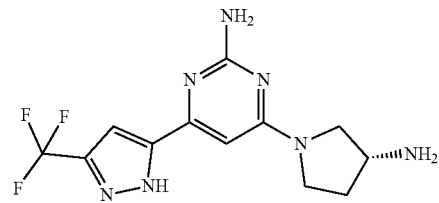
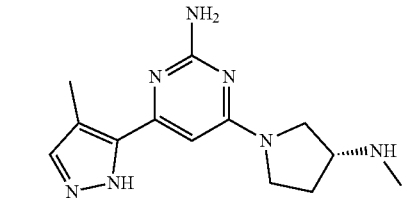
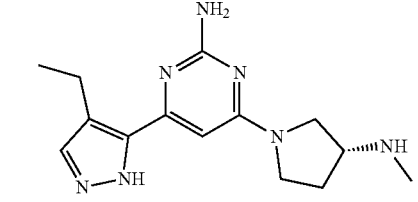
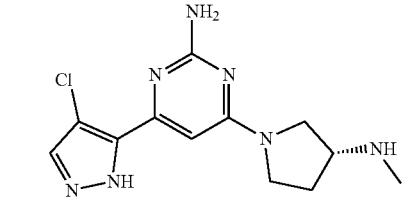
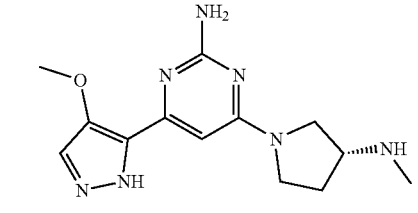
-continued
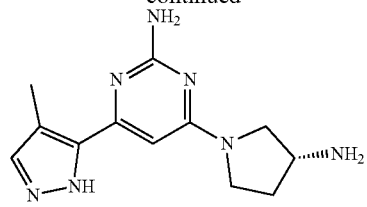
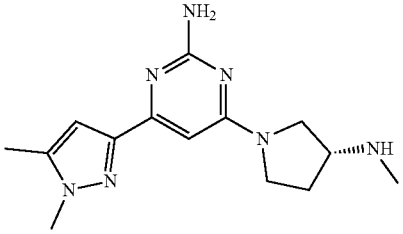
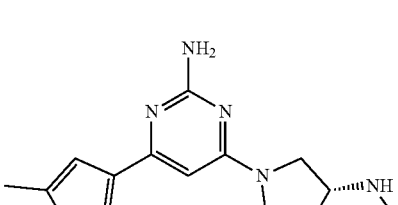
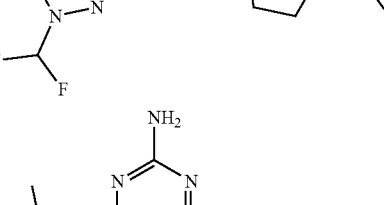
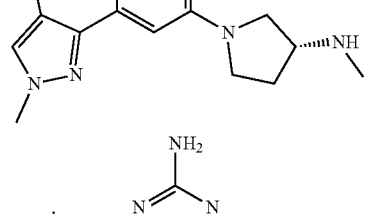
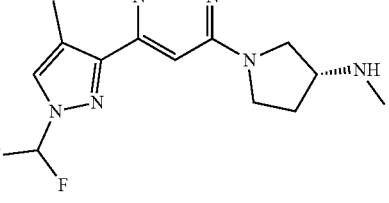
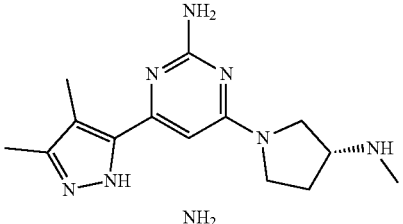
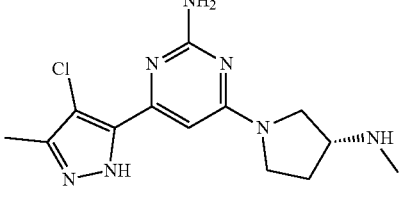

-continued
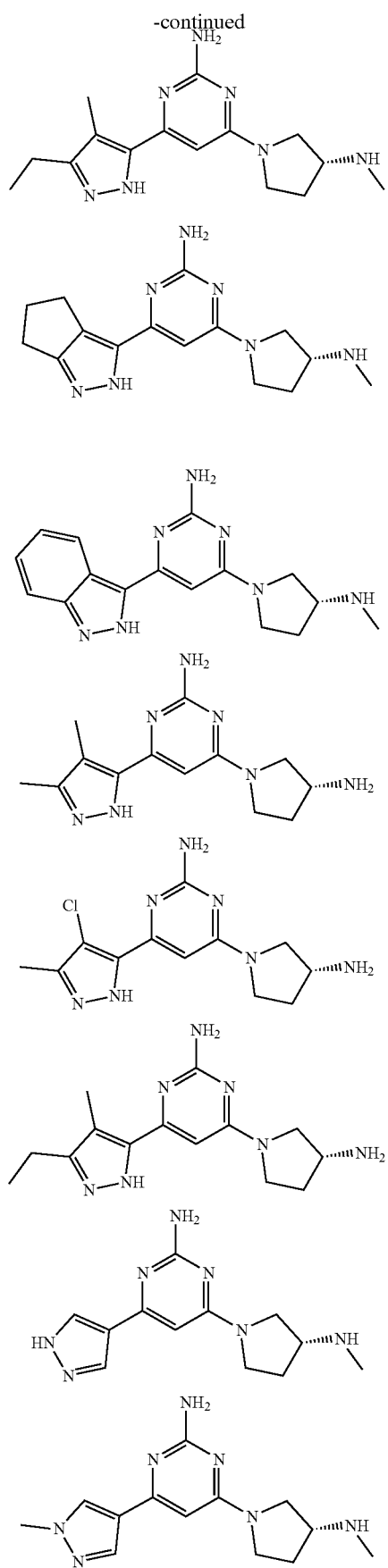
-continued
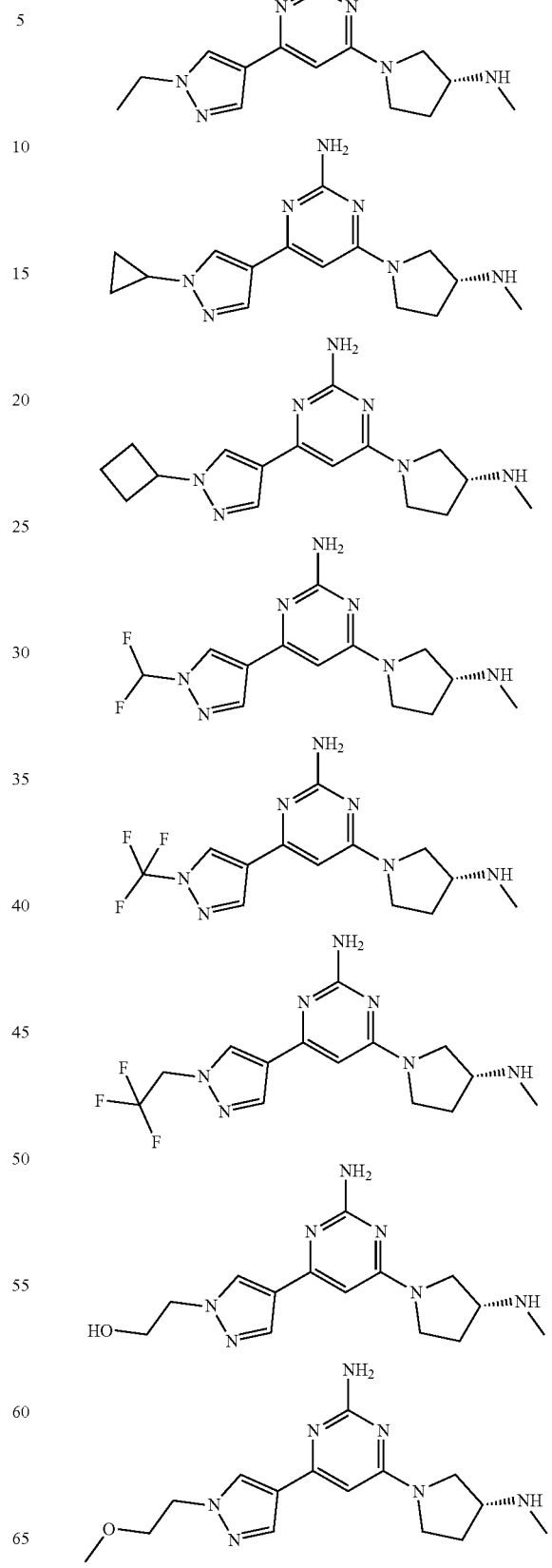

-continued
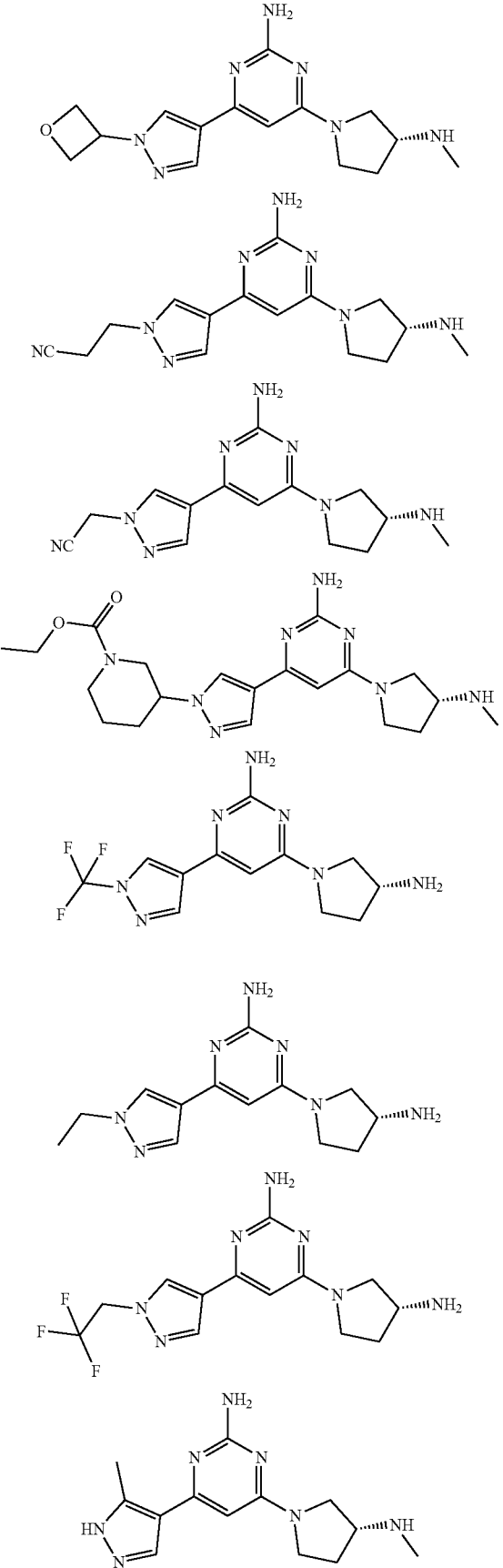
-continued
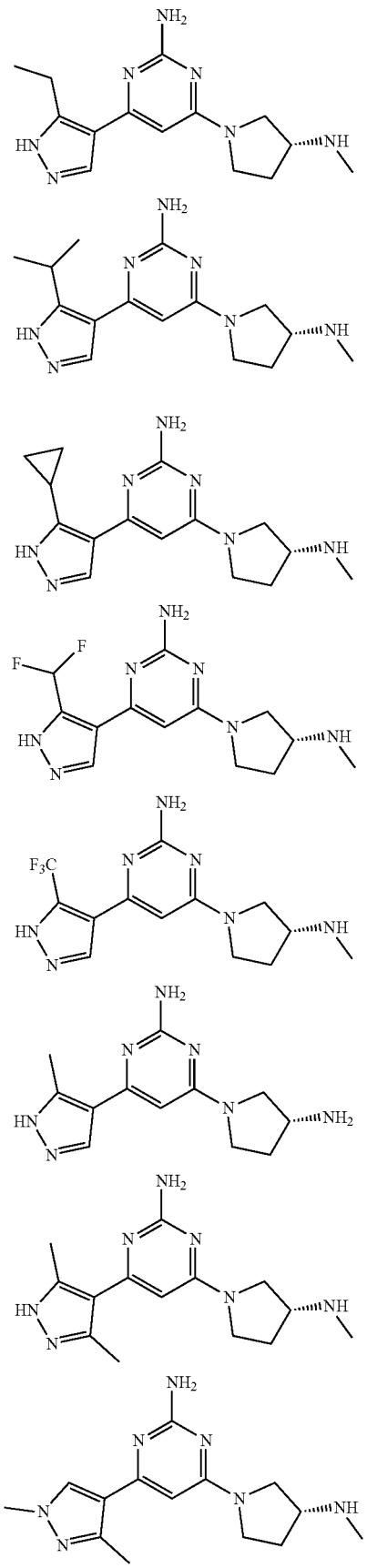

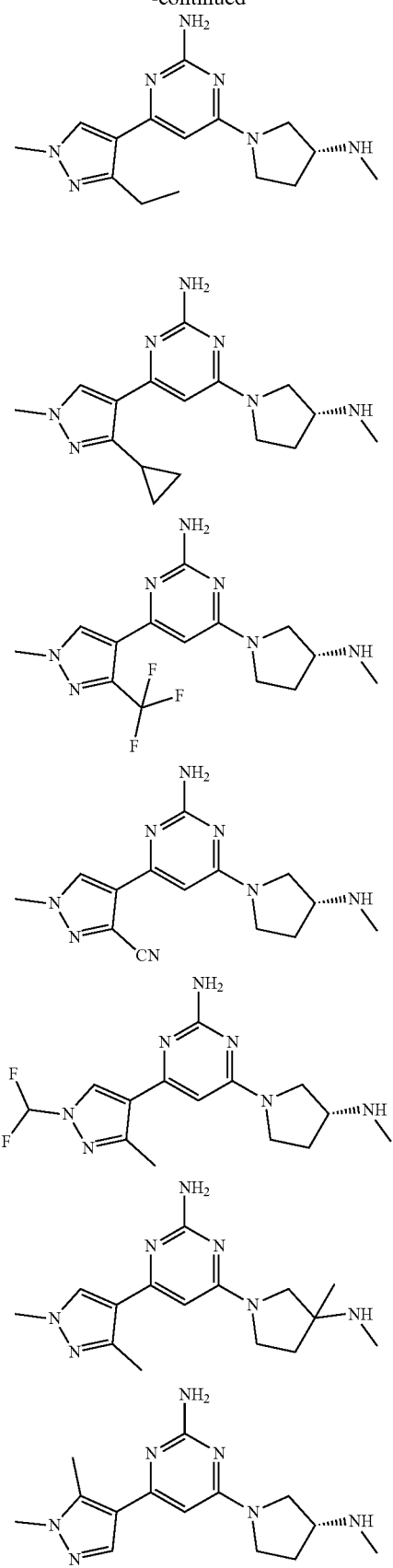

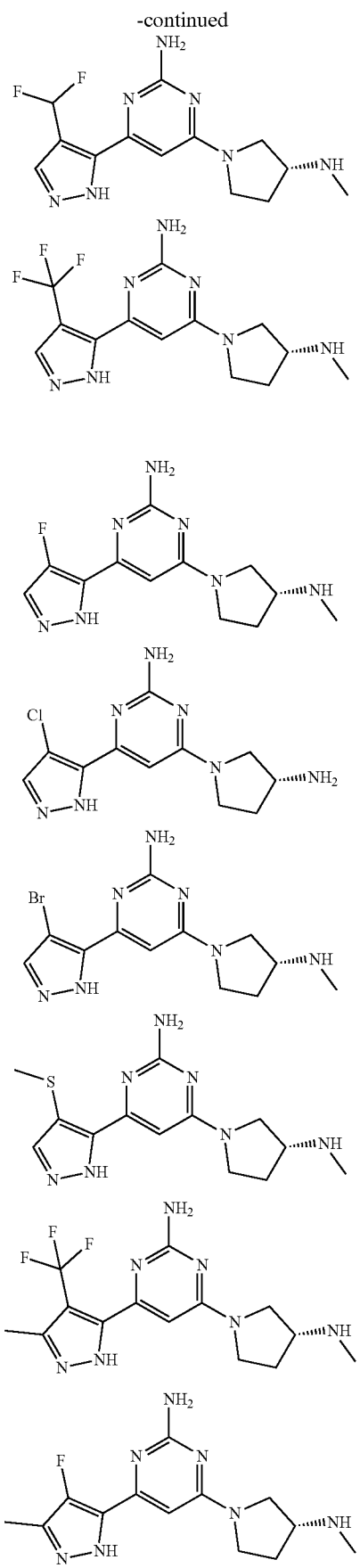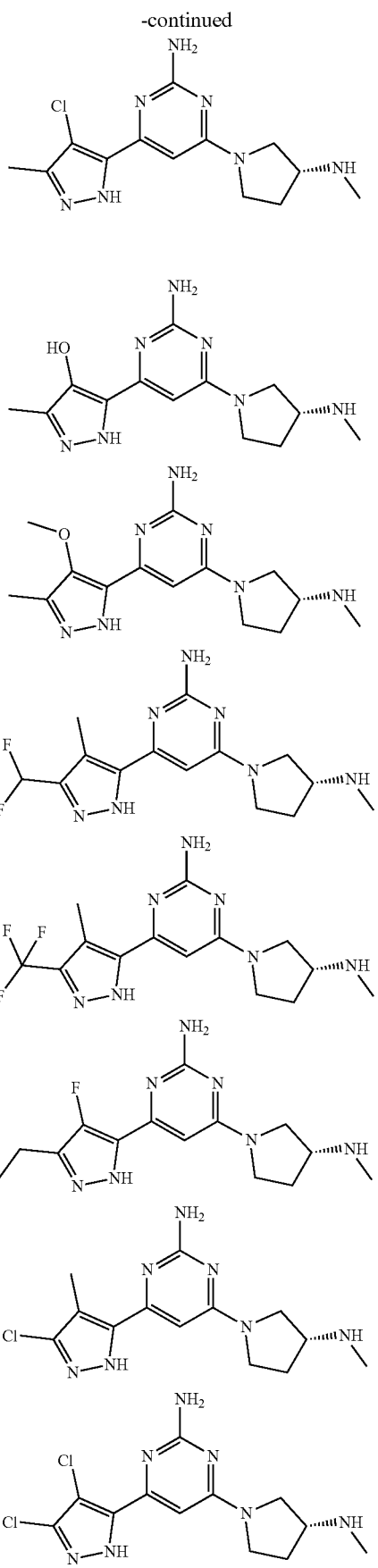

-continued

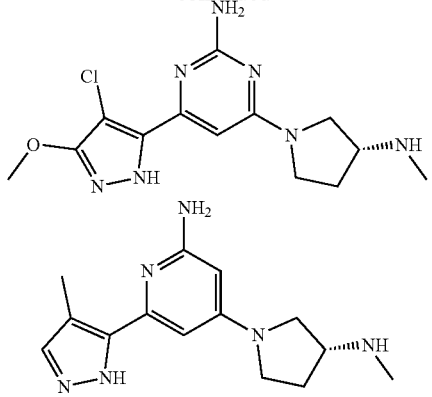

or a salt thereof.

9. The compound according to claim 1 having H4 receptor activity.

10. The compound according to claim 9 which exhibits low hERG activity.

11. A pharmaceutical composition comprising a compound as defined in claim 1 and a pharmaceutically acceptable excipient.

12. A method of treating an inflammatory disorder in a subject with detectable symptoms of an inflammatory disorder, the method comprising administering an effective amount of a compound according to claim 1 to the subject in need thereof.

13. The method of claim 12, wherein the inflammatory disorder is asthma, chronic pruritus, dermatitis, rheumatoid arthritis, gastric ulcerogenesis or colitis.

14. The compound according to claim 1 which is:

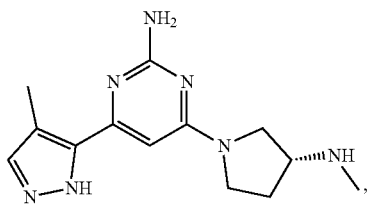 [SMILES: CN[C@@H]1CCN(c2cc(-c3[nH]ncc3C)nc(N)n2)C1]

or a salt thereof.

15. The compound according to claim 1 which is:

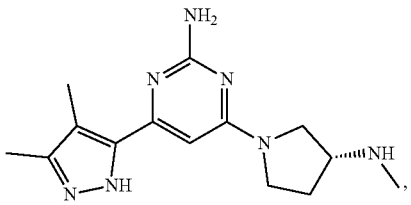

or a salt thereof.

16. The compound according to claim 1 which is:

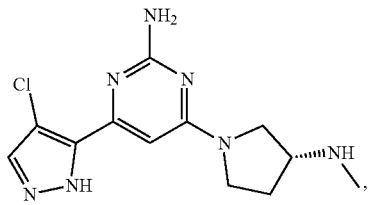

or a salt thereof.

17. The compound according to claim 1 which is:

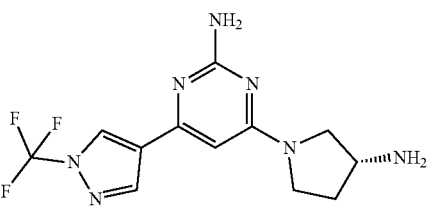 [SMILES: Nc1nc(-c2cnn(C(F)(F)F)c2)cc(N2CC[C@@H](N)C2)n1]

or a salt thereof.

* * * * *